(12) United States Patent
Barrow et al.

(10) Patent No.: US 10,035,799 B2
(45) Date of Patent: Jul. 31, 2018

(54) COMT INHIBITING METHODS AND COMPOSITIONS

(71) Applicant: Lieber Institute for Brain Development, Baltimore, MD (US)

(72) Inventors: James Barrow, Arnold, MD (US); Glen Ernst, Bear, DE (US); Yifang Huang, Lansdale, PA (US); Ingrid Price Buchler, Baltimore, MD (US); Daniel Weinberger, Washington, DC (US)

(73) Assignee: LIEBER INSTITUTE FOR BRAIN DEVELOPMENT, Baltimore, MD (US)

( * ) Notice: Subject to any disclaimer, the term of this patent is extended or adjusted under 35 U.S.C. 154(b) by 0 days.

(21) Appl. No.: 15/011,353

(22) Filed: Jan. 29, 2016

(65) Prior Publication Data

US 2016/0222011 A1    Aug. 4, 2016

Related U.S. Application Data

(60) Provisional application No. 62/109,954, filed on Jan. 30, 2015.

(51) Int. Cl.
| | |
|---|---|
| *A61K 31/00* | (2006.01) |
| *C07D 471/10* | (2006.01) |
| *A61K 31/47* | (2006.01) |
| *C07D 215/36* | (2006.01) |
| *A61K 31/4709* | (2006.01) |
| *C07D 401/12* | (2006.01) |
| *A61K 31/496* | (2006.01) |
| *A61K 31/5377* | (2006.01) |
| *C07D 471/04* | (2006.01) |
| *C07D 401/14* | (2006.01) |
| *A61K 31/55* | (2006.01) |
| *C07D 417/12* | (2006.01) |
| *A61K 31/198* | (2006.01) |
| *A61K 45/06* | (2006.01) |
| *A61K 31/4725* | (2006.01) |

(52) U.S. Cl.
CPC .......... *C07D 471/10* (2013.01); *A61K 31/198* (2013.01); *A61K 31/47* (2013.01); *A61K 31/4709* (2013.01); *A61K 31/4725* (2013.01); *A61K 31/496* (2013.01); *A61K 31/5377* (2013.01); *A61K 31/55* (2013.01); *A61K 45/06* (2013.01); *C07D 215/36* (2013.01); *C07D 401/12* (2013.01); *C07D 401/14* (2013.01); *C07D 417/12* (2013.01); *C07D 471/04* (2013.01)

(58) Field of Classification Search
CPC .. C07D 417/12; C07D 401/12; C07D 401/14; C07D 215/36; A61K 31/47; A61K 31/55; A61K 31/496; A61K 31/4709; A61K 31/5377

USPC ...................................... 514/210.21; 548/400
See application file for complete search history.

(56) References Cited

U.S. PATENT DOCUMENTS

| | | |
|---|---|---|
| 5,834,485 A | 11/1998 | Dyke et al. |
| 2005/0267152 A1 | 12/2005 | Coulton et al. |
| 2008/0161353 A1 | 7/2008 | Barnham et al. |
| 2014/0186280 A1 | 7/2014 | Zurawski et al. |
| 2016/0222001 A1 | 8/2016 | Barrow et al. |

FOREIGN PATENT DOCUMENTS

WO    WO 2011/114099    9/2011

OTHER PUBLICATIONS

Eweas et al, Design, synthesis, anti-schistosomal activity and molecualr docking of novel 8-hydroxyquinoline-5-sulfonyl 1,4-diazepine derivatives ,Bioorganic Chemistry, 2013, 46, p. 17-25.*
Patwa et al, Fries reaction. Part XIII: Preparation of 5- or 7-arylsulfonyl 8-hydroxyquinoline, Journal of the Institution of Chemists (India), 1976, 48, pt. 3, p. 116-18, abstract (1 page).*
Hafez et al, Synthesis and application of some new 5-sulfonyl-N-heterocyclyl-8-hydroxyquinoline derivatvies as potential drugs, Phosphorus, Sulfur and Silicon and the Related Elements, 1991, 61(3-4), p. 381-9, abstract (2 pages).*
Makhlouf et al , Effect of chelating 8-hydroxyquinoline derivatives on the corrosion of zinc in polybasic acids, Journal of the Electrochemical Society of India, 1986,35(2), p. 89-92, an abstract page (Year: 1986).*
Abdel Hafez et al, Synthesis and biological activity of some new 8-hydroxyquinoline sulfonamide derivatives, Phosphorus, Sulfur and the Related Elements, 1988, 40(3-4), p. 219-225 ,an abstract page (Year: 1988).*
Eweas et al, Synthesis, antischstosomal activity and molecular modeling of two novel 8-hydroxyquinoline derivatives, Anti-Infective Agents, 2013, 11(1), p. 31-40, an abstract page (Year: 2013).*
Kassem et al, Synthesis, antimicrobial , and antiviral activities of some new 5-sulphonamido-8-hydroquinoline derivatives, Archives of PharmacalResearch, 2012, 35(6), p. 955-964. (Year: 2012).*
Tewari et al, 8-hydroxyquinolino-5-(p-tolyl)sulfonamide as a new gravimetric reagent for chromium (III), Science and Culture, 1980, 46(10), p. 357-358, an abstract page. (Year: 1980).*

(Continued)

*Primary Examiner* — Taylor V Oh
(74) *Attorney, Agent, or Firm* — Kenneth H. Sonnenfeld; Bryte V. Kelly; King & Spalding LLP

(57) ABSTRACT

The present inventions include a method of inhibiting COMT enzyme in a subject as well as compounds of formula I, or a pharmaceutically acceptable salt thereof, that are useful in the treatment of various disorders mediated by COMT, including Parkinson's disease and/or schizophrenia.

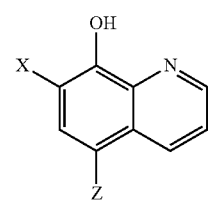

15 Claims, No Drawings

(56) References Cited

OTHER PUBLICATIONS

Thompson et al, 5-chloro-7-diethylaminomethyl-8-quinolinol and of other substituted 8-quinolinols in vitro and in experimental animals, American Journal of Tropical Medicine and hygiene, 1955, 4, p. 224-248. (Year: 1955).*
Abdel Hafez et al , Nitriles in heterocyclic synthesis. Part II. synthesis and application of pyrano[3,2-h]quinoline sulfonamide derivatives, Journal of Chemical Technology and Biotechnology, 1992, 55(2), p. 95-101 ,an abstract page (Year: 1992).*
Kassem et al, Synthesis of some new derivaitves of 8-hydroxyquinoline of possible biological activity, Bulletin of the National Research Centre(Egypt),1997, 22(1), p. 97-106, an abstract page (Year: 1997).*
Musiol et al, Investigating the activity spectrum for ring-substituted 8-hydroxyquinolines, Molecules , 2010, 15, p. 288-304, an abstract page (Year: 2010).*
Lieber Institute for Brain Development, Notification of Transmittal of the International Search Report and the Written Opinion of the International Search Authority, or the Declaration for PCT/US16/15832, 12 pages, dated Apr. 11, 2016.
Ariyasu et al., "Design and Synthesis of 8-hrydroxyquinoline-based Radioprotective Agents," Bioorganic & Medicinal Chemistry, vol. 22, No. 15, pp. 3891-3905, 2014.
Cheng et al., "Solution-processible Small Molecular Organic Light-Emitting Diode Material and Devices based on the Substituted Aluminum Quinolate," Chem. Mater., vol. 16, No. 15, pp. 2862-2868, 2004.
Hafez et al., "Synthesis of Some Heterocyclic Sulfones Related to Quinolinol," Collect. Czech. Chem. Commun., vol. 58, pp. 2222-2226,1993.
Hopkins et al., "Substituted Aluminum and Zinc Quinolates with Blue-Shifted Absorbance/luminescence Bands: Synthesis and Spectroscopic, Photoluminescence, and Electroluminescence Characterization," Chemistry of Materials, vol. 8, No. 2, pp. 344-351, 1996.
Lieber Institute for Brain Development, Supplementary European Search Report for EP 16744242.5, 8 pages, Jan. 8, 2018.

* cited by examiner

COMT INHIBITING METHODS AND COMPOSITIONS

FIELD OF THE INVENTION

This invention relates to compounds, pharmaceutical compositions and their use for treating neuropsychiatric and neurodenerative disorders. In particular, the invention relates to inhibitors of catechol-O-methyltransferase and their use as therapeutics for central nervous system disease.

BACKGROUND

Cognitive disorders are observed in many neurological and psychiatric disorders, be they neurodegenerative (e.g. Parkinson's disease, Alzheimer's disease), neurodevelopmental (e.g. schizophrenia, autism spectrum disorders) or the consequence of other etiology.

Parkinson's disease is a progressive neurodegenerative disorder (synucleopathy) diagnosed on the basis of characteristic motor disturbances, asymmetry of symptoms onset and response to levodopa (Litvan et al., 2003). Lewy bodies, neurofibrillary tangles and plaques are observed in nigral, limbic and neocortical regions. These degenerations are supposed to affect catecholaminergic (dopamine and norepinephrine) and cholinergic neurotransmission. In particular, an important part of cognitive deficits (executive function and working memory) have been related to a decreased prefrontal dopaminergic signaling in non demented patients (Nandakumar et al., 2013).

Schizophrenia is the result of a complex series of neurodevelopmental or other changes that lead to impaired information processing in the brain (Marenco and Weinberger 2000). No single genetic change, aberrant protein function, or visible brain lesion has been demonstrated to lead to schizophrenia, and many different genetic and environmental changes are linked to increased disease risk (Fatemi and Folsom 2009). While many neurochemical signaling systems, such as the various monoamines, NMDA, and GABA, are likely to play a role in the etiology of schizophrenia (Pickard 2011), many pathways seem to converge on aberrant dopamine signaling as a final common pathway that leads to many of the observed symptoms (Howes and Kapur 2009).

With regard to the cognitive impairment, for which there is currently no treatment, patients with schizophrenia show significant deficits in specific cognitive domains, especially executive function, working memory, and episodic memory. Cognitive domains which are dysfunctioning in these two disorders are complex functions involving many neurotransmitters and brain regions; however, dopamine signaling in the dorsolateral prefrontal cortex (DLPFC) has been shown to play a critical role in these processes (Goldman-Rakic, Castner et al. 2004). One approach to rectifying cortical dopamine neurotransmission is to take advantage of the differential modes of clearance of dopamine from the different brain regions. In the midbrain, there is extensive expression of the dopamine transporter (DAT), which is thought to be primarily responsible for dopamine clearance from the synapse (Ciliax, Heilman et al. 1995). In contrast, cortical regions exhibit only low levels of DAT expression, and dopamine is cleared primarily by enzymatic catabolism of dopamine, with a contribution from the norepinephrine transporter (NET) (Yavich, Forsberg et al. 2007; Kaenmaki, Tammimaki et al. 2010). The primary enzymes responsible for dopamine catabolism in the prefrontal cortex ("PFC") are monoamine oxidase (MAO) and catechol-O-methyltransferase ("COMT").

Beyond Parkinson's and schizophrenia, inhibition of COMT may be useful in a number of neuro-psychiatric conditions, including ADHD, obsessive-compulsive disorder, alcoholism, depression, bipolar disorder (Lachman, Papolos et al. 1996), as well as age-associated cognitive symptoms, impulse control disorders, including compulsive gambling, sexual behavior, and other compulsive destructive behaviors. The role of COMT in dopamine metabolism in the brain make it an especially important target for improvement of cognition (Apud and Weinberger 2007).

Additionally, COMT inhibitors have shown utility in Parkinson's disease treatment, due to the role of COMT in metabolizing the dopamine precursor L-DOPA, which is given to Parkinson's disease patients to boost the levels of dopamine in the brain (Bonifacio, Palma et al. 2007). Since dopamine cannot cross the blood-brain barrier, L-DOPA is administered in its place and is transported into the brain and subsequently processed to dopamine. The percentage of exogenously administered L-DOPA that reaches the brain is ~1%, and this low brain availability necessitates a high dose, which leads to peripheral side effects (Nutt and Fellman 1984). The primary enzymes responsible for dopamine metabolism are aromatic amino acid decarboxylase (AAAD) and COMT. Therefore, extensive efforts have been undertaken to develop potent and selective inhibitors of both enzymes. Carbidopa is an AAAD inhibitor now routinely given with L-DOPA, reducing the efficacious L-DOPA dose by 60-80% (Nutt, Woodward et al. 1985). Addition of a COMT inhibitor further decreases the variability of L-DOPA exposure, and a brain-penetrating COMT inhibitor could also increase brain dopamine levels.

Inhibitors of COMT have been developed for treatment of Parkinson's disease (Learmonth, Kiss et al. 2010). Notably, the nitrocatechol scaffold has been exploited to provide the clinically used drugs tolcapone and entacapone (Bonifacio, Palma et al. 2007). While they are effective in blocking peripheral COMT activity, entacapone has negligible brain penetration, and tolcapone has low but measurable levels in the brain (Russ, et al. 1999). Compounds with improved brain penetration should have greater efficacy for Parkinson's disease, as well as have utility for other psychiatric and neurological conditions such as cognitive impairment in schizophrenia. Despite the early clinical success achieved with tolcapone, the drug has been associated with serious liver injury, including three deaths, and requires strict liver function monitoring (Olanow and Watkins 2007). Thus, the risk-benefit profile for tolcapone prevents its widespread deployment, and new, inhibitors of COMT are needed, especially those that are active in the brain. Borchardt disclosed a series of non-nitrocatechol quinoline COMT inhibitors, but these compounds had weak potency (Borchardt, Thakker et al. 1976).

Accordingly, there remains a need for potent inhibitors of COMT and methods of using the same to treat central nervous system disorders.

SUMMARY OF THE INVENTION

The present invention provides compounds, pharmaceutical compositions and methods of treating or preventing neurological or psychiatric disorders for which inhibiting COMT provides a therapeutic effect.

The present invention also provides methods of treating or preventing a neurological or psychiatric disorder, or treating symptoms associated with a neurological or psychiatric disorder, and in particular such disorders for which inhibiting COMT provides a therapeutic effect. In a particular embodiment, the invention provides a method of inhibiting COMT enzyme in a subject by administering compounds according to formula I, or a pharmaceutically acceptable salt thereof:

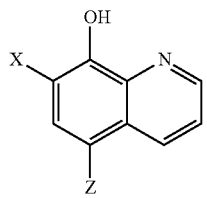

wherein:
X is selected from hydrogen, halogen, C≡N, $CF_3$, and $C_1$-$C_4$ alkyl;
Z is selected from $SO_2R^1$ and $SO_2NR^2R^3$;
$R^1$ is selected from $C_1$-$C_{10}$ alkyl, $C_3$-$C_{10}$ cycloalkyl, aryl, aralkyl, heterocyclyl, heteroaryl and heteroarylalkyl, any of which may be substituted with one or more groups selected from halogen, C≡N, $CF_3$, OH, $C_1$-$C_4$ alkyl or $C_2$-$C_4$ alkenyl, alkoxy, nitro, amino, $C_1$-$C_4$ alkylamino, oxo, $C_3$-$C_{10}$ cycloalkyl, acyl, aryl, aralkyl, heterocyclyl, heteroaryl, $CON(R^4)_2$, $SO_2R^4$, or $SO_2N(R^4)_2$, where each $R^4$ is independently $C_1$-$C_4$ alkyl or $(R^4)_2$ forms a carbocyclic ring;
$R^2$ and $R^3$ are independently selected from hydrogen and any of the groups as defined for $R^1$, with the proviso that at least one of $R^2$ or $R^3$ is different from hydrogen; or $R^2$ and $R^3$ may together form a 3-10 membered monocyclic, bicyclic or spirocyclic nitrogen-containing ring system that contains 0-3 (preferably 0-1) additional heteroatoms selected from oxygen (O), nitrogen (N), and sulfur (S), and which may be further substituted with one or more groups selected from halogen, C≡N, $CF_3$, OH, $C_1$-$C_4$ alkyl or $C_2$-$C_4$ alkenyl, $C_3$-$C_6$ cycloalkyl, alkoxy, nitro, amino, $C_1$-$C_4$ alkoxycarbonyl, acyl, $C_1$-$C_4$ alkylamino, oxo, $SO_2CH_3$, aryl, aralkyl, heterocyclyl, heteroaryl or heteroarylalkyl;
with the proviso that when X is hydrogen and Z is $SO_2R^1$, $R^1$ is not $C_4$ alkyl, $C_8$ alkyl, tetrahydropyran or propylcyclopropane;
or when X is H and Z is $SO_2NR^2R^3$, $R^2$ and $R^3$ do not together form a 1-piperidinyl ring substituted with a α-methyl group;
or when X is Cl and Z is $SO_2R^1$, $R^1$ is not $C_3$ alkyl, $C_4$ alkyl or $C_5$-$C_6$ cycloalkyl;
or when X is Cl and Z is $SO_2NR^2R^3$, $R^2$ and $R^3$ do not together form an unsubstituted, 1-pyrrolidinyl ring;
A further embodiment of the above includes the additional proviso that when X is F and Z is $SO_2R^1$, $R^1$ is not pyridyl, cyclopentyl, or phenyl substituted with fluoro or trifluoromethyl.
A second additional embodiment of the above further includes the proviso that when X is Cl and Z is $SO_2R^1$, $R^1$ is not thiazolyl, pyridyl, pyridyl-N-oxide, and phenyl substituted with one or two groups selected from fluoro, chloro, methyl, trifluoromethyl, phenyl and tert-butyl.
Also provided herein are COMT-inhibiting compounds in accordance with formula I, or pharmaceutically acceptable salts thereof:

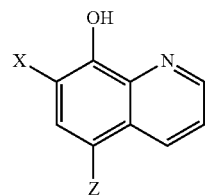

wherein:
X is selected from hydrogen, halogen, C≡N, $CF_3$, and $C_1$-$C_4$ alkyl;
Z is selected from $SO_2R^1$ and $SO_2NR^2R^3$;
$R^1$ is selected from $C_1$-$C_{10}$ alkyl, $C_3$-$C_{10}$ cycloalkyl, aryl, aralkyl, heterocyclyl, heteroaryl and heteroarylalkyl, any of which may be substituted with one or more groups selected from halogen, C≡N, $CF_3$, OH, $C_1$-$C_4$ alkyl or $C_2$-$C_4$ alkenyl, alkoxy, nitro, amino, $C_1$-$C_4$ alkylamino, oxo, $C_3$-$C_{10}$ cycloalkyl, acyl, aryl, aralkyl, heterocyclyl, heteroaryl, $CON(R^4)_2$, $SO_2R^4$, or $SO_2N(R^4)_2$, where each $R^4$ is independently $C_1$-$C_4$ alkyl or $(R^4)_2$ forms a carbocyclic ring;
$R^2$ and $R^3$ are independently selected from hydrogen and any of the groups as defined for $R^1$, with the proviso that at least one of $R^2$ or $R^3$ is different from hydrogen; or $R^2$ and $R^3$ may together form a 3-10 membered monocyclic, bicyclic or spirocyclic nitrogen-containing ring system that contains 0-3 (preferably 0-1) additional heteroatoms selected from oxygen (O), nitrogen (N), and sulfur (S), and which may be further substituted with one or more groups selected from halogen, C≡N, $CF_3$, OH, $C_1$-$C_4$ alkyl or $C_2$-$C_4$ alkenyl, $C_3$-$C_6$ cycloalkyl, alkoxy, nitro, amino, $C_1$-$C_4$ alkoxycarbonyl, acyl, $C_1$-$C_4$ alkylamino, oxo, $SO_2CH_3$, aryl, aralkyl, heterocyclyl, heteroaryl or heteroarylalkyl;
with the proviso that when X is hydrogen and Z is $SO_2R^1$, $R^1$ is not $C_1$ alkyl, $C_4$ alkyl, $C_8$ alkyl, phenyl, 4-methylphenyl, 4-methoxybenzyl, 4-bromophenyl, 4-iodophenyl, 2,4,6-trimethylphenyl, $CH(COMe)_2$, $CH(CO_2Et)_2$, 4-BnOPh, tetrahydropyran or propylcyclopropane;
or when X is H and Z is $SO_2NR^2R^3$, $R^2$ and $R^3$ do not together form a 1-piperidinyl ring substituted with a α-methyl group;
or when X is Cl and Z is $SO_2R^1$, $R^1$ is not $C_3$ alkyl, $C_4$ alkyl or $C_5$-$C_6$ cycloalkyl;
or when X is Cl and Z is $SO_2NR^2R^3$, $R^2$ and $R^3$ do not together form an unsubstituted, 1-pyrrolidinyl ring.
An additional embodiment of the above includes the proviso that when X is F and Z is $SO_2R^1$, $R^1$ is not pyridyl, cyclopentyl and phenyl substituted with fluoro, or trifluoromethyl.
A second additional embodiment of the above further includes the proviso that when X is Cl and Z is $SO_2R^1$, $R^1$ is not thiazolyl, pyridyl, pyridyl-N-oxide, and phenyl substituted with one or two groups selected from fluoro, chloro, methyl, trifluoromethyl, phenyl and tert-butyl.
Also provided herein are pharmaceutical compositions comprising the COMT-inhibiting compounds of the present invention.

DETAILED DESCRIPTION OF THE INVENTION

I. Definitions

The terms below, when used herein, have the following meanings unless indicated otherwise.

As used in this specification and the appended claims, the singular forms "a", "an" and "the" include plural references unless the content clearly dictates otherwise.

When any variable (e.g. aryl, heterocycle, $R^1$, etc.) occurs more than one time in any constituent, its definition on each occurrence is independent at every other occurrence.

"Alkyl" refers to a saturated hydrocarbon chain, in certain embodiments ranging from about 1 to 20 carbon atoms in length, in other embodiments about 1 to 12 carbon atoms in length. Such hydrocarbon chains may be branched or linear. "Alkyl" groups may be substituted by one or more substituents selected from halogen, amido, aryl or alkoxy. Particular alkyl groups according to the present invention include methyl, trifluoromethyl, ethyl, propyl, butyl, pentyl, 1-methylbutyl, 1-ethylpropyl, 3-methylpentyl, octyl and the like.

The term "$C_1$-$C_6$" (for example), or "$C_{1-6}$", includes, for this example, alkyls containing 6, 5, 4, 3, 2, or 1 carbon atom(s).

"Lower alkyl" refers to an alkyl group containing from 1 to 6 carbon atoms, preferably 1 to 4 carbon atoms, and may be linear or branched, as exemplified by methyl, ethyl, isopropyl, isobutyl, n-butyl, and t-butyl. $C_1$-$C_4$ alkyl refers to an alkyl group containing 1 to 4 carbon atoms.

As used herein, "haloalkyl" refers to an alkyl group as described herein containing at least one halogen substituent. One particular example according to the invention is trifluoromethyl.

"Cycloalkyl" refers to a saturated or unsaturated cyclic hydrocarbon radical, including bridged, fused, or spiro cyclic compounds, preferably having 3 to about 10 or 12 carbon atoms, more preferably 3 to about 8. Nonlimiting examples of "$C_3$-$C_6$ cycloalkyl" groups according to the present invention are cyclopropyl, cyclopentyl, cyclohexyl and the like.

As used herein, "alkenyl" refers to a branched or unbranched hydrocarbon having t least one carbon-carbon double bond, and is preferably about 2 to about 15 carbon atoms and containing at least one double bond, such as ethenyl, n-propenyl, isopropenyl, n-butenyl, isobutenyl, octenyl, decenyl, tetradecenyl, and the like. $C_2$-$C_4$ alkenyl refers to an alkenyl group containing 2 to 4 carbon atoms.

The term "alkynyl" as used herein refers to a branched or unbranched hydrocarbon having at least one carbon-carbon triple bond, and is preferably about 2 to about 15 carbon atoms and containing at least one triple bond, such as ethynyl, n-propynyl and the like.

As used herein, "aryl" is intended to mean any stable monocyclic or bicyclic carbon ring of up to 7 members in each ring, wherein at least one ring is aromatic. The "aryl" groups may be unsubstituted or substituted by 1 to 3 substituent independently selected from $C_1$-$C_4$ alkyl, $C_1$-$C_4$ alkoxy, halogen, cyano, amido, hydroxy, aryl or heterocycle. Nonlimiting examples of such aryl elements include phenyl, fluorophenyl, chlorophenyl, methylphenyl, dichlorophenyl, naphthyl, tetrahydronaphthyl, indanyl, biphenyl and the like.

"Aralkyl" refers to an alkyl group having an aryl substituent as defined hereabove. Nonlimiting examples of aralkyl groups according to the present invention are benzyl, 2-chlorobenzyl, 2,3-dichlorobenzyl, 4-fluorobenzyl, 4-methylbenzyl, (4-methylphenyl)ethyl and the like.

"Amino" refers to the group —$NH_2$'.

"$C_1$-$C_4$ alkylamino" refers to the group —NRR' wherein one of R, R' is hydrogen or "$C_1$-$C_4$ alkyl", and the other is $C_1$-$C_4$ alkyl.

"Acyl" refers to the group —C(=O)R where R is "$C_1$-$C_6$ alkyl", "$C_2$-$C_6$ alkenyl", "$C_2$-$C_6$ alkynyl", "$C_3$-$C_8$ cycloalkyl", "heterocycloalkyl", "aryl" or "heteroaryl". A nonlimiting example of an acyl group according to the present invention is acetyl, 2,3-dichlorobenzoyl and the like.

"Alkoxy" refers to the group —OR where R includes "$C_1$-$C_6$ alkyl", "$C_3$-$C_8$ cycloalkyl", "heterocycloalkyl", "aryl", "heteroaryl", "aralkyl" or "heteroarylalkyl". $C_1$-$C_4$ alkoxy refers to the group —OR where R is a $C_1$-$C_4$ alkyl group, Aryloxy refers to the group —OR where R is an aryl group. Arylalkoxy refers to the group —OR where R is an aralkyl group.

"Alkoxycarbonyl" refers to the group —C(O)OR where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. In certain embodiments, the heteroatoms are selected from O and N.

The term "heterocycle" or "heterocyclic" includes heteroaryl moieties. Nonlimiting examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydro isoquinolinyl, tetrahydroquinolinyl, thiamorpholinyl, thiamorpholinyl sulfoxide, thiazolyl, thiazolinyl, thienofuryl, thienothienyl, thienyl and triazolyl.

In certain embodiments, the heterocyclic group is a heteroaryl group. As used herein, the term "heteroaryl" refers to groups having 5 to 14 ring atoms, preferably 5, 6, 9, or 10 ring atoms; having 6, 10, or 14 [pi] electrons shared in a cyclic array; and having, in addition to carbon atoms, between one and about three heteroatoms selected from the group consisting of N, O, and S which may be saturated, such as piperidinyl, partially saturated, or unsaturated, such as pyridinyl, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

In certain other embodiments, the heterocyclic group is fused to an aryl or heteroaryl group. Examples of such fused heterocycles include, without limitation, tetrahydroquinolinyl and dihydrobenzofuranyl. Examples of heterocloalkyls include, without limitation, azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

The term "heteroatom" means O, S or N, selected on an independent basis.

"Halogen" and "halo" refer to fluorine, chlorine, bromine and iodine.

A moiety that is "substituted" is one in which one or more hydrogens have been independently replaced with another chemical substituent. Suitable substituents include, without limitation, halogen, hydroxy, oxo (e.g., an annular —CH— substituted with oxo is —C(=O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

Other possible substituents, which are themselves not further substituted (unless expressly stated otherwise) are: (a) halo, cyano, oxo, carboxy, formyl, nitro, amino, amidino, and guanidino, and (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_2$-$C_{15}$ N,N-alkylcarbamoyl, $C_2$-$C_{15}$ N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing in (b) can be further substituted with one more moieties listed in (a), above. Each instance of $C_8$ noted in this paragraph may be, in further embodiments, $C_6$.

Compounds described herein may contain one or more double bonds and may thus give rise to cis/trans isomers as well as other conformational isomers. The present invention includes all such possible isomers as well as mixtures of such isomers unless specifically stated otherwise.

The compounds of the present invention may contain one or more asymmetric centers and may thus occur as racemates, racemic mixtures, single enantiomers, diastereomeric mixtures, and individual diastereomers.

It will be understood that, as used herein, references to the compounds of the present invention are meant to also include the pharmaceutically acceptable salts, and also salts that are not pharmaceutically acceptable when they are used as precursors to the free compounds or in other synthetic manipulations.

The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamme, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

A "pharmaceutically acceptable excipient" or "pharmaceutically acceptable carrier" refers to an excipient that can be included in the compositions of the invention and that causes no significant adverse toxicological effects to the subject or patient to which the composition is administered. "Pharmacologically effective amount," "physiologically effective amount," and "therapeutically effective amount" are used interchangeably herein to mean the amount of an active agent present in a pharmaceutical preparation that is needed to provide a desired level of active agent and/or conjugate in the bloodstream or in the target tissue. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

The term "patient" refers to a living organism suffering from or prone to a condition that can be prevented or treated by administration of an active agent as described herein, and includes both humans and animals. In one embodiment, the patient is a human patient.

The term "mammal" "mammalian" or "mammals" includes humans, as well as animals, such as dogs, cats, horses, pigs and cattle.

Without being bound by theory, the administration of compounds according to the invention in an "effective amount" or "therapeutically effective amount" provides a concentration of the compound that functions as a COMT inhibitor sufficient to inhibit the effect of the COMT enzyme complex.

"Treating" or "treatment" of a disease state includes: 1) inhibiting the disease state, i.e., arresting the development of the disease state or its clinical symptoms; 2) attenuating the disease state, i.e. reducing the number or intensity of one or more symptoms associated with the disease state, such that one or more symptoms is reduced but may, or may not be completely eliminated; and/or 3) relieving the disease state, i.e., causing temporary or permanent regression of the disease state or its clinical symptoms.

"Prevent" or "preventing" a disease state includes: preventing the disease state, i.e. causing the clinical symptoms of the disease state not to develop in a subject that may be exposed to or predisposed to the disease state, but does not yet experience or display symptoms of the disease state.

All patents, patent applications and publications cited herein, whether supra or infra, are hereby incorporated by reference in their entirety.

II. Methods

One aspect of the invention is a method of treating or preventing a neurological or psychiatric disorder, or treating symptoms associated with a neurological or psychiatric disorder, and in particular such disorders for which inhibiting COMT provides a therapeutic effect. Without being bound by theory, the therapeutic effect provided according to the invention is achieved by inhibiting the metabolism of catecholamines by COMT. Accordingly, in an aspect of the invention, the invention provides methods of treating and/or preventing disease for which inhibiting degradation of catecholamines such as, for example, dopamine, norepinephrine or L-dihydroxyphenylalanine (L-DOPA) provides a beneficial therapeutic effect.

In another aspect, the invention provides a method of inhibiting COMT enzyme in a subject by administering compounds of formula I. These methods comprise administering to a subject in need thereof an effective amount of a COMT-inhibiting compound in accordance with formula I, or a pharmaceutically acceptable salt thereof:

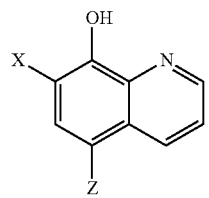

I wherein:

X is selected from hydrogen, halogen, C≡N, $CF_3$, and $C_1$-$C_4$ alkyl;

Z is selected from $SO_2R^1$ and $SO_2NR^2R^3$;

$R^1$ is selected from $C_1$-$C_{10}$ alkyl, $C_3$-$C_{10}$ cycloalkyl, aryl, aralkyl, heterocyclyl, heteroaryl and heteroarylalkyl, any of which may be substituted with one or more groups selected from halogen, C≡N, $CF_3$, OH, $C_1$-$C_4$ alkyl or $C_2$-$C_4$ alkenyl, alkoxy, nitro, amino, $C_1$-$C_4$ alkylamino, oxo, $C_3$-$C_{10}$ cycloalkyl, acyl, aryl, aralkyl, heterocyclyl, heteroaryl, $CON(R^4)_2$, $SO_2R^4$, or $SO_2N(R^4)_2$, where each $R^4$ is independently $C_1$-$C_4$ alkyl or $(R^4)_2$ forms a carbocyclic ring;

$R^2$ and $R^3$ are independently selected from hydrogen and any of the groups as defined for $R^1$, with the proviso that at least one of $R^2$ or $R^3$ is different from hydrogen; or $R^2$ and $R^3$ may together form a 3-10 membered monocyclic, bicyclic or spirocyclic nitrogen-containing ring system that contains 0-3 (preferably 0-1) additional heteroatoms selected from oxygen (O), nitrogen (N), and sulfur (S), and which may be further substituted with one or more groups selected from halogen, C≡N, $CF_3$, OH, $C_1$-$C_4$ alkyl or $C_2$-$C_4$ alkenyl, $C_3$-$C_6$ cycloalkyl, alkoxy, nitro, amino, $C_1$-$C_4$ alkoxycarbonyl, acyl, $C_1$-$C_4$ alkylamino, oxo, $SO_2CH_3$, aryl, aralkyl, heterocyclyl, heteroaryl or heteroarylalkyl;

with the proviso that when X is hydrogen and Z is $SO_2R^1$, $R^1$ is not $C_4$ alkyl, $C_8$ alkyl, tetrahydropyran or propylcyclopropane;

or when X is H and Z is $SO_2NR^2R^3$, $R^2$ and $R^3$ do not together form a 1-piperidinyl ring substituted with an α-methyl group;

or when X is Cl and Z is $SO_2R^1$, $R^1$ is not $C_3$ alkyl, $C_4$ alkyl or $C_5$-$C_6$ cycloalkyl;

or when X is Cl and Z is $SO_2NR^2R^3$, $R^2$ and $R^3$ do not together form an unsubstituted, 1-pyrrolidinyl ring.

An additional embodiment of the above includes the proviso that when X is F and Z is $SO_2R^1$, $R^1$ is not pyridyl, cyclopentyl and phenyl substituted with fluoro, or trifluoromethyl.

A second additional embodiment of the above further includes the proviso that when X is Cl and Z is $SO_2R^1$, $R^1$ is not thiazolyl, pyridyl, pyridyl-N-oxide, and phenyl substituted with one or two groups selected from fluoro, chloro, methyl, trifluoromethyl, phenyl and tert-butyl.

In particular embodiments, $R^1$ is selected from $C_1$-$C_{10}$ alkyl, $C_3$-$C_{10}$ cycloalkyl, aryl, aralkyl, heterocyclyl, heteroaryl and heteroarylalkyl, any of which may be substituted with one or more groups selected from halogen, C≡N, $CF_3$, OH, $C_1$-$C_4$ alkyl or alkenyl, $C_1$-$C_4$ alkoxy, aryloxy, nitro, amino, $C_1$-$C_4$ alkylamino, oxo, $C_3$-$C_6$ cycloalkyl, acyl, aryl, aralkyl, heterocyclyl or heteroaryl.

In other particular embodiments, Z is $SO_2R^1$ and $R^1$ is selected from substituted or unsubstituted $C_1$-$C_{10}$ alkyl, substituted or unsubstituted $C_3$-$C_{10}$ cycloalkyl, substituted or unsubstituted aryl, substituted or unsubstituted aralkyl, substituted or unsubstituted C-attached heterocyclyl, substituted or unsubstituted C-attached heteroaryl or substituted or unsubstituted heteroarylalkyl.

In still other particular embodiments, Z is $SO_2R^1$ and $R^1$ is selected from $C_1$-$C_{10}$ alkyl, $C_3$-$C_{10}$ cycloalkyl, phenyl, naphthyl, aralkyl, C-attached piperidinyl, C-attached 1H-benzimidazolyl, C-attached tetrahydro-2H-pyranyl and pyridinyl, any of which may be substituted with one or more groups selected from halogen, $CF_3$, $C_1$-$C_4$ alkyl, $C_1$-$C_4$ alkoxy, $C_3$-$C_6$ cycloalkyl, substituted or unsubstituted phenyl, substituted or unsubstituted pyridinyl, substituted or unsubstituted quinolinyl, substituted or unsubstituted 1H-indazolyl, substituted or unsubstituted aralkyl or acyl. Certain embodiments include the proviso that when X is fluorine and Z is $SO_2R^1$, $R^1$ is not cyclopentyl.

In further particular embodiments, when Z is $SO_2NR^2R^3$, each of $R^2$ and $R^3$ may be independently selected from hydrogen, $C_1$-$C_{10}$ alkyl, $C_3$-$C_{10}$ cycloalkyl, aryl, aralkyl, heterocyclyl, heteroaryl and heteroarylalkyl, any of which, excluding hydrogen, may be substituted with one or more groups selected from halogen, C≡N, $CF_3$, $C_1$-$C_4$ alkyl or $C_2$-$C_4$ alkenyl, $C_1$-$C_4$ alkoxy, nitro, amino, $C_1$-$C_4$ alkylamino, oxo, $C_3$-$C_6$ cycloalkyl, aryl, aralkyl, heterocyclyl or heteroaryl; with the proviso that at least one of $R^2$ and $R^3$ is different from hydrogen.

In still further particular embodiments, each of $R^2$ and $R^3$ may be independently selected from hydrogen, $C_1$-$C_4$ alkyl, $C_3$-$C_{10}$ cycloalkyl, aryl, aralkyl, heterocyclyl, heteroaryl and heteroarylalkyl, any of which, excluding hydrogen, may be substituted with one or more groups selected from halogen, $CF_3$, $C_1$-$C_4$ alkyl, $C_1$-$C_4$ alkoxy, amino, $C_3$-$C_6$ cycloalkyl, aryl, heterocyclyl or heteroaryl.

In other particular embodiments, $R^2$ is selected from hydrogen or substituted or unsubstituted $C_1$-$C_4$ alkyl.

In still other particular embodiments, R³ is selected from C₁-C₄ alkyl, aryl, aralkyl, heteroaryl and heteroarylalkyl, any of which, excluding hydrogen, may be substituted with one or more groups selected from halogen, C₁-C₄ alkyl or C₁-C₄ alkoxy.

In further particular embodiments, when Z is SO₂NR²R³, R² and R³ may together form a 3-10 membered monocyclic, bicyclic or spirocyclic nitrogen-containing ring system that contains 0-3 additional heteroatoms selected from oxygen (O), nitrogen (N), and sulfur (S), and which may be further substituted with one or more groups selected from halogen, C₁-C₄ alkyl or C₂-C₄ alkenyl, C₃-C₆ cycloalkyl, C₁-C₄ alkoxy, arylalkoxy, nitro, amino, C₁-C₄ alkoxycarbonyl, acyl, C₁-C₄ alkylamino, oxo, SO₂CH₃, aryl, aralkyl, heterocyclyl, or heteroaryl.

In still further particular embodiments, the nitrogen-containing ring system formed by R² and R³ is a 4-7 membered monocyclic ring system or a 8-10 membered bicyclic or spirocyclic nitrogen-containing ring system. In another selected embodiment the monocyclic, bicyclic or spirocyclic nitrogen-containing ring system contains 0-1 additional heteroatoms selected from oxygen (O), nitrogen (N), and sulfur (S).

In other particular embodiments, Z is SO₂NR²R³ with NR²R³ being a substituted or unsubstituted pyrrolidinyl, substituted or unsubstituted piperidinyl, substituted or unsubstituted piperazinyl, substituted or unsubstituted azetidinyl, substituted or unsubstituted 1,3,8-triazaspiro[4.5]decanyl, substituted or unsubstituted dihydroisoquinolinyl, substituted or unsubstituted dihydroisoindolyl, substituted or unsubstituted morpholinyl, substituted or unsubstituted dihydronaphthyridinyl or substituted or unsubstituted azabicyclo[3.2.2]nonyl.

In still other particular embodiments, NR²R³ is a 1-pyrrolidinyl, 1-piperidinyl, 1-piperazinyl, 1-azetidinyl, 1,3,8-triazaspiro[4.5]dec-8-yl, 3,4-dihydro-2(1H)-isoquinolinyl, 1,3-dihydro-2H-isoindol-2-yl, 4-morpholinyl, 5,8-dihydronaphthyridin-7(6H)-yl, azabicyclo[3.2.2]non-3-yl which may be further substituted with one or more groups selected from halogen, C≡N, CF₃, OH, C₁-C₄ alkyl, C₃-C₆ cycloalkyl, C₁-C₄ alkoxy, arylalkoxy, amino, C₁-C₄ alkoxycarbonyl, acyl, C₁-C₄ alkylamino, oxo, aryl, aralkyl, heterocyclyl, or heteroaryl.

The group X in formula I, in selected embodiments, is selected from hydrogen, halogen, trifluoromethyl, methyl and nitrile (C≡N); in further embodiments X in formula I is hydrogen, halogen, trifluoromethyl, or methyl; in further embodiments of this group, said halogen is fluorine or chlorine. In one embodiment, X is fluorine. In another embodiment, X is hydrogen. In another embodiment, X is trifluoromethyl.

In a second aspect, the invention provides a method of inhibiting COMT enzyme in a subject by administering compounds according to formula I. These methods comprise administering to a subject in need thereof an effective amount of a COMT-inhibiting compound in accordance with formula I, or a pharmaceutically acceptable salt thereof:

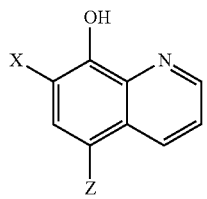

I wherein:
X is selected from H, F, Br, I, C≡N, CF₃, and C₁-C₄ alkyl;
Z is selected from SO₂R¹ and SO₂NR²R³;
R¹ is selected from C₁-C₁₀ alkyl, C₃-C₁₀ cycloalkyl, aryl, aralkyl, heterocyclyl, heteroaryl and heteroarylalkyl, any of which may be substituted with one or more groups selected from halogen, C≡N, CF₃, OH, C₁-C₄ alkyl or C₂-C₄ alkenyl, alkoxy, nitro, amino, C₁-C₄ alkylamino, oxo, C₃-C₁₀ cycloalkyl, acyl, aryl, aralkyl, heterocyclyl, heteroaryl, CON(R⁴)₂, SO₂R⁴, or SO₂N(R⁴)₂, where each R⁴ is independently C₁-C₄ alkyl or (R⁴)₂ forms a carbocyclic ring;
R² and R³ are independently selected from hydrogen and any of the groups as defined for R¹, with the proviso that at least one of R² or R³ is different from hydrogen; or R² and R³ may together form a 3-10 membered monocyclic, bicyclic or spirocyclic nitrogen-containing ring system that contains 0-3 (preferably 0-1) additional heteroatoms selected from oxygen (O), nitrogen (N), and sulfur (S), and which may be further substituted with one or more groups selected from halogen, C≡N, CF₃, OH, C₁-C₄ alkyl or C₂-C₄ alkenyl, C₃-C₆ cycloalkyl, alkoxy, nitro, amino, C₁-C₄ alkoxycarbonyl, acyl, C₁-C₄ alkylamino, oxo, SO₂CH₃, aryl, aralkyl, heterocyclyl, heteroaryl or heteroarylalkyl;
with the proviso that when X is hydrogen and Z is SO₂R¹, R¹ is not C₄ alkyl, C₈ alkyl, tetrahydropyran or propylcyclopropane;
or when X is H and Z is SO₂NR²R³, R² and R³ do not together form a 1-piperidinyl ring substituted with an α-methyl group.

An additional embodiment of the above includes the proviso that when X is F and Z is SO₂R¹, R¹ is not pyridyl, cyclopentyl and phenyl substituted with fluoro, or trifluoromethyl.

A second additional embodiment of the above further includes the proviso that when X is Cl and Z is SO₂R¹, R¹ is not thiazolyl, pyridyl, pyridyl-N-oxide, and phenyl substituted with one or two groups selected from fluoro, chloro, methyl, trifluoromethyl, phenyl and tert-butyl.

In a third aspect, the invention provides a method of inhibiting COMT enzyme in a subject by administering the compounds according to formula I. These methods comprise administering to a subject in need thereof an effective amount of a COMT-inhibiting compound in accordance with formula I, or a pharmaceutically acceptable salt thereof:

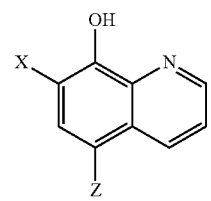

I wherein:
X is selected from halogen, C≡N, CF₃, and C₁-C₄ alkyl;
Z is selected from SO₂R¹ and SO₂NR²R³;
R¹ is selected from C₁-C₁₀ alkyl, C₃-C₁₀ cycloalkyl, aryl, aralkyl, heterocyclyl, heteroaryl and heteroarylalkyl, any of which may be substituted with one or more groups selected from halogen, C≡N, CF₃, OH, C₁-C₄ alkyl or C₂-C₄ alkenyl, alkoxy, nitro, amino, C₁-C₄ alkylamino, oxo, C₃-C₁₀ cycloalkyl, acyl, aryl, aralkyl, heterocyclyl, heteroaryl, CON($R^4$)$_2$, SO$_2$$R^4$, or SO$_2$N($R^4$)$_2$, where each $R^4$ is independently C$_1$-C$_4$ alkyl or ($R^4$)$_2$ forms a carbocyclic ring;

$R^2$ and $R^3$ are independently selected from hydrogen and any of the groups as defined for $R^1$, with the proviso that at least one of $R^2$ or $R^3$ is different from hydrogen; or $R^2$ and $R^3$ may together form a 3-10 membered monocyclic, bicyclic or spirocyclic nitrogen-containing ring system that contains 0-3 (preferably 0-1) additional heteroatoms selected from oxygen (O), nitrogen (N), and sulfur (S), and which may be further substituted with one or more groups selected from halogen, C≡N, CF$_3$, OH, C$_1$-C$_4$ alkyl or C$_2$-C$_4$ alkenyl, C$_3$-C$_6$ cycloalkyl, alkoxy, nitro, amino, C$_1$-C$_4$ alkoxycarbonyl, acyl, C$_1$-C$_4$ alkylamino, oxo, SO$_2$CH$_3$, aryl, aralkyl, heterocyclyl, heteroaryl or heteroarylalkyl;

with the proviso that when X is Cl and Z is SO$_2$$R^1$, $R^1$ is not C$_3$ alkyl, C$_4$ alkyl or C$_5$-C$_6$ cycloalkyl;

or when X is Cl and Z is SO$_2$NR$^2$R$^3$, $R^2$ and $R^3$ do not together form an unsubstituted, 1-pyrrolidinyl ring.

An additional embodiment of the above includes the proviso that when X is F and Z is SO$_2$$R^1$, $R^1$ is not pyridyl, cyclopentyl and phenyl substituted with fluoro, or trifluoromethyl.

A second additional embodiment of the above further includes the proviso that when X is Cl and Z is SO$_2$$R^1$, $R^1$ is not thiazolyl, pyridyl, pyridyl-N-oxide, and phenyl substituted with one or two groups selected from fluoro, chloro, methyl, trifluoromethyl, phenyl and tert-butyl.

In a specific embodiment, $R^1$ is ethyl, 2-propanyl, 2-methylpropyl, octyl, 3-cyclopropylpropyl, 4-methylbenzyl, 2-(4-methylphenyl)ethyl, cyclopentyl, cyclohexyl, 3-methylphenyl, 4-methylphenyl, 2,4-dimethylphenyl, 3,4-dimethylphenyl, 3,5-dimethylphenyl, 2-trifluoromethylphenyl, 3-trifluoromethylphenyl, 4-trifluoromethylphenyl, 4-tert-butylphenyl, 3-chlorophenyl, 4-chlorophenyl, 4-fluorophenyl, 3,5-dichlorophenyl, 3,4-dichlorophenyl, 4-fluoro-2-methylphenyl, 3-(quinolin-5-yl)phenyl, biphenyl-3-yl, 3'-chloro-4'-fluorobiphenyl-3-yl, 3-(1H-indazol-4yl)phenyl, 3-(pyridin-4-yl)phenyl, 2-naphthyl, 2-pyridinyl, 3-pyridinyl, 4-pyridinyl, 3-methylpyridin-4-yl, 1-(2,3-dimethylphenyl)pyridin-4-yl, 4-piperidinyl, 1-(2,3-dichlorobenzoyl)piperidin-4-yl, (4-fluorobenzyl)piperidin-4-yl, 1-(4-fluorophenyl)-piperidin-4-yl, 1-(2,3-dichlorobenzyl)piperidin-4-yl, 1-(2-chlorobenzyl)-1H-benzimidazol-4-yl, tetrahydro-2H-pyran-4-yl.

The group X in formula I, in selected embodiments of the sulfonylquinolinol derivatives, is selected from hydrogen, halogen, methyl, trifluoromethyl, and nitrile (C≡N); in further embodiments X in formula I is hydrogen, halogen or methyl; in further embodiments of this group, said halogen is fluorine or chlorine. In one embodiment, X is fluorine. In another embodiment, X is hydrogen. In a further embodiment, X is trifluoromethyl.

In a fourth aspect, the invention provides a method of inhibiting COMT enzyme in a subject by administering compounds according to formula II. These methods comprise administering to a subject in need thereof an effective amount of a COMT-inhibiting sulfonylquinolinol derivatives in accordance with formula II, or a pharmaceutically acceptable salt thereof:

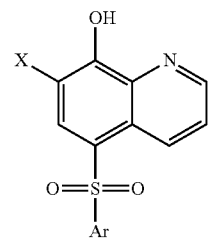

wherein:

X is selected from hydrogen, halogen, C≡N, CF$_3$, and C$_1$-C$_4$ alkyl;

Ar is aryl or heteroaryl, optionally substituted with one or more groups selected from halogen, C≡N, CF$_3$, OH, C$_1$-C$_4$ alkyl or C$_2$-C$_4$ alkenyl, alkoxy, nitro, amino, C$_1$-C$_4$ alkylamino, oxo, C$_3$-C$_{10}$ cycloalkyl, acyl, aryl, aralkyl, heterocyclyl, heteroaryl, CON($R^4$)$_2$, SO$_2$$R^4$, or SO$_2$N($R^4$)$_2$, where each $R^4$ is independently C$_1$-C$_4$ alkyl or ($R^4$)$_2$ forms a carbocyclic ring.

In particular embodiments, Ar is heteroaryl, optionally substituted with one or more groups selected from halogen, C≡N, CF$_3$, OH, C$_1$-C$_4$ alkyl or C$_2$-C$_4$ alkenyl, alkoxy, nitro, amino, C$_1$-C$_4$ alkylamino, oxo, C$_3$-C$_{10}$ cycloalkyl, acyl, aryl, aralkyl, heterocyclyl, heteroaryl, CON($R^4$)$_2$, SO$_2$$R^4$, or SO$_2$N($R^4$)$_2$, where each $R^4$ is independently C$_1$-C$_4$ alkyl or ($R^4$)$_2$ forms a carbocyclic ring.

In more particular embodiments, Ar is heteroaryl selected from the following moieties (arrow indicates point of attachment):

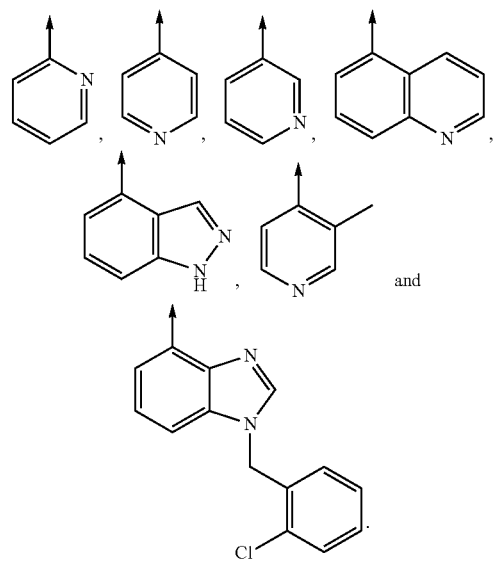

In other particular embodiments, Ar is aryl, optionally substituted with one or more groups selected from halogen, C≡N, CF$_3$, OH, C$_1$-C$_4$ alkyl or C$_2$-C$_4$ alkenyl, alkoxy, nitro, amino, C$_1$-C$_4$ alkylamino, oxo, C$_3$-C$_{10}$ cycloalkyl, acyl, aryl, aralkyl, heterocyclyl, heteroaryl, CON($R^4$)$_2$, SO$_2$$R^4$, or SO$_2$N($R^4$)$_2$, where each $R^4$ is independently C$_1$-C$_4$ alkyl or ($R^4$)$_2$ forms a carbocyclic ring.

In still other particular embodiments, Ar is phenyl, optionally substituted with one or more groups selected from halogen, C≡N, CF$_3$, OH, C$_1$-C$_4$ alkyl or C$_2$-C$_4$ alkenyl, alkoxy, nitro, amino, $C_1$-$C_4$ alkylamino, oxo, $C_3$-$C_{10}$ cycloalkyl, acyl, aryl, aralkyl, heterocyclyl, heteroaryl, CON$(R^4)_2$, $SO_2R^4$, or $SO_2N(R^4)_2$, where each $R^4$ is independently $C_1$-$C_4$ alkyl or $(R^4)_2$ forms a carbocyclic ring.

In more particular embodiments, Ar is phenyl optionally substituted with one or more groups selected from halogen, $C_1$-$C_4$ alkyl, alkoxyl or heteroaryl.

In further particular embodiments, Ar is selected from the following moieties (arrow indicates point of attachment):

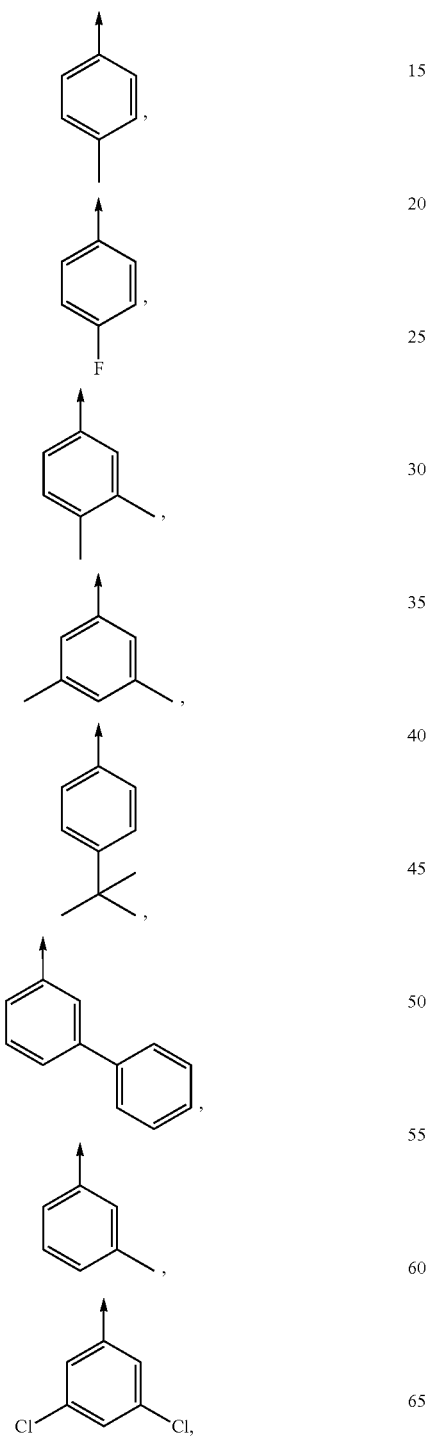

-continued

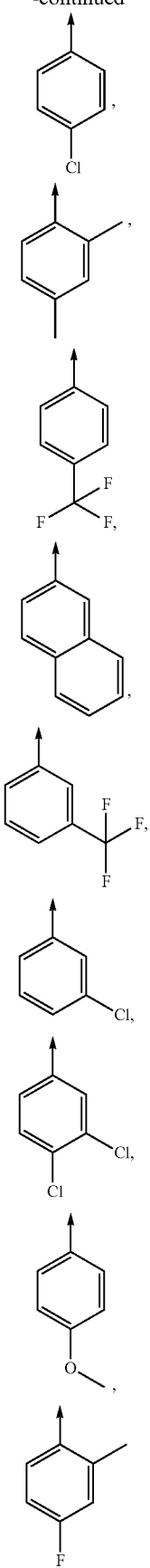

In particular embodiments, $R^1$ is selected from the following moieties (arrow indicates point of attachment):

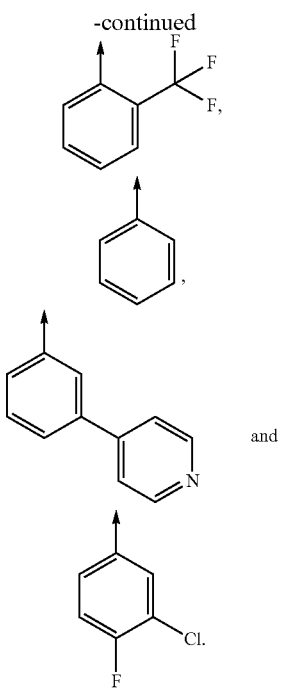

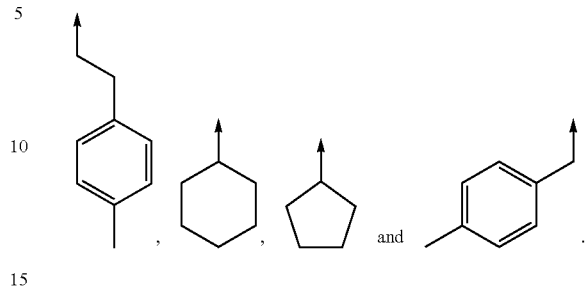

The group X in formula II, in selected embodiments of the sulfonylquinolinol derivatives, is selected from hydrogen, halogen, methyl, trifluoromethyl, and nitrile (C≡N); in further embodiments X in formula I is hydrogen, halogen or methyl; in further embodiments of this group, said halogen is fluorine or chlorine. In one embodiment, X is fluorine. In another embodiment, X is hydrogen. In a further embodiment, X is trifluoromethyl.

In a fifth aspect, the invention provides a method of inhibiting COMT enzyme in a subject by administering compounds according to formula III. These methods comprise administering to a subject in need thereof an effective amount of a COMT-inhibiting sulfonylquinolinol derivative in accordance with formula III, or a pharmaceutically acceptable salt thereof:

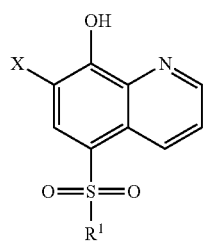

III wherein:
X is selected from hydrogen, F, Br, I, C≡N, $CF_3$, and $C_1$-$C_4$ alkyl; and
$R^1$ is selected from $C_3$-$C_{10}$ cycloalkyl, aryl, aralkyl, heteroaryl and heteroarylalkyl, any of which may be substituted with one or more groups selected from halogen, C≡N, $CF_3$, OH, $C_1$-$C_4$ alkyl or $C_2$-$C_4$ alkenyl, alkoxy, nitro, amino, $C_1$-$C_4$ alkylamino, oxo, $C_3$-$C_{10}$ cycloalkyl, acyl, aryl, aralkyl, heterocyclyl, heteroaryl, $CON(R^4)_2$, $SO_2R^4$, or $SO_2N(R^4)_2$, where each $R^4$ is independently $C_1$-$C_4$ alkyl or $(R^4)_2$ forms a carbocyclic ring.

The group X in formula III, in selected embodiments of the sulfonylquinolinol derivatives, is selected from hydrogen, halogen, methyl, trifluoromethyl, and nitrile (C≡N); in further embodiments X in formula I is hydrogen, halogen or methyl; in further embodiments of this group, said halogen is fluorine or chlorine. In one embodiment, X is fluorine. In another embodiment, X is hydrogen. In a further embodiment, X is trifluoromethyl.

In a sixth aspect, the invention provides a method of inhibiting COMT enzyme in a subject by administering compounds according to formula IV. These methods comprise administering to a subject in need thereof an effective amount of a COMT-inhibiting sulfonylquinolinol derivative in accordance with formula IV, or a pharmaceutically acceptable salt thereof:

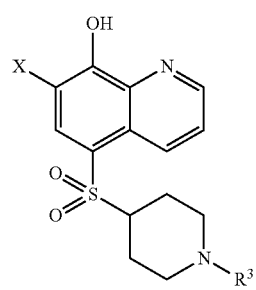

IV wherein:
X is selected from hydrogen, halogen, C≡N, $CF_3$, trifluoromethyl, and $C_1$-$C_4$ alkyl; and
$R^3$ is selected from hydrogen, $C_1$-$C_{10}$ alkyl, $C_3$-$C_{10}$ cycloalkyl, aryl, aralkyl, heterocyclyl, heteroaryl, heteroarylalkyl or acyl, any of which may be substituted with one or more groups selected from halogen, C≡N, $CF_3$, OH, $C_1$-$C_4$ alkyl or $C_2$-$C_4$ alkenyl, alkoxy, nitro, amino, $C_1$-$C_4$ alkylamino, oxo, $C_3$-$C_{10}$ cycloalkyl, acyl, aryl, aralkyl, heterocyclyl, heteroaryl, $CON(R^4)_2$, $SO_2R^4$, or $SO_2N(R^4)_2$, where each $R^4$ is independently $C_1$-$C_4$ alkyl or $(R^4)_2$ forms a carbocyclic ring.

In more particular embodiments, X is hydrogen and $R^3$ is selected from aralkyl, acyl, or aryl.

In further particular embodiments, $R^3$ is selected from the following moieties (arrow indicates point of attachment):

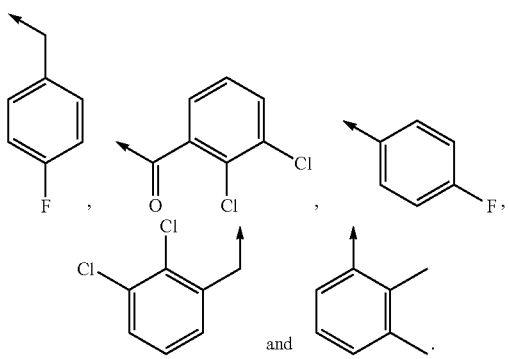

and

Specific sulfonylquinolinol derivatives of the present invention are those selected from the group consisting of:
5-tosylquinolin-8-ol;
5-(4-fluorophenyl)sulfonylquinolin-8-ol;
5-(3,4-dimethylphenyl)sulfonylquinolin-8-ol;
5-(3,5-dimethylphenyl)sulfonylquinolin-8-ol;
5-(4-tert-butylphenyl)sulfonylquinolin-8-ol;
5-phenylphenyl)sulfonylquinolin-8-ol;
5-(m-tolylsulfonyl)quinolin-8-ol;
5-(3,5-dichlorophenyl)sulfonylquinolin-8-ol;
5-(4-chlorophenyl)sulfonylquinolin-8-ol;
5-(2,4-dimethylphenyl)sulfonylquinolin-8-ol;
5-[4-(trifluoromethyl)phenyl]sulfonylquinolin-8-ol;
5-(2-naphthylsulfonyl)quinolin-8-ol;
5-[3-(trifluoromethyl)phenyl]sulfonylquinolin-8-ol;
5-(3-chlorophenyl)sulfonylquinolin-8-ol;
5-(3,4-dichlorophenyl)sulfonylquinolin-8-ol;
5-(2-pyridylsulfonyl)quinolin-8-ol;
5-(4-pyridylsulfonyl)quinolin-8-ol;
5-(4-methoxyphenyl)sulfonylquinolin-8-ol;
5-(3-pyridylsulfonyl)quinolin-8-ol;
5-(4-fluoro-2-methyl-phenyl)sulfonylquinolin-8-ol;
5-[2-(trifluoromethyl)phenyl]sulfonylquinolin-8-ol;
5-(benzenesulfonyl)quinolin-8-ol;
5-[3-(4-pyridyl)phenyl]sulfonylquinolin-8-ol;
5-[3-(3-chloro-4-fluoro-phenyl)phenyl]sulfonylquinolin-8-ol;
5-[3-(5-quinolyl)phenyl]sulfonylquinolin-8-ol;
5-[3-(1H-indazol-4-yl)phenyl]sulfonylquinolin-8-ol;
5-[(3-methyl-4-pyridyl)sulfonyl]quinolin-8-ol;
5-[1-[(2-chlorophenyl)methyl]benzimidazol-4-yl]sulfonylquinolin-8-ol;
5-[2-(p-tolyl)ethylsulfonyl]quinolin-8-ol;
5-cyclohexylsulfonylquinolin-8-ol;
5-cyclopentylsulfonylquinolin-8-ol;
5-(p-tolylmethylsulfonyl)quinolin-8-ol;
5-ethyl sulfonylquinolin-8-ol;
5-(4-piperidylsulfonyl)quinolin-8-ol;
5-[[1-[(4-fluorophenyl)methyl]-4-piperidyl]sulfonyl]quinolin-8-ol;
5-[[1-[(2,3-dichlorophenyl)methyl]-4-piperidyl]sulfonyl]quinolin-8-ol;
5-[[1-(4-fluorophenyl)-4-piperidyl]sulfonyl]quinolin-8-ol;
5-[[1-(2,3-dimethylphenyl)-4-piperidyl]sulfonyl]quinolin-8-ol;
7-iodo-5-(p-tolylsulfonyl)quinolin-8-ol;
7-bromo-5-(p-tolylsulfonyl)quinolin-8-ol;
7-chloro-5-(p-tolylsulfonyl)quinolin-8-ol;
7-fluoro-5-(p-tolylsulfonyl)quinolin-8-ol;
5-(p-tolylsulfonyl)-7-(trifluoromethyl)quinolin-8-ol; and
5-cyclopentyl sulfonyl-7-(trifluoromethyl)quinolin-8-ol.

In a seventh aspect, the invention provides a method of inhibiting COMT enzyme in a subject by administering compounds according to formula I. These methods comprise administering to a subject in need thereof an effective amount of a COMT-inhibiting hydroxyquinoline sulfonamide derivative in accordance with formula I, or a pharmaceutically acceptable salt thereof:

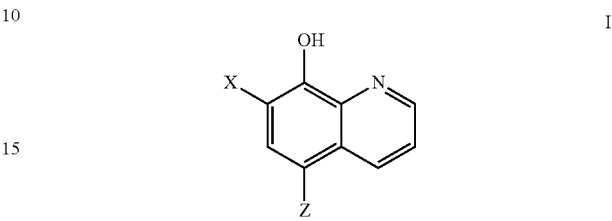

I wherein:
X is selected from hydrogen, halogen, C≡N, $CF_3$, and $C_1$-$C_4$ alkyl;
Z is $SO_2NR^2R^3$, wherein $NR^2R^3$ is a 1-pyrrolidinyl, 1-piperidinyl, 1-piperazinyl, 1-azetidinyl, 1,3,8-triazaspiro[4.5]dec-8-yl, 3,4-dihydro-2(1H)-isoquinolinyl, 1,3-dihydro-2H-isoindol-2-yl, 4-morpholinyl, 5,8-dihydronaphthyridin-7(6H)-yl, azabicyclo[3.2.2]non-3-yl which may be further substituted with one or more groups selected from halogen, C≡N, $CF_3$, OH, $C_1$-$C_4$ alkyl or $C_2$-$C_4$ alkenyl, $C_3$-$C_6$ cycloalkyl, $C_1$-$C_4$ alkoxy, arylalkoxy, nitro, amino, $C_1$-$C_4$ alkoxycarbonyl, acyl, $C_1$-$C_4$ alkylamino, oxo, $SO_2CH_3$, aryl, aralkyl, heterocyclyl, or heteroaryl;
with the proviso that when X is H, $R^2$ and $R^3$ do not together form a 1-piperidinyl ring substituted with a α-methyl group;
or when X is Cl, $R^2$ and $R^3$ do not together form an unsubstituted, 1-pyrrolidinyl ring.

In yet another particular embodiment, the present method comprises administering to a subject in need thereof an effective amount of a compound of formula I, or a pharmaceutically acceptable salt thereof, wherein $NR^2R^3$ is selected from 1-pyrrolidinyl, 2-methylpyrrolidin-1-yl, (2R)-2-methylpyrrolidin-1-yl, (2S)-2-methylpyrrolidin-1-yl, (3R,4R)-3,4-difluoropyrrolidin-1-yl, 2-(propan-2-yl)pyrrolidin-1-yl, 2-(2-methylpropyl)pyrrolidin-1-yl, 2-cyclohexylpyrrolidin-1-yl, 2-benzylpyrrolidin-1-yl, 2-phenylpyrrolidin-1-yl, 2-(2-methylphenyl)pyrrolidin-1-yl, 2-(4-fluorophenyl)pyrrolidin-1-yl, 3-(4-fluorophenyl)pyrrolidin-1-yl, 2-(4-methoxyphenyl)pyrrolidin-1-yl, 2-[2-(trifluoromethyl)phenyl]pyrrolidin-1-yl, 2-(pyridin-2-yl)pyrrolidin-1-yl, 2-(pyridin-3-yl)pyrrolidin-1-yl, 2-(pyridin-4-yl)pyrrolidin-1-yl, 1-piperidinyl, 2-phenylpiperidin-1-yl, 3-phenylpiperidin-1-yl, 4-phenylpiperidin-1-yl, 4-hydroxy-4-phenylpiperidin-1-yl, 4-acetyl-4-phenylpiperidin-1-yl, 4-benzylpiperidin-1-yl, 4-benzoylpiperidin-1-yl, 1-piperazinyl, 2-methylpiperazin-1-yl, 4-methylpiperazin-1-yl, 4-phenylpiperazin-1-yl, 4-(2, 3-dimethylphenyl)piperazin-1-yl, 4-(2, 5-dimethylphenyl)piperazin-1-yl, 4-(4-fluorophenyl)piperazin-1-yl, 4-(2,3-dichlorophenyl)piperazin-1-yl, 4-[4-(trifluoromethyl)phenyl]piperazin-1-yl, 4-(2-cyanophenyl)piperazin-1-yl, 4-(biphenyl-2-yl)piperazin-1-yl, 4-benzylpiperazin-1-yl, 4-(4-fluorobenzyl)piperazin-1-yl, 4-(3-methoxypropyl)piperazin-1-yl, 4-(methoxycarbonyl)piperazin-1-yl, 4-(tert-butoxycarbonyl)piperazin-1-yl, 4-(tert-butoxycarbonyl)-2-methylpiperazin-1-yl, 4-(5-chloropyridin-2-yl)piperazin-1-yl, 4-[bis(4-fluorophenyl)

methyl]piperazin-1-yl, 4-(1,2-benzothiazol-3-yl)piperazin-1-yl, 3,4-dihydroisoquinolin-2(1H)-yl, 1,3-dihydro-2H-isoindol-2-yl, 5,8-dihydro-1,7-naphthyridin-7(6H)-yl, 4-oxo-1-phenyl-1,3,8-triazaspiro[4.5]dec-8-yl or 3-azabicyclo[3.2.2]non-3-yl, 3-[4-(trifluoromethoxy)phenoxy]azetidin-1-yl.

The present method comprises administering to a subject in need thereof an effective amount of a compound of formula I, or a pharmaceutically acceptable salt thereof, wherein X is selected from hydrogen, halogen, and nitrile (C≡N); in further embodiments X in formula I is hydrogen, halogen or methyl; in further embodiments of this group, said halogen is fluorine or chlorine. In one embodiment, X is fluorine. In another embodiment, X is hydrogen.

In an eighth aspect, the invention provides a method of inhibiting COMT enzyme in a subject by administering compounds according to formula V. These methods comprise administering to a subject in need thereof an effective amount of a COMT-inhibiting hydroxyquinoline sulfonamide derivative in accordance with formula V, or a pharmaceutically acceptable salt thereof:

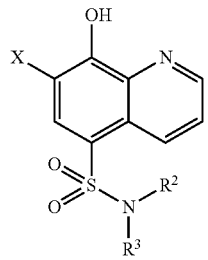

V wherein:
X is selected from hydrogen, halogen, C≡N, CF$_3$, and C$_1$-C$_4$ alkyl;
R$^2$ and R$^3$ are independently selected from hydrogen, C$_1$-C$_{10}$ alkyl, C$_3$-C$_{10}$ cycloalkyl, aryl, aralkyl, heterocyclyl, heteroaryl and heteroarylalkyl, any of which may be substituted with one or more groups selected from halogen, C≡N, CF$_3$, OH, C$_1$-C$_4$ alkyl or C$_2$-C$_4$ alkenyl, alkoxy, nitro, amino, C$_1$-C$_4$ alkylamino, oxo, C$_3$-C$_{10}$ cycloalkyl, acyl, aryl, aralkyl, heterocyclyl, heteroaryl, CON(R$^4$)$_2$, SO$_2$R$^4$, or SO$_2$N(R$^4$)$_2$, where each R$^4$ is independently C$_1$-C$_4$ alkyl or (R$^4$)$_2$ forms a carbocyclic ring.

In particular embodiments, NR$^2$R$^3$ is selected from the following moieties (arrow indicates point of attachment):

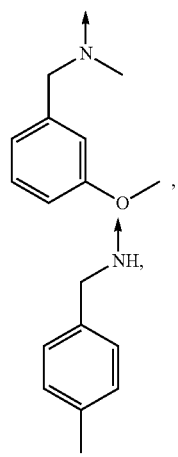

-continued

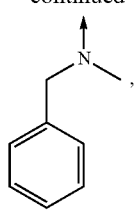

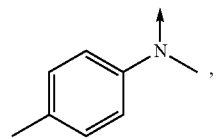

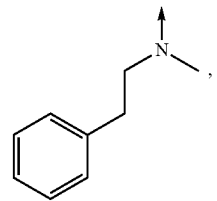

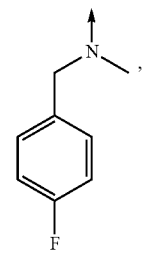

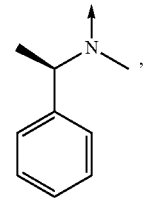

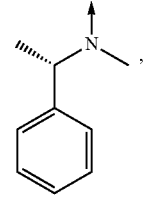

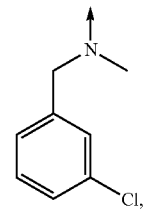

23
-continued

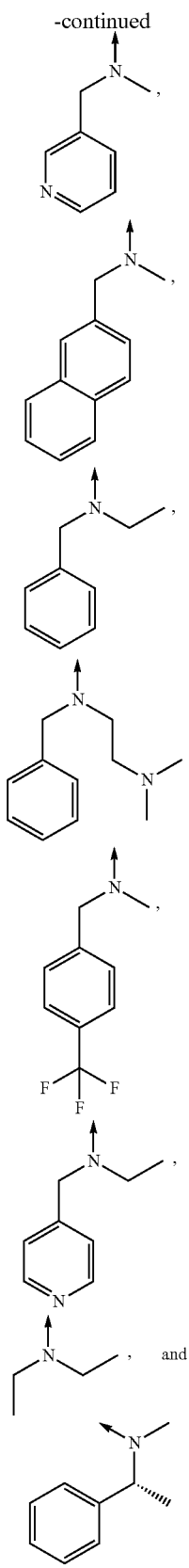

In a ninth aspect, the invention provides a method of inhibiting COMT enzyme in a subject by administering compounds according to formula VI. These methods com-

24 prise administering to a subject in need thereof an effective amount of a COMT-inhibiting hydroxyquinoline sulfonamide derivative in accordance with formula VI, or a pharmaceutically acceptable salt thereof:

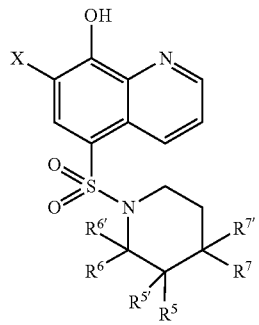

VI wherein:

X is selected from hydrogen, halogen, C≡N, $CF_3$, and $C_1$-$C_4$ alkyl;

$R^5$, $R^{5'}$, $R^6$, $R^{6'}$, $R^7$ and $R^{7'}$ are each independently selected from hydrogen, halogen, hydroxyl, C≡N, $CF_3$, OH, $C_1$-$C_4$ alkyl or $C_2$-$C_4$ alkenyl, $C_3$-$C_6$ cycloalkyl, alkoxy, nitro, amino, $C_1$-$C_4$ alkoxycarbonyl, acyl, $C_1$-$C_4$ alkylamino, oxo, $SO_2CH_3$, aryl, aralkyl, heterocyclyl, heteroaryl or heteroarylalkyl, or two of $R^5$, $R^{5'}$, $R^6$, $R^{6'}$, $R^7$ and $R^{7'}$ come together to form an aliphatic or aromatic ring; with the proviso that when X is H, neither $R^6$ nor $R^{6'}$ are a methyl group.

In particular embodiments, the piperidine with $R^5$, $R^{5'}$, $R^6$, $R^{6'}$, $R^7$ and $R^{7'}$ substitution is selected from the following moieties (arrow indicates point of attachment):

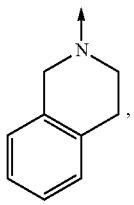

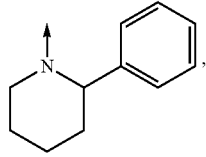

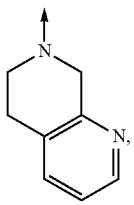

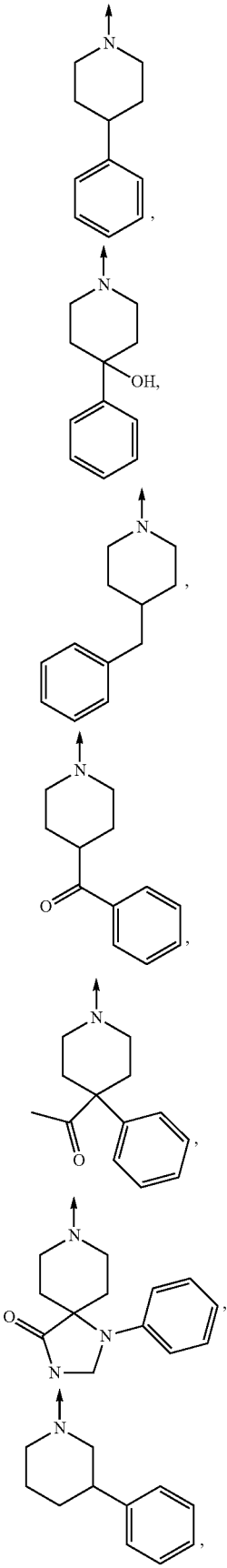

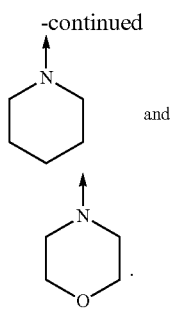

and

In a tenth aspect, the invention provides a method of inhibiting COMT enzyme in a subject by administering compounds according to formula VII. These methods comprise administering to a subject in need thereof an effective amount of a COMT-inhibiting hydroxyquinoline sulfonamide derivatives in accordance with formula VII, or a pharmaceutically acceptable salt thereof:

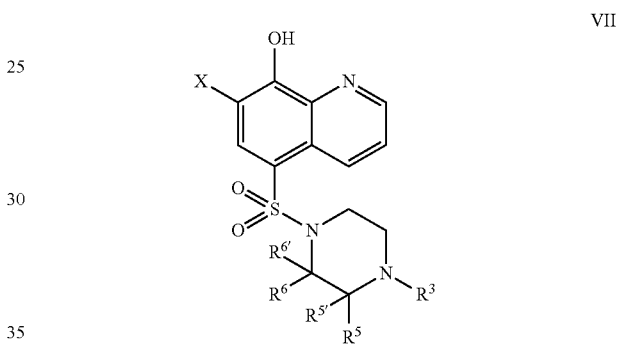

VII wherein:

X is selected from hydrogen, halogen, C≡N, CF$_3$, and C$_1$-C$_4$ alkyl;

R$^3$, R$^5$, R$^{5'}$, R$^6$ and R$^{6'}$ are each independently selected from hydrogen, halogen, hydroxyl, C≡N, CF$_3$, OH, C$_1$-C$_4$ alkyl or C$_2$-C$_4$ alkenyl, C$_3$-C$_6$ cycloalkyl, alkoxy, nitro, amino, C$_1$-C$_4$ alkoxycarbonyl, acyl, C$_1$-C$_4$ alkylamino, oxo, SO$_2$CH$_3$, aryl, aralkyl, heterocyclyl, heteroaryl or heteroarylalkyl, or two of R$^3$, R$^5$, R$^{5'}$, R$^6$ or R$^{6'}$ come together to form an aliphatic or aromatic ring.

In particular embodiments, R$^5$, R$^{5'}$, R$^6$ and R$^{6'}$ are each hydrogen.

In other particular embodiments, the piperizine with R$^3$, R$^5$, R$^{5'}$, R$^6$ and R$^{6'}$ substitution is selected from the following moieties (arrow indicates point of attachment):

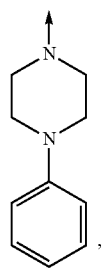

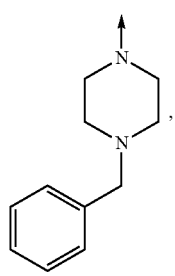
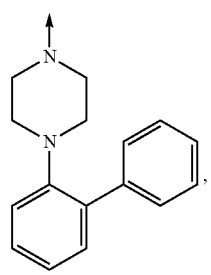
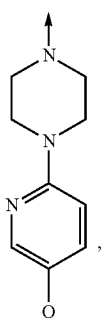
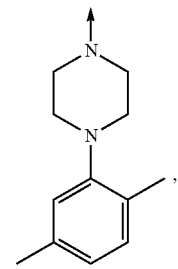
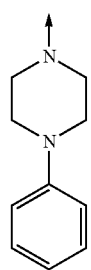
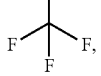
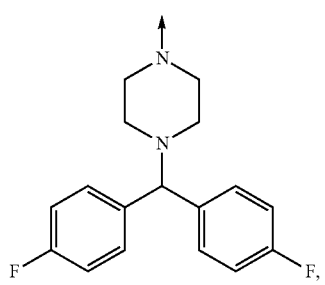
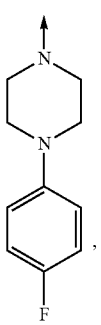

-continued

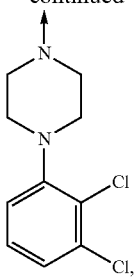

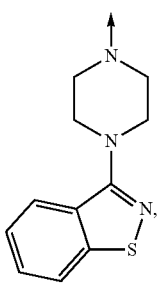

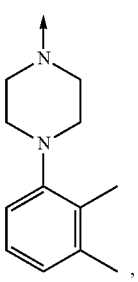

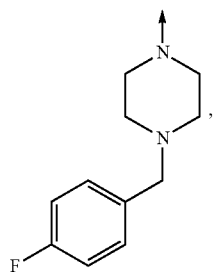

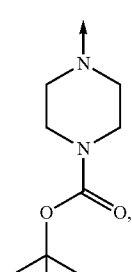

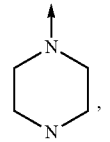

-continued

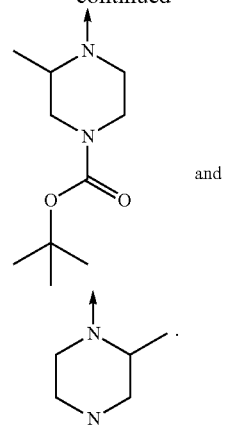

and

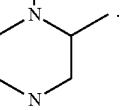

In an eleventh aspect, the invention provides a method of inhibiting COMT enzyme in a subject by administering compounds according to formula VIII. These methods comprise administering to a subject in need thereof an effective amount of a COMT-inhibiting hydroxyquinoline sulfonamide derivatives in accordance with formula VIII, or a pharmaceutically acceptable salt thereof:

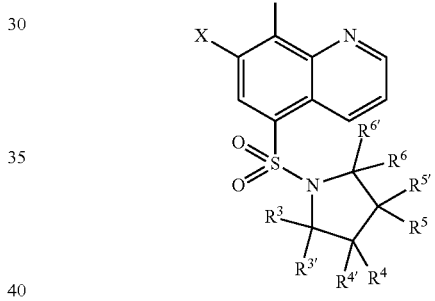

VIII wherein:

X is selected from hydrogen, halogen, C≡N, $CF_3$, and $C_1$-$C_4$ alkyl;

$R^3$, $R^{3'}$, $R^4$, $R^{4'}$, $R^5$, $R^{5'}$, $R^6$ and $R^{6'}$ are each independently selected from hydrogen, halogen, hydroxyl, C≡N, $CF_3$, OH, $C_1$-$C_4$ alkyl or $C_2$-$C_4$ alkenyl, $C_3$-$C_6$ cycloalkyl, alkoxy, nitro, amino, $C_1$-$C_4$ alkoxycarbonyl, acyl, $C_1$-$C_4$ alkylamino, oxo, $SO_2CH_3$, aryl, aralkyl, heterocyclyl, heteroaryl or heteroarylalkyl, or two of $R^3$, $R^{3'}$, $R^4$, $R^{4'}$, $R^5$, $R^{5'}$, $R^6$ or $R^{6'}$ come together to form an aliphatic or aromatic ring; with the proviso that when X is Cl, all of $R^3$, $R^{3'}$, $R^4$, $R^{4'}$, $R^5$, $R^{5'}$, $R^6$ and $R^{6'}$ are not hydrogen; or when X is hydrogen, none of $R^3$, $R^{3'}$, $R^6$ and $R^{6'}$ are methyl.

In particular embodiments, all but one of $R^3$, $R^{3'}$, $R^4$, $R^{4'}$, $R^5$, $R^{5'}$, $R^6$ and $R^{6'}$ is hydrogen.

In other particular embodiments, $R^3$, $R^{3'}$, $R^6$ or $R^{6'}$ are aryl or heteroaryl, optionally substituted with one or more groups selected from halogen, $C_1$-$C_4$ alkyl, alkyoxyl and haloalkyl.

In still other particular embodiments, $R^3$, $R^{3'}$, $R^6$ or $R^{6'}$ are heteroaryl, preferably pyridine.

In further embodiments, $R^3$, $R^{3'}$, $R^6$ or $R^{6'}$ are $C_1$-$C_4$ alkyl or cycloalkyl.

In more particular embodiments, the pyrrolidine with $R^3$, $R^{3'}$, $R^4$, $R^{4'}$, $R^5$, $R^{5'}$, $R^6$ and $R^{6'}$ substitution is selected from the following moieties (arrow indicates point of attachment):

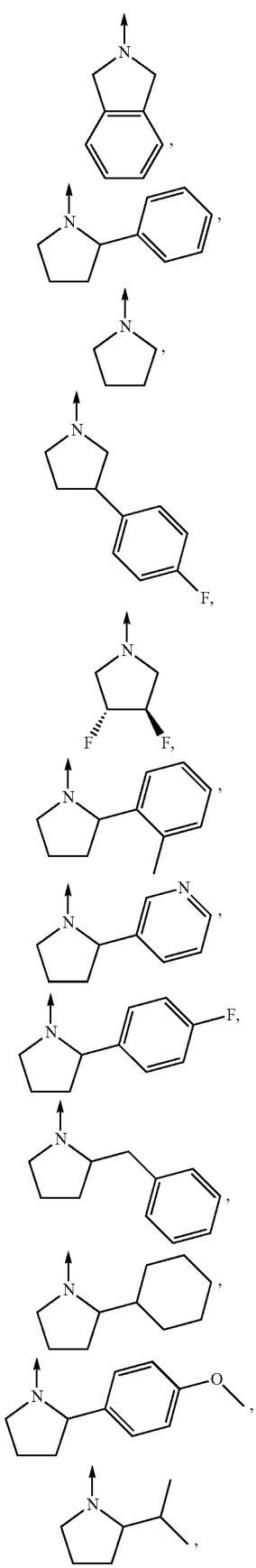

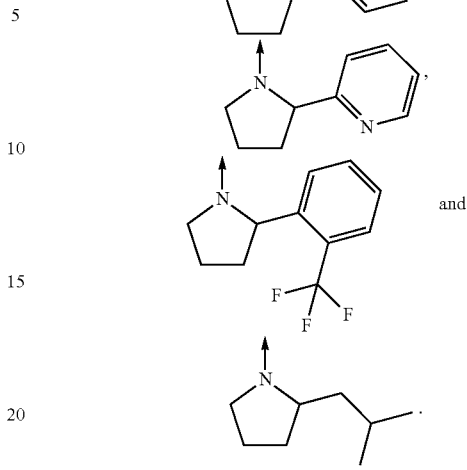

and

Specific hydroxyquinoline sulfonamide derivatives for use in the methods described herein are selected from the group consisting of:
5-(3,4-dihydro-1H-isoquinolin-2-ylsulfonyl)quinolin-8-ol;
5-(4-phenylpiperazin-1-yl)sulfonylquinolin-8-ol;
5-(4-benzylpiperazin-1-yl)sulfonylquinolin-8-ol;
5-isoindolin-2-ylsulfonylquinolin-8-ol;
5-(2-phenylpyrrolidin-1-yl)sulfonylquinolin-8-ol;
5-pyrrolidin-1-ylsulfonylquinolin-8-ol;
5-(4-methylpiperazin-1-yl)sulfonylquinolin-8-ol;
5-[(2-phenyl-1-piperidyl)sulfonyl]quinolin-8-ol;
5-(3-(4-fluorophenyl)pyrrolidin-1-yl)sulfonylquinolin-8-ol;
5-(6,8-dihydro-5H-1,7-naphthyridin-7-ylsulfonyl)quinolin-8-ol;
5-[4-(5-chloro-2-pyridyl)piperazin-1-yl]sulfonylquinolin-8-ol;
5-[(3R,4R)-3,4-difluoropyrrolidin-1-yl]sulfonylquinolin-8-ol;
5-[2-(o-tolyl)pyrrolidin-1-yl]sulfonylquinolin-8-ol;
5-[2-(3-pyridyl)pyrrolidin-1-yl]sulfonylquinolin-8-ol;
5-[(4-phenyl-1-piperidyl)sulfonyl]quinolin-8-ol;
5-[2-(4-fluorophenyl)pyrrolidin-1-yl]sulfonylquinolin-8-ol;
5-(2-benzylpyrrolidin-1-yl)sulfonylquinolin-8-ol;
5-(2-cyclohexylpyrrolidin-1-yl)sulfonylquinolin-8-ol;
5-[2-(4-methoxyphenyl)pyrrolidin-1-yl]sulfonylquinolin-8-ol;
5-(2-isopropylpyrrolidin-1-yl)sulfonylquinolin-8-ol;
5-[2-(4-pyridyl)pyrrolidin-1-yl]sulfonylquinolin-8-ol;
5-[2-(2-pyridyl)pyrrolidin-1-yl]sulfonylquinolin-8-ol;
5-[2-[2-(trifluoromethyl)phenyl]pyrrolidin-1-yl]sulfonylquinolin-8-ol;
5-(2-isobutylpyrrolidin-1-yl)sulfonylquinolin-8-ol;
5-[(4-hydroxy-4-phenyl-1-piperidyl)sulfonyl]quinolin-8-ol;
5-[(4-benzyl-1-piperidyl)sulfonyl]quinolin-8-ol;
[1-[(8-hydroxy-5-quinolyl)sulfonyl]-4-piperidyl]-phenyl-methanone;
1-[1-[(8-hydroxy-5-quinolyl)sulfonyl]-4-phenyl-4-piperidyl]ethanone;
8-[(8-hydroxy-5-quinolyl)sulfonyl]-1-phenyl-1,3,8-triazaspiro[4.5]decan-4-one;
methyl 4-[(8-hydroxy-5-quinolyl)sulfonyl]piperazine-1-carboxylate;

5-[4-(3-methoxypropyl)piperazin-1-yl]sulfonylquinolin-8-ol;
2-[4-[(8-hydroxy-5-quinolyl)sulfonyl]piperazin-1-yl]benzonitrile;
5-(3-azabicyclo[3.2.2]nonan-3-ylsulfonyl)quinolin-8-ol;
5-[4-(2-phenylphenyl)piperazin-1-yl]sulfonylquinolin-8-ol;
5-[4-(2, 5-dimethylphenyl)piperazin-1-yl]sulfonylquinolin-8-ol;
5-[4-[4-(trifluoromethyl)phenyl]piperazin-1-yl]sulfonylquinolin-8-ol;
5-[4-[bis(4-fluorophenyl)methyl]piperazin-1-yl]sulfonylquinolin-8-ol;
5-[4-(4-fluorophenyl)piperazin-1-yl]sulfonylquinolin-8-ol;
5-[4-(2,3-dichlorophenyl)piperazin-1-yl]sulfonylquinolin-8-ol;
5-[4-(1,2-benzothiazol-3-yl)piperazin-1-yl]sulfonylquinolin-8-ol;
5-[3-[4-(trifluoromethoxy)phenoxy]azetidin-1-yl]sulfonylquinolin-8-ol;
5-[4-(2,3-dimethylphenyl)piperazin-1-yl]sulfonylquinolin-8-ol;
5-[4-[(4-fluorophenyl)methyl]piperazin-1-yl]sulfonylquinolin-8-ol;
5-[(3-phenyl-1-piperidyl)sulfonyl]quinolin-8-ol;
tert-butyl 4-[(8-hydroxy-5-quinolyl)sulfonyl]piperazine-1-carboxylate;
5-piperazin-1-ylsulfonylquinolin-8-ol;
tert-butyl 4-[(8-hydroxy-5-quinolyl)sulfonyl]-3-methyl-piperazine-1-carboxylate;
5-(2-methylpiperazin-1-yl)sulfonylquinolin-8-ol;
7-methyl-5-pyrrolidin-1-yl sulfonyl-quinolin-8-ol;
7-chloro-5-[4-[(4-fluorophenyl)methyl]piperazin-1-yl]sulfonyl-quinolin-8-ol;
7-fluoro-5-[4-[(4-fluorophenyl)methyl]piperazin-1-yl]sulfonyl-quinolin-8-ol;
5-[(2-methylpyrrolidin-1-yl)sulfonyl]quinolin-8-ol;
5-[4-[(4-fluorophenyl)methyl]piperazin-1-yl]sulfonyl-7-methyl-quinolin-8-ol;
5-[(3R,4R)-3,4-difluoropyrrolidin-1-yl]sulfonyl-7-methyl-quinolin-8-ol;
7-chloro-5-[(2S)-2-methylpyrrolidin-1-yl]sulfonyl-quinolin-8-ol;
7-chloro-5-[(2R)-2-methylpyrrolidin-1-yl]sulfonyl-quinolin-8-ol;
7-bromo-5-[4-[(4-fluorophenyl)methyl]piperazin-1-yl]sulfonyl-quinolin-8-ol;
7-fluoro-5-pyrrolidin-1-yl sulfonyl-quinolin-8-ol;
8-hydroxy-N-[(3-methoxyphenyl)methyl]-N-methyl-quinoline-5-sulfonamide;
8-hydroxy-N-(4-methylbenzyl)quinoline-5-sulfonamide;
N-benzyl-8-hydroxy-N-methyl quinoline-5-sulfonamide;
8-hydroxy-N-(4-methylphenyl)-N-methylquinoline-5-sulfonamide;
8-hydroxy-N-methyl-N-phenethyl-quinoline-5-sulfonamide;
N-[(4-fluorophenyl)methyl]-8-hydroxy-N-methyl-quinoline-5-sulfonamide;
8-hydroxy-N-methyl-N-[(1R)-1-phenylethyl]quinoline-5-sulfonamide;
8-hydroxy-N-methyl-N-[(1S)-1-phenyl ethyl]quinoline-5-sulfonamide;
N-[(2-fluorophenyl)methyl]-8-hydroxy-N-methyl-quinoline-5-sulfonamide;
N-[(3-chlorophenyl)methyl]-8-hydroxy-N-methyl-quinoline-5-sulfonamide;
8-hydroxy-N-methyl-N-(3-pyridylmethyl)quinoline-5-sulfonamide;
8-hydroxy-N-methyl-N-(2-naphthylmethyl)quinoline-5-sulfonamide;
N-benzyl-N-ethyl-8-hydroxy-quinoline-5-sulfonamide;
N-benzyl-N-(2-dimethylaminoethyl)-8-hydroxy-quinoline-5-sulfonamide;
5-(piperidin-1-yl)sulfonylquinolin-8-ol;
5-(4-morpholin-1-yl)sulfonylquinolin-8-ol;
N-[(4-(trifluoromethyl)phenyl)methyl]-8-hydroxy-N-methyl-quinoline-5-sulfonamide;
N-ethyl-8-hydroxy-N-(4-pyridylmethyl)quinoline-5-sulfonamide;
N,N-diethyl-8-hydroxy-quinoline-5-sulfonamide;
8-hydroxy-N,7-dimethyl-N-[(1R)-1-phenylethyl]quinoline-5-sulfonamide;
7-chloro-8-hydroxy-N-methyl-N-[(1R)-1-phenylethyl]quinoline-5-sulfonamide;
7-bromo-8-hydroxy-N-methyl-N-[(1R)-1-phenylethyl]quinoline-5-sulfonamide; and
7-fluoro-8-hydroxy-N-methyl-N-[(1R)-1-phenylethyl]quinoline-5-sulfonamide.

The compounds for use in the instant method may be selected from any one or any combination of compounds identified herein, including compounds designated 1-125 herein.

For use in the method, the compound or compounds of the present invention, described above, is typically provided as a pharmaceutical composition wherein the compound or compounds is present in combination with a pharmaceutically acceptable carrier as described herein. Such pharmaceutical compositions are also provided by this disclosure.

For use in the method, the compound(s) of the present invention, described above, may also be used in combination with another additional therapeutic agent.

The methods of the present invention may be used to treat or prevent a neurological or psychiatric disorder. In particular, exemplary embodiments of the invention include methods of treating or preventing schizophrenia, major depression, a depressive phase of bipolar disorder, attention deficit disorder, attention deficit/hyperactivity disorder, substance dependency, or increased appetite associated with smoking cessation or antipsychotic use. Other significant indications include age-associated cognitive symptoms, impulse control disorders, including compulsive gambling, sexual behavior, and other compulsive destructive behaviors.

In addition to the psychiatric indications, the methods of the invention may also be used to treat neurological disorders. In one embodiment, the method of the present invention comprises administering an effective amount of a compound described herein above in combination with L-DOPA for treatment of Parkinson's disease. The compound can be administered in combination with L-DOPA, concurrently or separately, with or without an aromatic L-amino acid decarboxylase inhibitor (AADC) such as carbidopa, to prevent or inhibit COMT-mediated metabolism of L-DOPA.

III. Compounds

Also disclosed herein are the novel sulfonylquinolinol derivatives and novel hydroxyquinoline sulfonamide derivatives described above which, preferably, are inhibitors of catechol O-methyltransferase (COMT) enzyme, and which are useful in the treatment or prevention of neurological or psychiatric disorders or diseases in which COMT is involved. The compounds of the invention are characterized by their activity to inhibit the enzyme COMT. In preferred embodiments, the compounds of the present invention are effective to inhibit the enzyme COMT, in an assay which determines the inhibitory concentration ($IC_{50}$) for the conversion of the methyl donor S-adenosyl methionine to S-adenosyl homocysteine (SAH) as described herein, with a pIC$_{50}$ superior or equal to 4.5. In increasingly preferred embodiments, the pIC$_{50}$ as so determined is superior or equal to 6.0. In a more preferred embodiment, the pIC$_{50}$ as so determined is superior or equal to 7.0.

The ability of compounds within the scope of this invention to inhibit the activity of catechol-O-methyltransferase (COMT) may be determined by methods known to those in the art for measuring COMT inhibition. One method for measuring COMT activity uses a homogeneous time-resolved fluorescent (HTRF) assay (Lina et al, 2012; kit from CisBio, Codolet, France). This assay measures the production of-S-adenosyl homocysteine (SAH) from the methyl donor S-adenosyl methionine. Using this assay preferred preferred compounds of the invention have a pIC$_{50}$ superior or equal to 4.5. In increasingly preferred embodiments, the pIC$_{50}$ as so determined is superior or equal to 6.0. In a more preferred embodiment, the pIC$_{50}$ as so determined is superior or equal to 7.0.

Provided herein are COMT-inhibiting compounds in accordance with formula I, or pharmaceutically acceptable salts thereof:

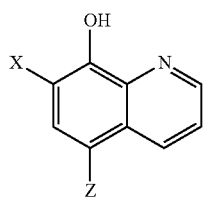

I wherein:
X is selected from hydrogen, halogen, C≡N, CF$_3$, and C$_1$-C$_4$ alkyl;
Z is selected from SO$_2$R$^1$ and SO$_2$NR$^2$R$^3$;
R$^1$ is selected from C$_1$-C$_{10}$ alkyl, C$_3$-C$_{10}$ cycloalkyl, aryl, aralkyl, heterocyclyl, heteroaryl and heteroarylalkyl, any of which may be substituted with one or more groups selected from halogen, C≡N, CF$_3$, OH, C$_1$-C$_4$ alkyl or C$_2$-C$_4$ alkenyl, alkoxy, nitro, amino, C$_1$-C$_4$ alkylamino, oxo, C$_3$-C$_{10}$ cycloalkyl, acyl, aryl, aralkyl, heterocyclyl, heteroaryl, CON(R$^4$)$_2$, SO$_2$R$^4$, or SO$_2$N(R$^4$)$_2$, where each R$^4$ is independently C$_1$-C$_4$ alkyl or (R$^4$)$_2$ forms a carbocyclic ring;
R$^2$ and R$^3$ are independently selected from hydrogen and any of the groups as defined for R$^1$, with the proviso that at least one of R$^2$ or R$^3$ is different from hydrogen; or R$^2$ and R$^3$ may together form a 3-10 membered monocyclic, bicyclic or spirocyclic nitrogen-containing ring system that contains 0-3 (preferably 0-1) additional heteroatoms selected from oxygen (O), nitrogen (N), and sulfur (S), and which may be further substituted with one or more groups selected from halogen, C≡N, CF$_3$, OH, C$_1$-C$_4$ alkyl or C$_2$-C$_4$ alkenyl, C$_3$-C$_6$ cycloalkyl, alkoxy, nitro, amino, C$_1$-C$_4$ alkoxycarbonyl, acyl, C$_1$-C$_4$ alkylamino, oxo, SO$_2$CH$_3$, aryl, aralkyl, heterocyclyl, heteroaryl or heteroarylalkyl;
with the proviso that when X is hydrogen and Z is SO$_2$R$^1$, R$^1$ is not C$_1$ alkyl, C$_4$ alkyl, C$_8$ alkyl, phenyl, 4-methylphenyl, 4-methoxybenzyl, 4-bromophenyl, 4-iodophenyl, 2,4,6-trimethylphenyl, CH(COMe)$_2$, CH(CO$_2$Et)$_2$, 4-BnOPh, tetrahydropyran or propylcyclopropane;
or when X is H and Z is SO$_2$NR$^2$R$^3$, R$^2$ and R$^3$ do not together form a 1-piperidinyl ring substituted with an α-methyl group;
or when X is Cl and Z is SO$_2$R$^1$, R$^1$ is not C$_3$ alkyl, C$_4$ alkyl or C$_5$-C$_6$ cycloalkyl;
or when X is Cl and Z is SO$_2$NR$^2$R$^3$, R$^2$ and R$^3$ do not together form an unsubstituted, 1-pyrrolidinyl ring.

An additional embodiment of the above includes the proviso that when X is F and Z is SO$_2$R$^1$, R$^1$ is not pyridyl, cyclopentyl and phenyl substituted with fluoro, or trifluoromethyl.

A second additional embodiment of the above further includes the proviso that when X is Cl and Z is SO$_2$R$^1$, R$^1$ is not thiazolyl, pyridyl, pyridyl-N-oxide, and phenyl substituted with one or two groups selected from fluoro, chloro, methyl, trifluoromethyl, phenyl and tert-butyl.

In particular embodiments, R$^1$ is selected from C$_1$-C$_{10}$ alkyl, C$_3$-C$_{10}$ cycloalkyl, aryl, aralkyl, heterocyclyl, heteroaryl and heteroarylalkyl, any of which may be substituted with one or more groups selected from halogen, C≡N, CF$_3$, OH, C$_1$-C$_4$ alkyl or alkenyl, C$_1$-C$_4$ alkoxy, aryloxy, nitro, amino, C$_1$-C$_4$ alkylamino, oxo, C$_3$-C$_6$ cycloalkyl, acyl, aryl, aralkyl, heterocyclyl or heteroaryl.

In other particular embodiments, Z is SO$_2$R$^1$ and R$^1$ is selected from substituted or unsubstituted C$_1$-C$_{10}$ alkyl, substituted or unsubstituted C$_3$-C$_{10}$ cycloalkyl, substituted or unsubstituted aryl, substituted or unsubstituted aralkyl, substituted or unsubstituted C-attached heterocyclyl, substituted or unsubstituted C-attached heteroaryl or substituted or unsubstituted heteroarylalkyl.

In still other particular embodiments, Z is SO$_2$R$^1$ and R$^1$ is selected from C$_1$-C$_{10}$ alkyl, C$_3$-C$_{10}$ cycloalkyl, phenyl, naphthyl, aralkyl, C-attached piperidinyl, C-attached 1H-benzimidazolyl, C-attached tetrahydro-2H-pyranyl and pyridinyl, any of which may be substituted with one or more groups selected from halogen, CF$_3$, C$_1$-C$_4$ alkyl, C$_1$-C$_4$ alkoxy, C$_3$-C$_6$ cycloalkyl, substituted or unsubstituted phenyl, substituted or unsubstituted pyridinyl, substituted or unsubstituted quinolinyl, substituted or unsubstituted 1H-indazolyl, substituted or unsubstituted aralkyl or acyl. Certain embodiments include the proviso that when X is fluorine and Z is SO$_2$R$^1$, R$^1$ is not cyclopentyl.

In further particular embodiments, when Z is SO$_2$NR$^2$R$^3$, each of R$^2$ and R$^3$ may be independently selected from hydrogen, C$_1$-C$_{10}$ alkyl, C$_3$-C$_{10}$ cycloalkyl, aryl, aralkyl, heterocyclyl, heteroaryl and heteroarylalkyl, any of which, excluding hydrogen, may be substituted with one or more groups selected from halogen, C≡N, CF$_3$, C$_1$-C$_4$ alkyl or C$_2$-C$_4$ alkenyl, C$_1$-C$_4$ alkoxy, nitro, amino, C$_1$-C$_4$ alkylamino, oxo, C$_3$-C$_6$ cycloalkyl, aryl, aralkyl, heterocyclyl or heteroaryl; with the proviso that at least one of R$^2$ and R$^3$ is different from hydrogen.

In still further particular embodiments, each of R$^2$ and R$^3$ may be independently selected from hydrogen, C$_1$-C$_4$ alkyl, C$_3$-C$_{10}$ cycloalkyl, aryl, aralkyl, heterocyclyl, heteroaryl and heteroarylalkyl, any of which, excluding hydrogen, may be substituted with one or more groups selected from halogen, C≡N, CF$_3$, C$_1$-C$_4$ alkyl, C$_1$-C$_4$ alkoxy, amino, C$_3$-C$_6$ cycloalkyl, aryl, heterocyclyl or heteroaryl.

In other particular embodiments, R$^2$ is selected from hydrogen or substituted or unsubstituted C$_1$-C$_4$ alkyl.

In still other particular embodiments, R$^3$ is selected from C$_1$-C$_4$ alkyl, aryl, aralkyl, heteroaryl and heteroarylalkyl, any of which, excluding hydrogen, may be substituted with one or more groups selected from halogen, C$_1$-C$_4$ alkyl or C$_1$-C$_4$ alkoxy.

In further particular embodiments, when Z is $SO_2NR^2R^3$, $R^2$ and $R^3$ may together form a 3-10 membered monocyclic, bicyclic or spirocyclic nitrogen-containing ring system that contains 0-3 additional heteroatoms selected from oxygen (O), nitrogen (N), and sulfur (S), and which may be further substituted with one or more groups selected from halogen, $C_1$-$C_4$ alkyl or $C_2$-$C_4$ alkenyl, $C_3$-$C_6$ cycloalkyl, $C_1$-$C_4$ alkoxy, arylalkoxy, nitro, amino, $C_1$-$C_4$ alkoxycarbonyl, acyl, $C_1$-$C_4$ alkylamino, oxo, $SO_2CH_3$, aryl, aralkyl, heterocyclyl, or heteroaryl.

In still further particular embodiments, the nitrogen-containing ring system formed by $R^2$ and $R^3$ is a 4-7 membered monocyclic ring system or a 8-10 membered bicyclic or spirocyclic nitrogen-containing ring system. In another selected embodiment the monocyclic, bicyclic or spirocyclic nitrogen-containing ring system contains 0-1 additional heteroatoms selected from oxygen (O), nitrogen (N), and sulfur (S).

In other particular embodiments, Z is $SO_2NR^2R^3$ with $NR^2R^3$ being a substituted or unsubstituted pyrrolidinyl, substituted or unsubstituted piperidinyl, substituted or unsubstituted piperazinyl, substituted or unsubstituted azetidinyl, substituted or unsubstituted 1,3,8-triazaspiro[4.5]decanyl, substituted or unsubstituted dihydroisoquinolinyl, substituted or unsubstituted dihydroisoindolyl, substituted or unsubstituted morpholinyl, substituted or unsubstituted dihydronaphthyridinyl or substituted or unsubstituted azabicyclo[3.2.2]nonyl.

In still other particular embodiments, $NR^2R^3$ is a 1-pyrrolidinyl, 1-piperidinyl, 1-piperazinyl, 1-azetidinyl, 1,3,8-triazaspiro[4.5]dec-8-yl, 3,4-dihydro-2(1H)-isoquinolinyl, 1,3-dihydro-2H-isoindol-2-yl, 4-morpholinyl, 5,8-dihydronaphthyridin-7(6H)-yl, azabicyclo[3.2.2]non-3-yl which may be further substituted with one or more groups selected from halogen, C≡N, $CF_3$, OH, $C_1$-$C_4$ alkyl, $C_3$-$C_6$ cycloalkyl, $C_1$-$C_4$ alkoxy, arylalkoxy, amino, $C_1$-$C_4$ alkoxycarbonyl, acyl, $C_1$-$C_4$ alkylamino, oxo, aryl, aralkyl, heterocyclyl, or heteroaryl.

The group X in formula I, in selected embodiments, is selected from hydrogen, halogen, trifluoromethyl, methyl and nitrile (C≡N); in further embodiments X in formula I is hydrogen, halogen, trifluoromethyl, or methyl; in further embodiments of this group, said halogen is fluorine or chlorine. In one embodiment, X is fluorine. In another embodiment, X is hydrogen. In another embodiment, X is trifluoromethyl.

Also provided herein are COMT-inhibiting compound in accordance with formula I, or a pharmaceutically acceptable salt thereof:

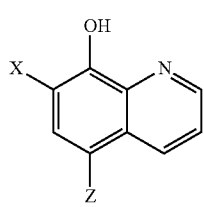

I wherein:
X is selected from H, F, Br, I, C≡N, $CF_3$, and $C_1$-$C_4$ alkyl;
Z is selected from $SO_2R^1$ and $SO_2NR^2R^3$;
$R^1$ is selected from $C_1$-$C_{10}$ alkyl, $C_3$-$C_{10}$ cycloalkyl, aryl, aralkyl, heterocyclyl, heteroaryl and heteroarylalkyl, any of which may be substituted with one or more groups selected from halogen, C≡N, $CF_3$, OH, $C_1$-$C_4$ alkyl or $C_2$-$C_4$ alkenyl, alkoxy, nitro, amino, $C_1$-$C_4$ alkylamino, oxo, $C_3$-$C_{10}$ cycloalkyl, acyl, aryl, aralkyl, heterocyclyl, heteroaryl, $CON(R^4)_2$, $SO_2R^4$, or $SO_2N(R^4)_2$, where each $R^4$ is independently $C_1$-$C_4$ alkyl or $(R^4)_2$ forms a carbocyclic ring;

$R^2$ and $R^3$ are independently selected from hydrogen and any of the groups as defined for $R^1$, with the proviso that at least one of $R^2$ or $R^3$ is different from hydrogen; or $R^2$ and $R^3$ may together form a 3-10 membered monocyclic, bicyclic or spirocyclic nitrogen-containing ring system that contains 0-3 (preferably 0-1) additional heteroatoms selected from oxygen (O), nitrogen (N), and sulfur (S), and which may be further substituted with one or more groups selected from halogen, C≡N, $CF_3$, OH, $C_1$-$C_4$ alkyl or $C_2$-$C_4$ alkenyl, $C_3$-$C_6$ cycloalkyl, alkoxy, nitro, amino, $C_1$-$C_4$ alkoxycarbonyl, acyl, $C_1$-$C_4$ alkylamino, oxo, $SO_2CH_3$, aryl, aralkyl, heterocyclyl, heteroaryl or heteroarylalkyl;

with the proviso that when X is hydrogen and Z is $SO_2R^1$, $R^1$ is not $C_1$ alkyl, $C_4$ alkyl, $C_8$ alkyl, phenyl, 4-methylphenyl, 4-methoxybenzyl, 4-bromophenyl, 4-iodophenyl, 2,4,6-trimethylphenyl, $CH(COMe)_2$, $CH(CO_2Et)_2$, 4-BnOPh, tetrahydropyran or propylcyclopropane;

or when X is H and Z is $SO_2NR^2R^3$, $R^2$ and $R^3$ do not together form a 1-piperidinyl ring substituted with an α-methyl group.

An additional embodiment of the above includes the proviso that when X is F and Z is $SO_2R^1$, $R^1$ is not pyridyl, cyclopentyl and phenyl substituted with fluoro, or trifluoromethyl.

A second additional embodiment of the above further includes the proviso that when X is Cl and Z is $SO_2R^1$, $R^1$ is not thiazolyl, pyridyl, pyridyl-N-oxide, and phenyl substituted with one or two groups selected from fluoro, chloro, methyl, trifluoromethyl, phenyl and tert-butyl.

Also provided herein are COMT-inhibiting compound in accordance with formula I, or a pharmaceutically acceptable salt thereof:

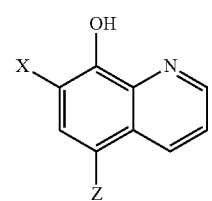

I wherein:
X is selected from halogen, C≡N, $CF_3$, and $C_1$-$C_4$ alkyl;
Z is selected from $SO_2R^1$ and $SO_2NR^2R^3$;
$R^1$ is selected from $C_1$-$C_{10}$ alkyl, $C_3$-$C_{10}$ cycloalkyl, aryl, aralkyl, heterocyclyl, heteroaryl and heteroarylalkyl, any of which may be substituted with one or more groups selected from halogen, C≡N, $CF_3$, OH, $C_1$-$C_4$ alkyl or $C_2$-$C_4$ alkenyl, alkoxy, nitro, amino, $C_1$-$C_4$ alkylamino, oxo, $C_3$-$C_{10}$ cycloalkyl, acyl, aryl, aralkyl, heterocyclyl, heteroaryl, $CON(R^4)_2$, $SO_2R^4$, or $SO_2N(R^4)_2$, where each $R^4$ is independently $C_1$-$C_4$ alkyl or $(R^4)_2$ forms a carbocyclic ring;

$R^2$ and $R^3$ are independently selected from hydrogen and any of the groups as defined for $R^1$, with the proviso that at least one of $R^2$ or $R^3$ is different from hydrogen; or $R^2$ and $R^3$ may together form a 3-10 membered monocyclic, bicyclic or spirocyclic nitrogen-containing ring system that contains 0-3 (preferably 0-1) additional heteroatoms selected from oxygen (O), nitrogen (N), and sulfur (S), and which may be further substituted with one or more groups selected from halogen, C≡N, $CF_3$, OH, $C_1$-$C_4$ alkyl or $C_2$-$C_4$ alkenyl, $C_3$-$C_6$ cycloalkyl, alkoxy, nitro, amino, $C_1$-$C_4$ alkoxycarbonyl, acyl, $C_1$-$C_4$ alkylamino, oxo, $SO_2CH_3$, aryl, aralkyl, heterocyclyl, heteroaryl or heteroarylalkyl;

with the proviso that when X is Cl and Z is $SO_2R^1$, $R^1$ is not $C_3$ alkyl, $C_4$ alkyl or $C_5$-$C_6$ cycloalkyl;

or when X is Cl and Z is $SO_2NR^2R^3$, $R^2$ and $R^3$ do not together form an unsubstituted, 1-pyrrolidinyl ring.

An additional embodiment of the above includes the proviso that when X is F and Z is $SO_2R^1$, $R^1$ is not pyridyl, cyclopentyl and phenyl substituted with fluoro, or trifluoromethyl.

A second additional embodiment of the above further includes the proviso that when X is Cl and Z is $SO_2R^1$, $R^1$ is not thiazolyl, pyridyl, pyridyl-N-oxide, and phenyl substituted with one or two groups selected from fluoro, chloro, methyl, trifluoromethyl, phenyl and tert-butyl.

In a specific embodiment, $R^1$ is ethyl, 2-propanyl, 2-methylpropyl, octyl, 3-cyclopropylpropyl, 4-methylbenzyl, 2-(4-methylphenyl)ethyl, cyclopentyl, cyclohexyl, 3-methylphenyl, 4-methylphenyl, 2,4-dimethylphenyl, 3,4-dimethylphenyl, 3,5-dimethylphenyl, 2-trifluoromethylphenyl, 3-trifluoromethylphenyl, 4-trifluoromethylphenyl, 4-tert-butylphenyl, 3-chlorophenyl, 4-chlorophenyl, 4-fluorophenyl, 3,5-dichlorophenyl, 3,4-dichlorophenyl, 4-fluoro-2-methylphenyl, 3-(quinolin-5-yl)phenyl, biphenyl-3-yl, 3'-chloro-4'-fluorobiphenyl-3-yl, 3-(1H-indazol-4-yl)phenyl, 3-(pyridin-4-yl)phenyl, 2-naphthyl, 2-pyridinyl, 3-pyridinyl, 4-pyridinyl, 3-methylpyridin-4-yl, 1-(2,3-dimethylphenyl)pyridin-4-yl, 4-piperidinyl, 1-(2,3-dichlorobenzoyl)piperidin-4-yl, (4-fluorobenzyl)piperidin-4-yl, 1-(4-fluorophenyl)-piperidin-4-yl, 1-(2,3-dichlorobenzyl)piperidin-4-yl, 1-(2-chlorobenzyl)-1H-benzimidazol-4-yl, tetrahydro-2H-pyran-4-yl.

The group X in formula I, in selected embodiments of the sulfonylquinolinol derivatives, is selected from hydrogen, halogen, trifluoromethyl, methyl and nitrile (C≡N); in further embodiments X in formula I is hydrogen, halogen or methyl; in further embodiments of this group, said halogen is fluorine or chlorine. In one embodiment, X is fluorine. In another embodiment, X is hydrogen. In another embodiment, X is trifluoromethyl.

Also provided herein are COMT-inhibiting compound in accordance with formula II, or a pharmaceutically acceptable salt thereof:

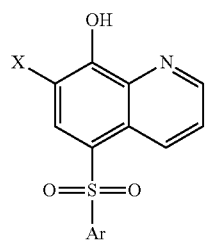

II wherein:
X is selected from hydrogen, halogen, C≡N, $CF_3$, and $C_1$-$C_4$ alkyl;

Ar is aryl or heteroaryl, optionally substituted with one or more groups selected from halogen, C≡N, $CF_3$, OH, $C_1$-$C_4$ alkyl or $C_2$-$C_4$ alkenyl, alkoxy, nitro, amino, $C_1$-$C_4$ alkylamino, oxo, $C_3$-$C_{10}$ cycloalkyl, acyl, aryl, aralkyl, heterocyclyl, heteroaryl, $CON(R^4)_2$, $SO_2R^4$, or $SO_2N(R^4)_2$, where each $R^4$ is independently $C_1$-$C_4$ alkyl or $(R^4)_2$ forms a carbocyclic ring;

with the proviso that when X is hydrogen, $R^1$ is not phenyl, 4-methylphenyl, 4-methoxybenzyl, 4-bromophenyl, 4-iodophenyl or 2,4,6-trimethylphenyl.

In particular embodiments, Ar is heteroaryl, optionally substituted with one or more groups selected from halogen, C≡N, $CF_3$, OH, $C_1$-$C_4$ alkyl or $C_2$-$C_4$ alkenyl, alkoxy, nitro, amino, $C_1$-$C_4$ alkylamino, oxo, $C_3$-$C_{10}$ cycloalkyl, acyl, aryl, aralkyl, heterocyclyl, heteroaryl, $CON(R^4)_2$, $SO_2R^4$, or $SO_2N(R^4)_2$, where each $R^4$ is independently $C_1$-$C_4$ alkyl or $(R^4)_2$ forms a carbocyclic ring.

In more particular embodiments, Ar is heteroaryl selected from the following moieties (arrow indicates point of attachment):

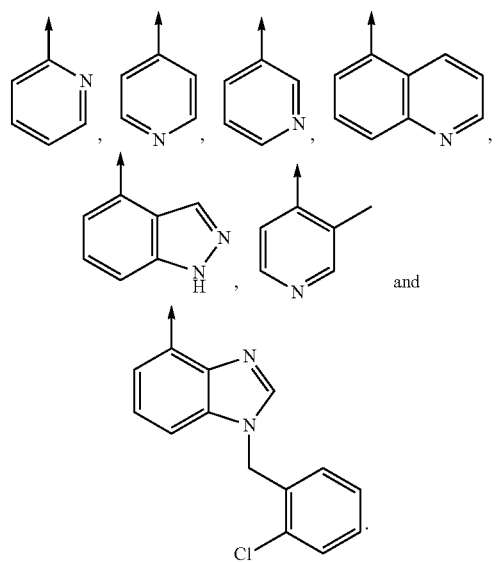

In other particular embodiments, Ar is aryl, optionally substituted with one or more groups selected from halogen, C≡N, $CF_3$, OH, $C_1$-$C_4$ alkyl or $C_2$-$C_4$ alkenyl, alkoxy, nitro, amino, $C_1$-$C_4$ alkylamino, oxo, $C_3$-$C_{10}$ cycloalkyl, acyl, aryl, aralkyl, heterocyclyl, heteroaryl, $CON(R^4)_2$, $SO_2R^4$, or $SO_2N(R^4)_2$, where each $R^4$ is independently $C_1$-$C_4$ alkyl or $(R^4)_2$ forms a carbocyclic ring.

In still other particular embodiments, Ar is phenyl, optionally substituted with one or more groups selected from halogen, C≡N, $CF_3$, OH, $C_1$-$C_4$ alkyl or $C_2$-$C_4$ alkenyl, alkoxy, nitro, amino, $C_1$-$C_4$ alkylamino, oxo, $C_3$-$C_{10}$ cycloalkyl, acyl, aryl, aralkyl, heterocyclyl, heteroaryl, $CON(R^4)_2$, $SO_2R^4$, or $SO_2N(R^4)_2$, where each $R^4$ is independently $C_1$-$C_4$ alkyl or $(R^4)_2$ forms a carbocyclic ring.

In more particular embodiments, Ar is phenyl optionally substituted with one or more groups selected from halogen, $C_1$-$C_4$ alkyl, alkoxyl or heteroaryl.

In further particular embodiments, Ar is selected from the following moieties (arrow indicates point of attachment):

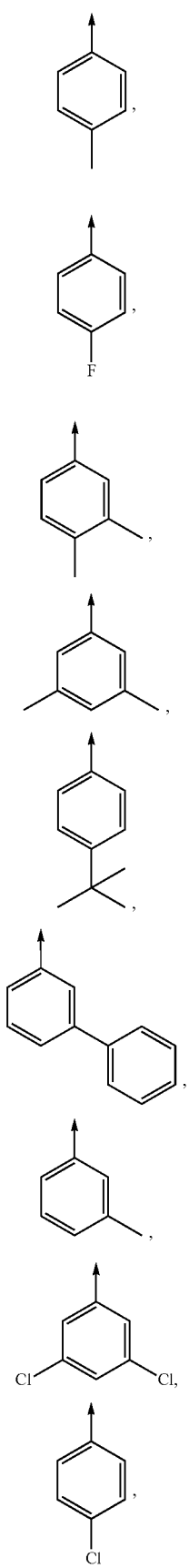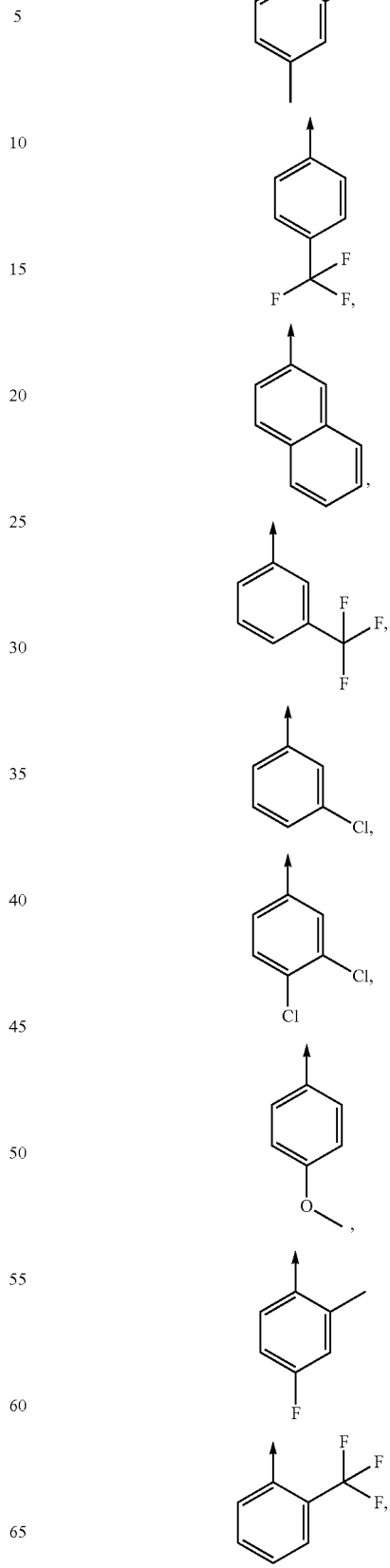

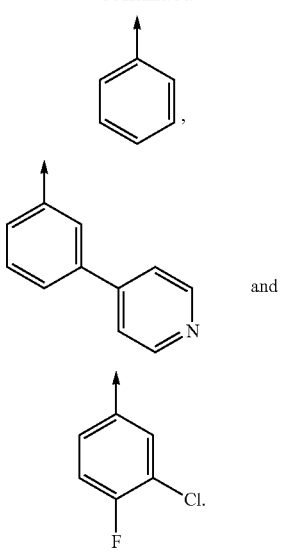

and

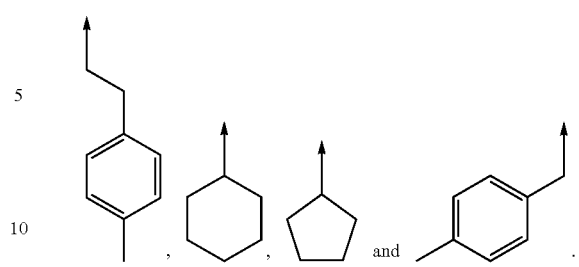

Also provided herein are COMT-inhibiting compound in accordance with formula IV, or a pharmaceutically acceptable salt thereof:

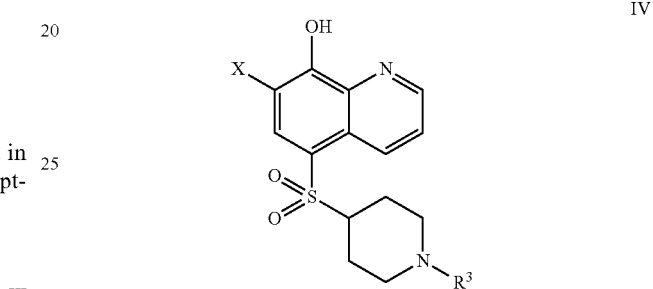

IV wherein:

X is selected from hydrogen, halogen, C≡N, CF$_3$, and C$_1$-C$_4$ alkyl; and

R$^3$ is selected from hydrogen, C$_1$-C$_{10}$ alkyl, C$_3$-C$_{10}$ cycloalkyl, aryl, aralkyl, heterocyclyl, heteroaryl, heteroarylalkyl or acyl, any of which may be substituted with one or more groups selected from halogen, C≡N, CF$_3$, OH, C$_1$-C$_4$ alkyl or C$_2$-C$_4$ alkenyl, alkoxy, nitro, amino, C$_1$-C$_4$ alkylamino, oxo, C$_3$-C$_{10}$ cycloalkyl, acyl, aryl, aralkyl, heterocyclyl, heteroaryl, CON(R$^4$)$_2$, SO$_2$R$^4$, or SO$_2$N(R$^4$)$_2$, where each R$^4$ is independently C$_1$-C$_4$ alkyl or (R$^4$)$_2$ forms a carbocyclic ring.

In more particular embodiments, X is hydrogen and R$^3$ is selected from aralkyl, acyl, or aryl.

In further particular embodiments, R$^3$ is selected from the following moieties (arrow indicates point of attachment):

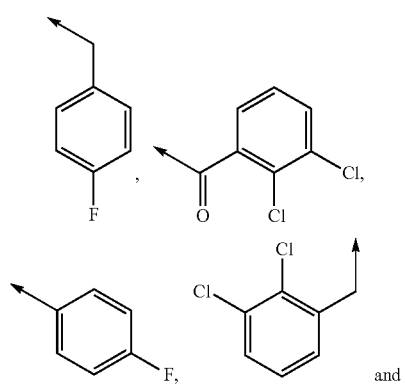

Also provided herein are COMT-inhibiting compound in accordance with formula III, or a pharmaceutically acceptable salt thereof:

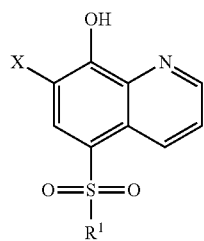

III wherein:

X is selected from hydrogen, F, Br, I, C≡N, CF$_3$, and C$_1$-C$_4$ alkyl; and

R$^1$ is selected from C$_3$-C$_{10}$ cycloalkyl, aryl, aralkyl, heteroaryl and heteroarylalkyl, any of which may be substituted with one or more groups selected from halogen, C≡N, CF$_3$, OH, C$_1$-C$_4$ alkyl or C$_2$-C$_4$ alkenyl, alkoxy, nitro, amino, C$_1$-C$_4$ alkylamino, oxo, C$_3$-C$_{10}$ cycloalkyl, acyl, aryl, aralkyl, heterocyclyl, heteroaryl, CON(R$^4$)$_2$, SO$_2$R$^4$, or SO$_2$N(R$^4$)$_2$, where each R$^4$ is independently C$_1$-C$_4$ alkyl or (R$^4$)$_2$ forms a carbocyclic ring;

with the proviso that when X is hydrogen, R$^1$ is not phenyl, 4-methylphenyl, 4-methoxybenzyl, 4-bromophenyl, 4-iodophenyl, 2,4,6-trimethylphenyl or 4-BnOPh.

The group X in formula III, in selected embodiments of the sulfonylquinolinol derivatives, is selected from hydrogen, halogen, methyl, trifluoromethyl, and nitrile (C≡N); in further embodiments X in formula I is hydrogen, halogen or methyl; in further embodiments of this group, said halogen is fluorine or chlorine. In one embodiment, X is fluorine. In another embodiment, X is hydrogen. In a further embodiment, X is trifluoromethyl.

In particular embodiments, R$^1$ is selected from the following moieties (arrow indicates point of attachment):

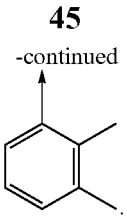

Specific sulfonylquinolinol derivatives of the present invention are those selected from the group consisting of:
5-tosylquinolin-8-ol;
5-(4-fluorophenyl)sulfonylquinolin-8-ol;
5-(3,4-dimethylphenyl)sulfonylquinolin-8-ol;
5-(3,5-dimethylphenyl)sulfonylquinolin-8-ol;
5-(4-tert-butylphenyl)sulfonylquinolin-8-ol;
5-(3-phenylphenyl)sulfonylquinolin-8-ol;
5-(m-tolylsulfonyl)quinolin-8-ol;
5-(3,5-dichlorophenyl)sulfonylquinolin-8-ol;
5-(4-chlorophenyl)sulfonylquinolin-8-ol;
5-(2,4-dimethylphenyl)sulfonylquinolin-8-ol;
5-[4-(trifluoromethyl)phenyl]sulfonylquinolin-8-ol;
5-(2-naphthyl sulfonyl)quinolin-8-ol;
5-[3-(trifluoromethyl)phenyl]sulfonylquinolin-8-ol;
5-(3-chlorophenyl)sulfonylquinolin-8-ol;
5-(3,4-dichlorophenyl)sulfonylquinolin-8-ol;
5-(2-pyridylsulfonyl)quinolin-8-ol;
5-(4-pyridylsulfonyl)quinolin-8-ol;
5-(4-methoxyphenyl)sulfonylquinolin-8-ol;
5-(3-pyridylsulfonyl)quinolin-8-ol;
5-(4-fluoro-2-methyl-phenyl)sulfonylquinolin-8-ol;
5-[2-(trifluoromethyl)phenyl]sulfonylquinolin-8-ol;
5-(benzenesulfonyl)quinolin-8-ol;
5-[3-(4-pyridyl)phenyl]sulfonylquinolin-8-ol;
5-[3-(3-chloro-4-fluoro-phenyl)phenyl]sulfonylquinolin-8-ol;
5-[3-(5-quinolyl)phenyl]sulfonylquinolin-8-ol;
5-[3-(1H-indazol-4-yl)phenyl]sulfonylquinolin-8-ol;
5-[(3-methyl-4-pyridyl)sulfonyl]quinolin-8-ol;
5-[1-[(2-chlorophenyl)methyl]benzimidazol-4-yl]sulfonylquinolin-8-ol;
5-[2-(p-tolyl)ethylsulfonyl]quinolin-8-ol;
5-cyclohexylsulfonylquinolin-8-ol;
5-cyclopentylsulfonylquinolin-8-ol;
5-(p-tolylmethylsulfonyl)quinolin-8-ol;
5-ethyl sulfonylquinolin-8-ol;
5-(4-piperidylsulfonyl)quinolin-8-ol;
5-[[1-[(4-fluorophenyl)methyl]-4-piperidyl]sulfonyl]quinolin-8-ol;
5-[[1-[(2,3-dichlorophenyl)methyl]-4-piperidyl]sulfonyl]quinolin-8-ol;
5-[[1-(4-fluorophenyl)-4-piperidyl]sulfonyl]quinolin-8-ol;
5-[[1-(2,3-dimethylphenyl)-4-piperidyl]sulfonyl]quinolin-8-ol;
7-iodo-5-(p-tolylsulfonyl)quinolin-8-ol;
7-bromo-5-(p-tolylsulfonyl)quinolin-8-ol;
7-chloro-5-(p-tolylsulfonyl)quinolin-8-ol;
7-fluoro-5-(p-tolylsulfonyl)quinolin-8-ol;
5-(p-tolylsulfonyl)-7-(trifluoromethyl)quinolin-8-ol; and
5-cyclopentylsulfonyl-7-(trifluoromethyl)quinolin-8-ol.

Also provided herein are COMT-inhibiting compound in accordance with formula I, or a pharmaceutically acceptable salt thereof:

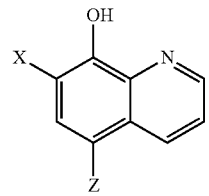

wherein:
X is selected from hydrogen, halogen, C≡N, $CF_3$, and $C_1$-$C_4$ alkyl;
Z is $SO_2NR^2R^3$, wherein $NR^2R^3$ is a 1-pyrrolidinyl, 1-piperidinyl, 1-piperazinyl, 1-azetidinyl, 1,3,8-triazaspiro[4.5]dec-8-yl, 3,4-dihydro-2(1H)-isoquinolinyl, 1,3-dihydro-2H-isoindol-2-yl, 4-morpholinyl, 5,8-dihydronaphthyridin-7(6H)-yl, azabicyclo[3.2.2]non-3-yl which may be further substituted with one or more groups selected from halogen, C≡N, $CF_3$, OH, $C_1$-$C_4$ alkyl or $C_2$-$C_4$ alkenyl, $C_3$-$C_6$ cycloalkyl, $C_1$-$C_4$ alkoxy, arylalkoxy, nitro, amino, $C_1$-$C_4$ alkoxycarbonyl, acyl, $C_1$-$C_4$ alkylamino, oxo, $SO_2CH_3$, aryl, aralkyl, heterocyclyl, or heteroaryl;
with the proviso that when X is H, $NR^2R^3$ do not together form a 1-piperidinyl ring substituted with a α-methyl group;
or when X is Cl, $NR^2R^3$ do not together form an unsubstituted, 1-pyrrolidinyl ring.

In yet another particular embodiment, $NR^2R^3$ is selected from 1-pyrrolidinyl, 2-methylpyrrolidin-1-yl, (2R)-2-methylpyrrolidin-1-yl, (2S)-2-methylpyrrolidin-1-yl, (3R,4R)-3,4-difluoropyrrolidin-1-yl, 2-(propan-2-yl)pyrrolidin-1-yl, 2-(2-methylpropyl)pyrrolidin-1-yl, 2-cyclohexylpyrrolidin-1-yl, 2-benzylpyrrolidin-1-yl, 2-phenylpyrrolidin-1-yl, 2-(2-methylphenyl)pyrrolidin-1-yl, 2-(4-fluorophenyl)pyrrolidin-1-yl, 3-(4-fluorophenyl)pyrrolidin-1-yl, 2-(4-methoxyphenyl)pyrrolidin-1-yl, 2-[2-(trifluoromethyl)phenyl]pyrrolidin-1-yl, 2-(pyridin-2-yl)pyrrolidin-1-yl, 2-(pyridin-3-yl)pyrrolidin-1-yl, 2-(pyridin-4-yl)pyrrolidin-1-yl, 1-piperidinyl, 2-phenylpiperidin-1-yl, 3-phenylpiperidin-1-yl, 4-phenylpiperidin-1-yl, 4-hydroxy-4-phenylpiperidin-1-yl, 4-acetyl-4-phenylpiperidin-1-yl, 4-benzylpiperidin-1-yl, 4-benzoylpiperidin-1-yl, 1-piperazinyl, 2-methylpiperazin-1-yl, 4-methylpiperazin-1-yl, 4-phenylpiperazin-1-yl, 4-(2, 3-dimethylphenyl)piperazin-1-yl, 4-(2, 5-dimethylphenyl)piperazin-1-yl, 4-(4-fluorophenyl)piperazin-1-yl, 4-(2,3-dichlorophenyl)piperazin-1-yl, 4-[4-(trifluoromethyl)phenyl]piperazin-1-yl, 4-(2-cyanophenyl)piperazin-1-yl, 4-(biphenyl-2-yl)piperazin-1-yl, 4-benzylpiperazin-1-yl, 4-(4-fluorobenzyl)piperazin-1-yl, 4-(3-methoxypropyl)piperazin-1-yl, 4-(methoxycarbonyl)piperazin-1-yl, 4-(tert-butoxycarbonyl)piperazin-1-yl, 4-(tert-butoxycarbonyl)-2-methylpiperazin-1-yl, 4-(5-chloropyridin-2-yl)piperazin-1-yl, 4-[bis(4-fluorophenyl)methyl]piperazin-1-yl, 4-(1,2-benzothiazol-3-yl)piperazin-1-yl, 3,4-dihydroisoquinolin-2(1H)-yl , 1,3-dihydro-2H-isoindol-2-yl, 5,8-dihydro-1,7-naphthyridin-7(6H)-yl, 4-oxo-1-phenyl-1,3,8-triazaspiro[4.5]dec-8-yl, 3-azabicyclo[3.2.2]non-3-yl or 3-[4-(trifluoromethoxy)phenoxy]azetidin-1-yl.

Also provided herein are COMT-inhibiting compound in accordance with formula V, or a pharmaceutically acceptable salt thereof:

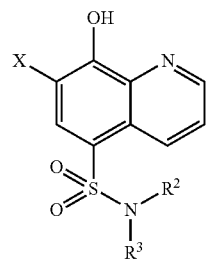

wherein:

X is selected from hydrogen, halogen, C≡N, CF$_3$, and C$_1$-C$_4$ alkyl;

R$^2$ and R$^3$ are independently selected from hydrogen, C$_1$-C$_{10}$ alkyl, C$_3$-C$_{10}$ cycloalkyl, aryl, aralkyl, heterocyclyl, heteroaryl and heteroarylalkyl, any of which may be substituted with one or more groups selected from halogen, C≡N, CF$_3$, OH, C$_1$-C$_4$ alkyl or C$_2$-C$_4$ alkenyl, alkoxy, nitro, amino, C$_1$-C$_4$ alkylamino, oxo, C$_3$-C$_{10}$ cycloalkyl, acyl, aryl, aralkyl, heterocyclyl, heteroaryl, CON(R$^4$)$_2$, SO$_2$R$^4$, or SO$_2$N(R$^4$)$_2$, where each R$^4$ is independently C$_1$-C$_4$ alkyl or (R$^4$)$_2$ forms a carbocyclic ring;

with the proviso that at least one of R$^2$ or R$^3$ is different from hydrogen;

or when X is H, R$^2$ and R$^3$ do not together form a 1-piperidinyl ring substituted with a α-methyl group;

or when X is Cl, R$^2$ and R$^3$ do not together form an unsubstituted, 1-pyrrolidinyl ring.

In particular embodiments, NR$^2$R$^1$ is selected from the following moieties (arrow indicates point of attachment):

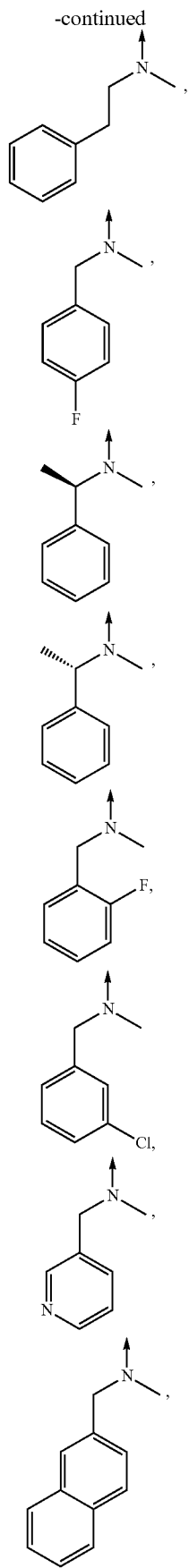

-continued

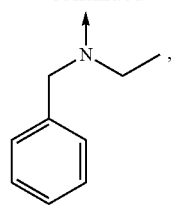

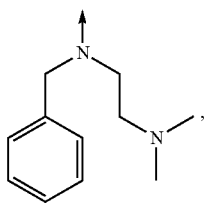

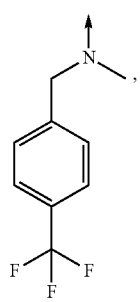

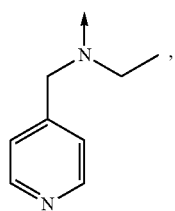

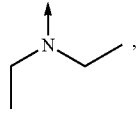

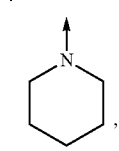  and

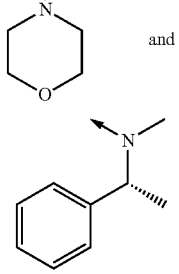

Also provided herein are COMT-inhibiting compound in accordance with formula VI, or a pharmaceutically acceptable salt thereof:

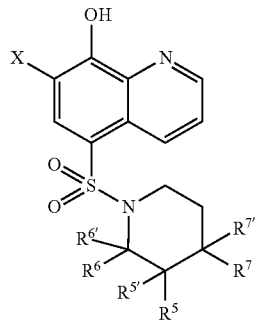

VI wherein:
X is selected from hydrogen, halogen, C≡N, CF$_3$, and C$_1$-C$_4$ alkyl;
R$^5$, R$^{5'}$, R$^6$, R$^{6'}$, R$^7$ and R$^{7'}$ are each independently selected from hydrogen, halogen, hydroxyl, C≡N, CF$_3$, OH, C$_1$-C$_4$ alkyl or C$_2$-C$_4$ alkenyl, C$_3$-C$_6$ cycloalkyl, alkoxy, nitro, amino, C$_1$-C$_4$ alkoxycarbonyl, acyl, C$_1$-C$_4$ alkylamino, oxo, SO$_2$CH$_3$, aryl, aralkyl, heterocyclyl, heteroaryl or heteroarylalkyl, or
two of R$^5$, R$^{5'}$, R$^6$, R$^{6'}$, R$^7$ and R$^{7'}$ come together to form an aliphatic or aromatic ring; with the proviso that when X is H, neither R$^6$ nor R$^{6'}$ are a methyl group.

In particular embodiments, the piperidine with R$^5$, R$^{5'}$, R$^6$, R$^{6'}$, R$^7$ and R$^{7'}$ substitution is selected from the following moieties (arrow indicates point of attachment):

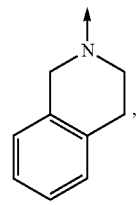

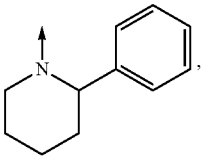

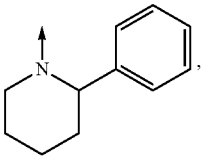

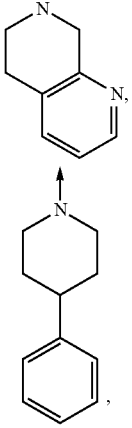

-continued

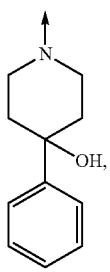

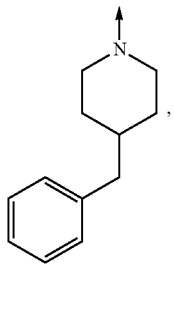

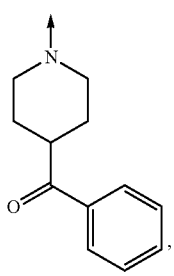

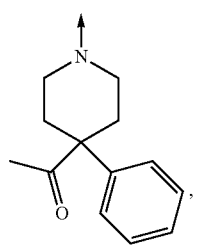

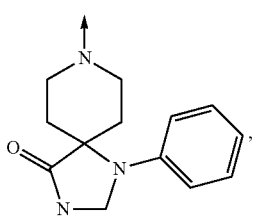

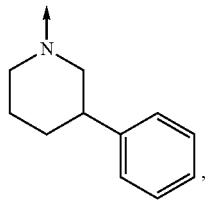

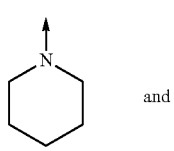 and

-continued

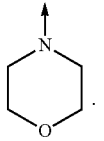

Also provided herein are COMT-inhibiting compound in accordance with formula VII, or a pharmaceutically acceptable salt thereof:

VII

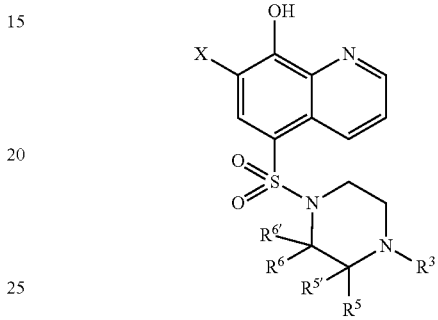

wherein:

X is selected from hydrogen, halogen, C≡N, $CF_3$, and $C_1$-$C_4$ alkyl;

$R^3$, $R^5$, $R^{5'}$, $R^6$ and $R^{6'}$ are each independently selected from hydrogen, halogen, hydroxyl, C≡N, $CF_3$, OH, $C_1$-$C_4$ alkyl or $C_2$-$C_4$ alkenyl, $C_3$-$C_6$ cycloalkyl, alkoxy, nitro, amino, $C_1$-$C_4$ alkoxycarbonyl, acyl, $C_1$-$C_4$ alkylamino, oxo, $SO_2CH_3$, aryl, aralkyl, heterocyclyl, heteroaryl or heteroarylalkyl, or two of $R^3$, $R^5$, $R^{5'}$, $R^6$ or $R^{6'}$ come together to form an aliphatic or aromatic ring.

In particular embodiments, $R^5$, $R^{5'}$, $R^6$ and $R^{6'}$ are each hydrogen.

In other particular embodiments, the piperizine with $R^3$, $R^5$, $R^{5'}$, $R^6$ and $R^{6'}$ substitution is selected from the following moieties (arrow indicates point of attachment):

53
-continued
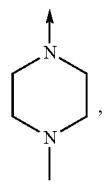
,
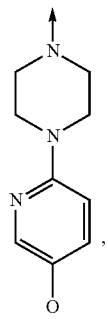
,
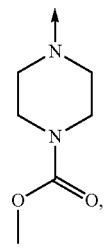
,
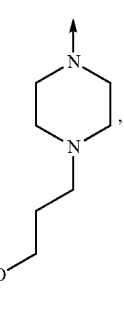
,
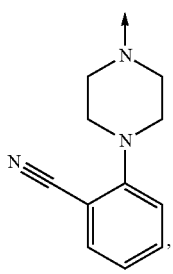
,
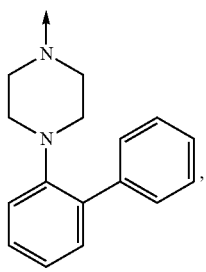
,
54
-continued
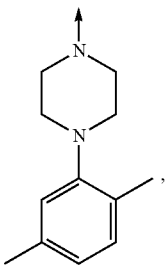
,
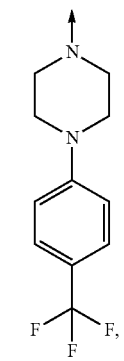
,
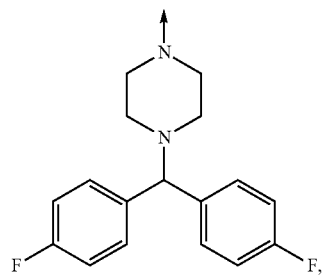
,
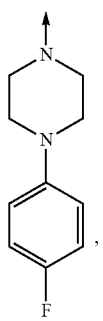
,
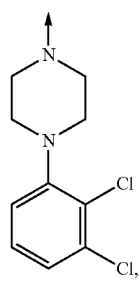
, -continued

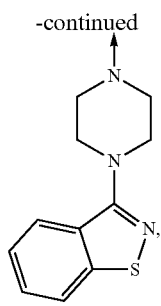

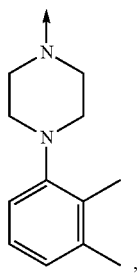

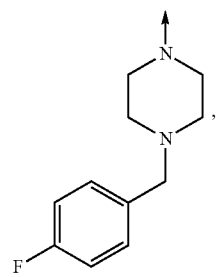

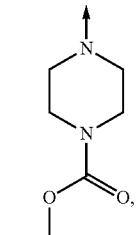

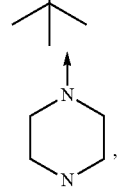

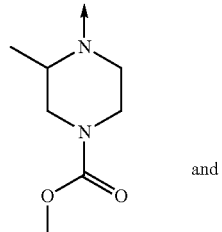

and

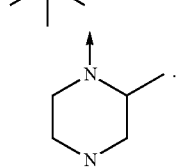

Also provided herein are COMT-inhibiting compound in accordance with formula VIII, or a pharmaceutically acceptable salt thereof:

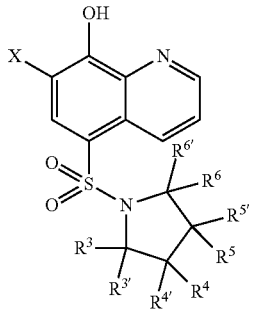

VIII wherein:

X is selected from hydrogen, halogen, C≡N, $CF_3$, and $C_1$-$C_4$ alkyl;

$R^3$, $R^{3'}$, $R^4$, $R^{4'}$, $R^5$, $R^{5'}$, $R^6$ and $R^{6'}$ are each independently selected from hydrogen, halogen, hydroxyl, C≡N, $CF_3$, OH, $C_1$-$C_4$ alkyl or $C_2$-$C_4$ alkenyl, $C_3$-$C_6$ cycloalkyl, alkoxy, nitro, amino, $C_1$-$C_4$ alkoxycarbonyl, acyl, $C_1$-$C_4$ alkylamino, oxo, $SO_2CH_3$, aryl, aralkyl, heterocyclyl, heteroaryl or heteroarylalkyl, or two of $R^3$, $R^{3'}$, $R^4$, $R^{4'}$, $R^5$, $R^{5'}$, $R^6$ or $R^{6'}$ come together to form an aliphatic or aromatic ring;

with the proviso that when X is Cl, all of $R^3$, $R^{3'}$, $R^4$, $R^{4'}$, $R^5$, $R^{5'}$, $R^6$ and $R^{6'}$ are not hydrogen.

In particular embodiments, all but one of $R^3$, $R^{3'}$, $R^4$, $R^{4'}$, $R^5$, $R^{5'}$, $R^6$ and $R^{6'}$ is hydrogen.

In other particular embodiments, $R^3$, $R^{3'}$, $R^6$ or $R^{6'}$ are aryl or heteroaryl, optionally substituted with one or more groups selected from halogen, $C_1$-$C_4$ alkyl, alkyoxyl and haloalkyl.

In still other particular embodiments, $R^3$, $R^{3'}$, $R^6$ or $R^{6'}$ are heteroaryl, preferably pyridine.

In further embodiments, $R^3$, $R^{3'}$, $R^6$ or $R^{6'}$ are $C_1$-$C_4$ alkyl or cycloalkyl.

In more particular embodiments, the pyrrolidone with $R^3$, $R^{3'}$, $R^4$, $R^{4'}$, $R^5$, $R^5$=, $R^6$ and $R^{6'}$ substitution is selected from the following moieties (arrow indicates point of attachment):

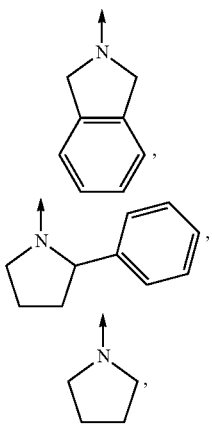

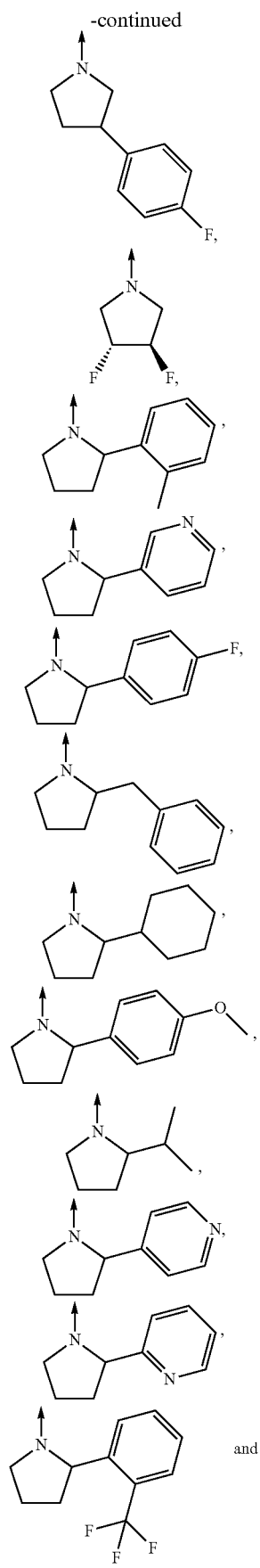

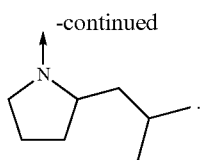

Specific hydroxyquinoline sulfonamide derivatives for use in the methods described herein are selected from the group consisting of:

5-(3,4-dihydro-1H-isoquinolin-2-ylsulfonyl)quinolin-8-ol;
5-(4-phenylpiperazin-1-yl)sulfonylquinolin-8-ol;
5-(4-benzylpiperazin-1-yl)sulfonylquinolin-8-ol;
5-isoindolin-2-ylsulfonylquinolin-8-ol;
5-(2-phenylpyrrolidin-1-yl)sulfonylquinolin-8-ol;
5-pyrrolidin-1-ylsulfonylquinolin-8-ol;
5-(4-methylpiperazin-1-yl)sulfonylquinolin-8-ol;
5-[(2-phenyl-1-piperidyl)sulfonyl]quinolin-8-ol;
5-(3-(4-fluorophenyl)pyrrolidin-1-yl)sulfonylquinolin-8-ol;
5-(6,8-dihydro-5H-1,7-naphthyridin-7-ylsulfonyl)quinolin-8-ol;
5-[4-(5-chloro-2-pyridyl)piperazin-1-yl]sulfonylquinolin-8-ol;
5-[(3R,4R)-3,4-difluoropyrrolidin-1-yl]sulfonylquinolin-8-ol;
5-[2-(o-tolyl)pyrrolidin-1-yl]sulfonylquinolin-8-ol;
5-[2-(3-pyridyl)pyrrolidin-1-yl]sulfonylquinolin-8-ol;
5-[(4-phenyl-1-piperidyl)sulfonyl]quinolin-8-ol;
5-[2-(4-fluorophenyl)pyrrolidin-1-yl]sulfonylquinolin-8-ol;
5-(2-benzylpyrrolidin-1-yl)sulfonylquinolin-8-ol;
5-(2-cyclohexylpyrrolidin-1-yl)sulfonylquinolin-8-ol;
5-[2-(4-methoxyphenyl)pyrrolidin-1-yl]sulfonylquinolin-8-ol;
5-(2-isopropylpyrrolidin-1-yl)sulfonylquinolin-8-ol;
5-[2-(4-pyridyl)pyrrolidin-1-yl]sulfonylquinolin-8-ol;
5-[2-(2-pyridyl)pyrrolidin-1-yl]sulfonylquinolin-8-ol;
5-[2-[2-(trifluoromethyl)phenyl]pyrrolidin-1-yl]sulfonylquinolin-8-ol;
5-(2-isobutylpyrrolidin-1-yl)sulfonylquinolin-8-ol;
5-[(4-hydroxy-4-phenyl-1-piperidyl)sulfonyl]quinolin-8-ol;
5-[(4-benzyl-1-piperidyl)sulfonyl]quinolin-8-ol;
[1-[(8-hydroxy-5-quinolyl)sulfonyl]-4-piperidyl]-phenyl-methanone;
1-[1-[(8-hydroxy-5-quinolyl)sulfonyl]-4-phenyl-4-piperidyl]ethanone;
8-[(8-hydroxy-5-quinolyl)sulfonyl]-1-phenyl-1,3, 8-triazaspiro[4.5]decan-4-one;
methyl 4-[(8-hydroxy-5-quinolyl)sulfonyl]piperazine-1-carboxylate;
5-[4-(3-methoxypropyl)piperazin-1-yl]sulfonylquinolin-8-ol;
2-[4-[(8-hydroxy-5-quinolyl)sulfonyl]piperazin-1-yl]benzonitrile;
5-(3-azabicyclo[3.2.2]nonan-3-ylsulfonyl)quinolin-8-ol;
5-[4-(2-phenylphenyl)piperazin-1-yl]sulfonylquinolin-8-ol;
5-[4-(2, 5-dimethylphenyl)piperazin-1-yl]sulfonylquinolin-8-ol;
5-[4-[4-(trifluoromethyl)phenyl]piperazin-1-yl]sulfonylquinolin-8-ol;
5-[4-[bis(4-fluorophenyl)methyl]piperazin-1-yl]sulfonylquinolin-8-ol;
5-[4-(4-fluorophenyl)piperazin-1-yl]sulfonylquinolin-8-ol;
5-[4-(2,3-dichlorophenyl)piperazin-1-yl]sulfonylquinolin-8-ol;
5-[4-(1,2-benzothiazol-3-yl)piperazin-1-yl]sulfonylquinolin-8-ol;

5-[3-[4-(trifluoromethoxy)phenoxy]azetidin-1-yl]sulfonylquinolin-8-ol;
5-[4-(2,3-dimethylphenyl)piperazin-1-yl]sulfonylquinolin-8-ol;
5-[4-[(4-fluorophenyl)methyl]piperazin-1-yl]sulfonylquinolin-8-ol;
5-[(3-phenyl-1-piperidyl)sulfonyl]quinolin-8-ol;
tert-butyl 4-[(8-hydroxy-5-quinolyl)sulfonyl]piperazine-1-carboxylate;
5-piperazin-1-ylsulfonylquinolin-8-ol;
tert-butyl 4-[(8-hydroxy-5-quinolyl)sulfonyl]-3-methyl-piperazine-1-carboxylate;
5-(2-methylpiperazin-1-yl)sulfonylquinolin-8-ol;
7-methyl-5-pyrrolidin-1-yl sulfonyl-quinolin-8-ol;
7-chloro-5-[4-[(4-fluorophenyl)methyl]piperazin-1-yl]sulfonyl-quinolin-8-ol;
7-fluoro-5-[4-[(4-fluorophenyl)methyl]piperazin-1-yl]sulfonyl-quinolin-8-ol;
5-[(2-methylpyrrolidin-1-yl)sulfonyl]quinolin-8-ol; 5-[4-[(4-fluorophenyl)methyl]piperazin-1-yl]sulfonyl-7-methyl-quinolin-8-ol;
5-[(3R,4R)-3,4-difluoropyrrolidin-1-yl]sulfonyl-7-methyl-quinolin-8-ol;
7-chloro-5-[(2S)-2-methylpyrrolidin-1-yl]sulfonyl-quinolin-8-ol;
7-chloro-5-[(2R)-2-methylpyrrolidin-1-yl]sulfonyl-quinolin-8-ol;
7-bromo-5-[4-[(4-fluorophenyl)methyl]piperazin-1-yl]sulfonyl-quinolin-8-ol;
7-fluoro-5-pyrrolidin-1-yl sulfonyl-quinolin-8-ol;
8-hydroxy-N-[(3-methoxyphenyl)methyl]-N-methyl-quinoline-5-sulfonamide;
8-hydroxy-N-(4-methylbenzyl)quinoline-5-sulfonamide;
N-benzyl-8-hydroxy-N-methyl quinoline-5-sulfonamide;
8-hydroxy-N-(4-methylphenyl)-N-methylquinoline-5-sulfonamide;
8-hydroxy-N-methyl-N-phenethyl-quinoline-5-sulfonamide;
N-[(4-fluorophenyl)methyl]-8-hydroxy-N-methyl-quinoline-5-sulfonamide;
8-hydroxy-N-methyl-N-[(1R)-1-phenylethyl]quinoline-5-sulfonamide;
8-hydroxy-N-methyl-N-[(1S)-1-phenyl ethyl]quinoline-5-sulfonamide;
N-[(2-fluorophenyl)methyl]-8-hydroxy-N-methyl-quinoline-5-sulfonamide;
N-[(3-chlorophenyl)methyl]-8-hydroxy-N-methyl-quinoline-5-sulfonamide;
8-hydroxy-N-methyl-N-(3-pyridylmethyl)quinoline-5-sulfonamide;
8-hydroxy-N-methyl-N-(2-naphthylmethyl)quinoline-5-sulfonamide;
N-benzyl-N-ethyl-8-hydroxy-quinoline-5-sulfonamide;
N-benzyl-N-(2-dimethylaminoethyl)-8-hydroxy-quinoline-5-sulfonamide;
5-(piperidin-1-yl)sulfonylquinolin-8-ol;
5-(4-morpholin-1-yl)sulfonylquinolin-8-ol;
N-[(4-(trifluoromethyl)phenyl)methyl]-8-hydroxy-N-methyl-quinoline-5-sulfonamide;
N-ethyl-8-hydroxy-N-(4-pyridylmethyl)quinoline-5-sulfonamide;
N,N-diethyl-8-hydroxy-quinoline-5-sulfonamide;
8-hydroxy-N,7-dimethyl-N-[(1R)-1-phenylethyl]quinoline-5-sulfonamide;
7-chloro-8-hydroxy-N-methyl-N-[(1R)-1-phenylethyl]quinoline-5-sulfonamide;
7-bromo-8-hydroxy-N-methyl-N-[(1R)-1-phenylethyl]quinoline-5-sulfonamide; and
7-fluoro-8-hydroxy-N-methyl-N-[(1R)-1-phenylethyl]quinoline-5-sulfonamide.

In some embodiments, the present invention provides prodrugs of the compounds described herein. The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated decacylated, phosphorylated or dephosphorylated to produce the active compounds.

Prodrugs may be prepared by any variety of synthetic methods or appropriate adaptations presented in the chemical literature or as in synthetic or organic chemistry text books, such as those provide in Green's Protective Groups in Organic Synthesis, Wiley, 4$^{th}$ Edition (2007) Peter G. M. Wuts and Theodora W. Green; March's Advanced Organic Chemistry: Reactions, Mechanisms, and Structure, Wiley, 6th Edition (2007) Michael B. Smith and Domino Reactions in Organic Synthesis, Wiley (2006) Lutz F. Tietze, hereby incorporated by reference. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association), also hereby incorporated by reference.

Prodrugs in accordance with the invention can, for example, be produced by replacing appropriate functionalities present in the compounds disclosed herein with certain moieties known to those skilled in the art as 'pro-moieties' as described, for example, in Design of Prodrugs by H. Bundgaard (Elsevier, 1985).

Some non-limiting examples of prodrugs in accordance with the invention include: (i) where the exemplary compound contains a carboxylic acid functionality which is functionalized into a suitably metabolically labile group (esters, carbamates, etc.); (ii) where the exemplary compound contains an alcohol functionality which is functionalized into a suitably metabolically labile group (ethers, esters, carbamates, acetals, ketals, etc.); and (iii) where the exemplary compound contains a primary or secondary amino functionality, or an amide which are functionalized into a suitably metabolically labile group, e.g., a hydrolysable group (amides, carbamates, ureas, phosphonates, sulfonates, etc.). Further examples of replacement groups in accordance with the foregoing examples and examples of other prodrug types may be found in the aforementioned references.

IV. Indications

As discussed above, the COMT-inhibiting compounds of the present invention can be used for treating neuropsychiatric and neurological diseases for which inhibiting COMT provides a therapeutic benefit.

Significant psychiatric indications, as discussed above, include, but are not limited to ADHD, obsessive-compulsive disorder, alcoholism and other addictions, depression, biopolar disorder, age-associated cognitive symptoms, impulse control disorders, including compulsive gambling, sexual behavior, and other compulsive destructive behaviors, in particular, schizophrenia. Among the preferred neurological diseases is treating Parkinson's disease, preferably when co-administered with L-DOPA, with or without a aromatic L-amino acid decarboxylase inhibitor (AADC) such as carbidopa, by preventing COMT-mediated metabolism of L-DOPA.

In one embodiment, a method for treating conditions in which inhibition of COMT enzyme is beneficial comprises administering to a patient in need thereof a COMT-inhibiting compound described hereinabove for use in the present methods. Such conditions include, but are not limited to, those provided in WO 2011/109254, the contents of which are incorporated herein by reference.

In a specific embodiment, a method for treating schizophrenia or psychosis comprises administering to a patient in need thereof a COMT-inhibiting compound described hereinabove for use in the present methods. The Diagnostic and Statistical Manual of Mental Disorders (DSM-IV-TR) (2000, American Psychiatric Association, Washington, D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, a method for treating cognitive disorders comprises administering to a patient in need thereof a COMT-inhibiting compound described hereinabove for use in the present methods. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), mild cognitive impairment, multi-infarct dementia, Lewy body dementia, AIDS-related dementia, and Fronto temporal dementia, delirium, amnestic disorders or age related cognitive decline.

In another specific embodiment, a method for treating anxiety disorders comprises administering to a patient in need thereof a COMT-inhibiting compound described hereinabove for use in the present methods. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, a method for treating substance-related disorders and addictive behaviors comprises administering to a patient in need thereof a COMT-inhibiting compound described hereinabove for use in the present methods. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, a method for treating obesity or eating disorders associated with excessive food intake, and complications associated therewith, comprises administering to a patient in need thereof a COMT-inhibiting compound described hereinabove for use in the present methods. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-10 and DSM-IV-TR and the term is intended to include similar disorders described in other sources. Disorders and conditions encompassed herein include, but are not limited to, obesity, bulimia nervosa and compulsive eating disorders.

In another specific embodiment, a method for treating mood and depressive disorders comprises administering to a patient in need thereof a COMT-inhibiting compound described hereinabove for use in the present methods. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with postpartum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders.

In another specific embodiment, a method for treating pain comprises administering to a patient in need thereof a COMT-inhibiting compound described hereinabove for use in the present methods. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, the COMT-inhibiting compounds described hereinabove for use in the present methods can be used to treat other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with traumatic brain injury, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

In particularly desirable embodiments, the COMT-inhibiting compounds, including the compounds of the present invention, are useful for treating Alzheimer's disease. Accordingly, a method for treating Alzheimer's disease comprises administering to a patient in need thereof a COMT-inhibiting compound described hereinabove for the present methods.

In other particularly desirable embodiments, the COMT-inhibiting compounds, including the compounds of the present invention, are useful for treating Parkinson's disease. Accordingly, a method for treating Parkinson's disease comprises administering to a patient in need thereof a COMT-inhibiting compound described hereinabove for the present methods.

In yet other particularly desirable embodiments, the COMT-inhibiting compounds, including the compounds of the present invention, are useful for treating mild cognitive impairment. Accordingly, a method for treating mild cognitive impairment comprises administering to a patient in need thereof a COMT-inhibiting compound described hereinabove for the present methods.

In still other particularly desirable embodiments, the COMT-inhibiting compounds, including the compounds of the present invention, are useful for treating cognitive, learning and mental related disorders in patients with neurodegeneration associated with traumatic brain injury. Accordingly, a method for treating cognitive, learning and mental related disorders in patients with neurodegeneration associated with traumatic brain injury comprises administering a COMT-inhibiting compound described hereinabove for the present methods.

In further particularly desirable embodiments, the COMT-inhibiting compounds, including the compounds of the present invention, are useful for treating schizophrenia. Accordingly, a method for treating treating schizophrenia comprises administering to a patient in need thereof a COMT-inhibiting compound described hereinabove for the present methods.

The subject COMT-inhibiting compounds, including the compounds of the present invention, are useful in methods for the prevention, treatment, control, amelioration, or reduction of risk of the diseases, disorders and conditions noted herein.

V. Combination Therapies

The subject COMT-inhibiting compounds, including the compounds of the present invention, are further useful in a method for the prevention or treatment of the aforementioned diseases, disorders and conditions in combination with other agents. In many instances, the combination of the drugs together is safer or more effective than either drug alone; the compounds of the present invention and the other active ingredients may often be used in lower doses than when each is used singly. The drug(s) in the combination may be administered contemporaneously or sequentially (i.e. one preceding or following the other, at any appropriate time interval). When administered contemporaneously, the drugs may be administered separately, or a single dosage form may contain both active agents.

Accordingly, the subject compounds may be used in combination with other agents which are known to be beneficial in the subject indications, or other drugs that affect receptors or enzymes that either increase the efficacy, safety, convenience, or reduce unwanted side effects or toxicity of the compounds of the present invention. It will be appreciated that any of the drugs listed herein may be in the form of a pharmaceutically acceptable salt.

In a particularly preferred embodiment, the subject compound is employed in combination with levodopa, with or without a selective extracerebral decarboxylase inhibitor such as carbidopa or benserazide. In other embodiments, the COMT inhibitor of the invention is administered in combination with anticholinergics such as biperiden and trihexyphenidyl (benzhexol) hydrochloride, other COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole.

In another embodiment, the subject compound may be employed in combination with a neuroleptic or antipsychotic agent, or pharmaceutically acceptable salts thereof. Classes of neuroleptic agents include phenothiazines; thioxanthenes; heterocyclic dibenzazepines; butyrophenones; diphenylbutylpiperidines; indolones, such as acepromazine, amisulpride, amoxapine, aripiprazole, asenapine, benperidol, bifeprunox, blonanserin, brexpiprazole, bromperidol, bupropion, busprione, capuride, cariprazine, carpipramine, chlorpromazine, chlorprothixene, clocapramine, clopenthixol, cloperidone, clotiapine, clozapine, cyamemazine, dexclamol, divalproex, dixyrazine, droperidol, flupentixol tiotixene, flupentixol, fluphenazine, fluphenazine, fluspirilene, haloperidol, hydroxyzine, iloperidone, levomepromazine, loxapine, lurasidone, melperone, mesoridazine, molindone, moperone, mosapramine, nefazodone, nemonapride, olanzapine, paliperidone, penfluridol, perazine, pericyazine, perlapine, perospirone, perphenazine, perphenazine, phenelzine, pimavanserin, pimozide, pipamperone, pipotiazine, prochlorperazine, promazine, promethazine, prothipendyl, quetiapine, remoxipride, risperidone, roletamide, sertindole, sulpiride, sultopride, thioproperazine, thioridazine, thiothixene, timiperone, tranylcypromaine, trazodone,trepipam, trifluoperazine, triflupromazine, trimipramine, veralipride, zicronapine, ziprasidone, zotepine, or zuclopenthixol.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, butabarbital, butalbital, capuride, carbocloral, chloral betaine, chloral hydrate, clonazepam, clorazepate, chlordiazepoxide, clorethate, cyprazepam, desipramine, dexclamol, diazepam, dichloralphenazone, divalproex, diphenhydramine, doxepin, estazolam, ethchlorvynol, etomidate, fenobam, flupentixol, fiurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nisobamate, nitrazepam, nortriptyline, oxazepam, paraldehyde, paroxetine, pentobarbital, perlapine, phenelzine, phenobarbital, prazepam, propofol, protriptyline, quazepam, reclazepam, roletamide, secobarbital, sertraline, suproclone, temazepam, tracazolate, tranylcypromaine, trazodone, triazolam, trepipam, tricetamide, triclofos, trimetozine, trimipramine, uldazepam, venlafaxine, zaleplon, zolazepam, or zolpidem.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide; venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

VI. Formulation and Administration

The invention provides a method for administering a COMT inhibiting compound as provided herein to a patient suffering from a condition, or prone to a condition, that is responsive to treatment or prevention with the compound. The method comprises administering, e.g. orally or parenterally, a therapeutically effective amount of the compound, preferably provided as part of a pharmaceutical preparation.

The invention also provides pharmaceutical preparations comprising a COMT-inhibiting compound as provided herein in combination with a pharmaceutical excipient.

Modes of administration include administration by injection, e.g. parenteral, intravenous, intraarterial, intramuscular, subcutaneous, and intrathecal, as well as pulmonary, rectal, transdermal, transmucosal, and oral delivery.

In addition to primates, such as humans, a variety of other mammals can be treated according to the method of the present invention. For instance, mammals including, but not limited to, cows, sheep, goats, horses, dogs, cats, guinea pigs, or other bovine, ovine, equine, canine, feline, or rodent, such as mouse, species can be treated. However, the method can also be practiced in other species, such as avian species (e.g., chickens).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

Suitable formulation types for parenteral administration include ready-for-injection solutions, dry powders for combination with a solvent prior to use, suspensions ready for injection, dry insoluble compositions for combination with a vehicle prior to use, emulsions and liquid concentrates for dilution prior to administration.

The pharmaceutical carrier(s) employed may be solid or liquid. Liquid carriers can be used in the preparation of solutions, emulsions, suspensions and pressurized compositions. The compounds are dissolved or suspended in a pharmaceutically acceptable liquid excipient. Suitable examples of liquid carriers for parenteral administration include, but are not limited to, water (which may contain additives, e.g., cellulose derivatives, preferably sodium carboxymethyl cellulose solution), phosphate buffered saline solution (PBS), alcohols (including monohydric alcohols and polyhydric alcohols, e.g., glycols) and their derivatives, and oils (e.g., fractionated coconut oil and arachis oil). The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators.

Exemplary excipients include, without limitation, carbohydrates, inorganic salts, antimicrobial agents, antioxidants, surfactants, buffers, acids, bases, and combinations thereof. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer including, but not limited to, citric acid, sodium chloride, potassium chloride, sodium sulfate, potassium nitrate, sodium phosphate monobasic, sodium phosphate dibasic, and combinations thereof.

A surfactant may be present as an excipient. Exemplary surfactants include, but are not limited to, polysorbates such as Tween 20 and Tween 80 and pluronics such as F68 and F88 (both available from BASF, Mount Olive, N.J.); sorbitan esters; lipids, such as phospholipids such as lecithin and other phosphatidyl cholines, phosphatidyl ethanolamines (although preferably not in liposomal form), and fatty acids and fatty esters.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof.

For parenteral administration, the carrier can also be an oily ester such as ethyl oleate and isopropyl myristate. Sterile carriers are useful in sterile liquid form compositions for parenteral administration. Sterile liquid pharmaceutical compositions, solutions or suspensions can be utilized by, for example, intraperitoneal injection, subcutaneous injection, intravenously, or topically. The compositions can also be administered intravascularly or via a vascular stent.

For pressurized compositions, the liquid carrier can be a halogenated hydrocarbon or other pharmaceutically acceptable propellant. Such pressurized compositions may also be lipid encapsulated for delivery via inhalation. For administration by intranasal or intrabronchial inhalation or insufflation, the compositions may be formulated into an aqueous or partially aqueous solution, which can then be utilized in the form of an aerosol.

The compositions may be administered topically, as a solution, cream, or lotion, by formulation with pharmaceutically acceptable vehicles containing the active compound. The compositions can be in a form suitable for use in transdermal devices.

The compositions of this invention may be orally administered, in formulations such as capsules, tablets, powders or granules, or as suspensions or solutions in water or non-aqueous media. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

The amount of the compound in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the COMT-inhibiting compound in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then further exploring the range at which optimal performance is attained with no significant adverse effects. Generally, however, the excipient will be present in the composition in an amount of about 1% to about 99% by weight, preferably from about 5%-98% by weight, more preferably from about 15-95% by weight of the excipient, with concentrations less than 30% by weight most preferred.

The foregoing pharmaceutical excipients, along with other excipients, are described in "Remington: The Science & Practice of Pharmacy", 21st ed., Williams & Williams, (2005), the "Physician's Desk Reference", 67th ed., PDR Network, Montvale, N.J. (2013), and Kibbe, A. H., "Handbook of Pharmaceutical Excipients", 7th Edition, Pharmaceutical Press, Washington, D.C., 2012.

The dose of the compounds according to the invention to be administered, both unit dosage and dosing schedule, will vary depend upon the age, weight, and general condition of the subject, as well as the desired therapeutic effect, the route of administration, and the duration of the treatment. The compounds of the invention are administered to the patient in therapeutically effective amounts. Methods are known to those skilled in the art to adjust the dose to obtain maximal benefit. Generally, dosage levels of between 0.001 to 10 mg/kg of body weight daily are administered to the patient. The dosage range will generally be about 0.5 mg to 1.0 g per patient per day, which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. The compounds may be administered on a regimen of 1 to 4 times per day, such as once or twice per day.

These and other aspects of the invention will be realized upon closer inspection of the specification as a whole.

EXAMPLES

The present compounds can be prepared and evaluated according to procedures provided in the following Examples. The following Examples further describe, but do not limit, the scope of the invention.

COMT Inhibition Assay Procedure

The ability of compounds to inhibit the activity of catechol-O-methyltransferase (COMT) was determined by a homogenous time-resolved fluorescent (HTRF) assay (Lina et al, 2012; kit from CisBio, Codolet, France). This assay measures the production of S-adenosyl homocysteine (SAH) from the methyl donor S-adenosyl methionine. Recombinant human membrane bound COMT (MB-COMT; M51A variant) was expressed in HEK 293F cells using 293Fectin (Life Technologies, Gent, Belgium) and membranes prepared. The membranes were re-suspended in buffer (20 mM Tris/HCl pH 7; 10 mM glycerol; 2 mM $MgCl_2$; 10 mM NaCl), aliquoted and stored at –80° C. Recombinant human soluble COMT(S-COMT), Val158 variant and a hexa-His tag on the N-terminus, was purified using Ni-NTA chromatography, the His tag removed and stored in buffer as above.

For the human MB-COMT assay, membranes (62 ng/well) were incubated with SAM (20 µM final, CisBio) and dopamine (1.5 µM final; Sigma H8502, Diegem, Belgium) in the presence or absence of varying concentrations (typically 10 concentrations ranging from 10 µM to 0.1 nM) of compound for 40 min at 37° C. in 384-well microtitre plates (10 µl per well final volume). The reaction was terminated by the addition of acylation buffer and the amount of SAH produced determined according to manufacturer's instructions. Specific inhibition as that inhibited by a high concentration of tolcapone (10 µM; synthesised at UCB) and all experiments were validated using a control curve to tolcapone.

The human S-COMT assay was performed as above except that 0.15 ng enzyme/well was incubated with SAM (20 µM final) and dopamine (100 µM final) for 15 min at 37° C. and SAH production determined.

HTRF readings were performed using a Perkin Elmer Envision and results expressed as concentration of SAH produced using a standard curve. Results were analysed using non-linear regression to the 4-parameter logistic equation and $pIC_{50}$ (–log 10 concentration of drug which inhibits enzyme activity/SAH production by 50%) determined.

As the data herein indicate, a broad variety of compounds of formula I were found effective as COMT inhibitors at low concentrations. $pIC_{50}$ values for exemplary compounds of formula I (see below for compound names and structures) are provided in Table 1 below. Any compound with a $pIC_{50}$ superior or equal to 4.5 in this assay, as described above, is deemed a COMT inhibitor. In the Table 1 below, a single plus (+) is associated with a $pIC_{50}$ of from about 4.5 to 6; two plus signs (++) is associated with a $pIC_{50}$ of from about great than 6 to 7; and three plus signs (+++) is associated with a $pIC_{50}$ of above about 7.

TABLE 1

| Example | Activity range |
|---|---|
| 1 | +++ |
| 2 | +++ |
| 3 | +++ |
| 4 | +++ |
| 5 | +++ |
| 6 | +++ |
| 7 | +++ |
| 8 | ++ |
| 9 | +++ |
| 10 | +++ |
| 11 | +++ |
| 12 | +++ |
| 13 | +++ |
| 14 | +++ |
| 15 | ++ |
| 16 | +++ |
| 17 | ++ |
| 18 | +++ |
| 19 | ++ |
| 20 | +++ |
| 21 | +++ |
| 22 | +++ |
| 23 | +++ |
| 24 | +++ |
| 25 | +++ |
| 26 | +++ |
| 27 | +++ |
| 28 | +++ |
| 29 | +++ |
| 30 | +++ |
| 31 | +++ |
| 32 | ++ |
| 33 | + |
| 34 | ++ |
| 35 | ++ |
| 36 | +++ |
| 37 | ++ |
| 38 | ++ |
| 39 | +++ |
| 40 | +++ |
| 41 | ++ |
| 42 | +++ |
| 43 | +++ |
| 44 | ++ |
| 45 | +++ |
| 46 | ++ |

TABLE 1-continued

| Example | Activity range |
|---|---|
| 47 | +++ |
| 48 | +++ |
| 49 | +++ |
| 50 | +++ |
| 51 | +++ |
| 52 | +++ |
| 53 | +++ |
| 54 | +++ |
| 55 | ++ |
| 56 | +++ |
| 57 | ++ |
| 58 | +++ |
| 59 | +++ |
| 60 | ++ |
| 61 | ++ |
| 62 | +++ |
| 63 | +++ |
| 64 | ++ |
| 65 | +++ |
| 66 | ++ |
| 67 | +++ |
| 68 | ++ |
| 69 | ++ |
| 70 | +++ |
| 71 | +++ |
| 72 | ++ |
| 73 | +++ |
| 74 | +++ |
| 75 | +++ |
| 76 | +++ |
| 77 | +++ |
| 78 | +++ |
| 79 | ++ |
| 80 | ++ |
| 81 | ++ |
| 82 | +++ |
| 83 | +++ |
| 84 | +++ |
| 85 | +++ |
| 86 | +++ |
| 87 | +++ |
| 88 | +++ |
| 89 | ++ |
| 90 | +++ |
| 91 | +++ |
| 92 | ++ |
| 93 | ++ |
| 94 | ++ |
| 95 | + |
| 96 | ++ |
| 97 | ++ |
| 98 | ++ |
| 99 | ++ |
| 100 | ++ |
| 101 | +++ |
| 102 | +++ |
| 103 | ++ |
| 104 | + |
| 105 | ++ |
| 106 | + |
| 107 | ++ |
| 108 | ++ |
| 109 | +++ |
| 110 | +++ |
| 111 | +++ |
| 112 | + |
| 113 | +++ |
| 114 | + |
| 115 | ++ |
| 116 | + |
| 117 | ++ |
| 118 | ++ |
| 119 | ++ |
| 120 | + |
| 121 | + |
| 122 | ++ |
| 123 | +++ |
| 124 | + |
| 125 | + |

Synthetic Procedures

Exemplary compounds were prepared via several general synthetic routes set forth in the Examples below. Any of the disclosed compounds of the present invention can be prepared according to one or more of these synthetic routes or specific examples, or via modifications thereof accessible to the person of ordinary skill in the art.

Example 1

5-tosylquinolin-8-ol—Method A

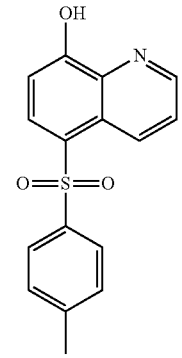 [SMILES: Cc1ccc(S(=O)(=O)c2ccc(O)c3ncccc23)cc1]

Step 1: 5-Iodo-8-((4-methoxybenzyl)oxy)quinoline

To a stirring solution of 5-iodoquinolin-8-ol (4.17 g, 15.38 mmol) in acetonitrile (100 mL), potassium carbonate (4.25 g, 30.8 mmol) was added. The solution was stirred at room temperature for 30 min. 4-methoxybenzyl chloride (2.51 mL, 18.46 mmol) was added. The solution was heated at 80° C. for 4 h. After cooling to room temperature, the solution was filtered. The filter cake was washed with ethyl acetate. The filtrate was concentrated. The residue was purified by Biotage, and eluted with ethyl acetate/hexanes (0-80%) to give the title compound as an off-white solid (1.37 g, 3.51 mmol, 22.8% yield). MS (ES+) m/z 392.0 [M+H]$^+$. $^1$H NMR (400 MHz, DMSO-d6) δ ppm 6.95-7.01 (m, 2 H) 7.15 (d, J=8.34 Hz, 1 H) 7.43-7.49 (m, 2 H) 7.67 (dd, J=8.59, 4.29 Hz, 1 H) 8.06-8.11 (m, 1 H) 8.29 (dd, J=8.46, 1.64 Hz, 1 H) 8.86 (dd, J=4.04, 1.52 Hz, 1 H).

Step 2: 8-((4-Methoxybenzyl)oxy)-5-tosylquinoline

To a stirring solution of 5-iodo-8-((4-methoxybenzyl) oxy)quinolone (0.20 g, 0.511 mmol) in DMSO (1.5 mL), copper(I) iodide (9.74 mg, 0.051 mmol), sodium (S)-pyrrolidine-2-carboxylate (0.014 g, 0.102 mmol) and sodium 4-methylbenzenesulfinate (0.109 g, 0.613 mmol) were added. The solution was heated at 90° C. for 24 hrs. Water (2 mL) was added. The precipitate was isolated by filtration. The crude reaction mixture was purified by Biotage, eluted with ethyl acetate/hexanes (0-80%) to give the title compound as an off-white solid (0.047 g, 0.112 mmol, 21.9% yield). MS (ES+) m/z 420.0 [M+H]+. 1H NMR (400 MHz, chloroform-d) δ ppm 3.79-3.86 (m, 3 H) 5.45 (s, 2 H) 6.88-6.99 (m, 2 H) 7.16 (d, J=8.59 Hz, 1 H) 7.24-7.31 (m, 4 H) 7.45 (d, J=8.59 Hz, 2 H) 7.53 (dd, J=8.84, 4.29 Hz, 1 H) 7.81 (d, J=8.34 Hz, 2 H) 8.42 (d, J=8.34 Hz, 1 H) 9.00 (s, 2 H).

Step 3: 5-tosylquinolin-8-ol 8-((4-methoxybenzyl)oxy)-5-tosylquinoline (0.047 g, 0.112 mmol) was dissolved in TFA (0.863 mL, 11.20 mmol) and stirred at room temperature for 1 hour. The solution was concentrated. The residue was purified by recrystallization in ethyl acetate/hexanes to give the title compound as an off-white solid (30.7 mg, 0.103 mmol, 92% yield). MS (ES+) m/z 300.0 [M+H]+. 1H NMR (400 MHz, DMSO-d6) δ ppm 2.32 (s, 3 H) 7.27 (d, J=8.34 Hz, 1 H) 7.35-7.41 (m, 2 H) 7.73 (dd, J=8.72, 4.17 Hz, 1 H) 7.80-7.86 (m, 2H) 8.39 (d, J=8.34 Hz, 1 H) 8.89 (dd, J=8.72, 1.64 Hz, 1 H) 8.94 (dd, J=4.17, 1.64 Hz, 1 H).

Example 2

5-(4-fluorophenyl)sulfonylquinolin-8-ol—Method B

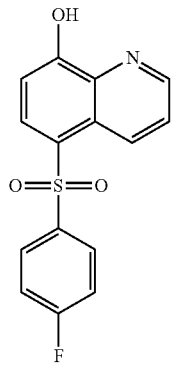 [SMILES: O=S(=O)(c1ccc(F)cc1)c1ccc(O)c2ncccc12]

Step 1: Sodium 8-(benzyloxy)quinoline-5-sulfonate

To a stirring solution of 1N aqueous sodium hydroxide (103 mL, 103 mmol), 8-hydroxyquinoline-5-sulfonic acid hydrate (10 g, 41.1 mmol) was added. The solution was heated to 70° C. After the solution became homogeneous, it was cooled to room temperature. Tetrahydrofuran (100 mL) and benzyl chloride (10.41 mL, 90 mmol) were added. The solution was heated at 75° C. overnight. After cooling to room temperature, the solution was extracted with diethyl ether (2×), then placed in the refrigerator for 4 h. The solid was collected by filtration and dried to give the title compound as a white solid (9.4 g, 67.8% yield). MS (ES+) m/z 314.0 [M−H]−. 1H NMR (400 MHz, D2O) δ ppm 4.63-4.76 (m, 14 H) 5.07 (s, 2 H) 6.90 (d, J=8.34 Hz, 1 H) 7.11-7.25 (m, 3 H) 7.29 (d, J=7.33 Hz, 2 H) 7.52 (dd, J=8.84, 4.29 Hz, 1 H) 7.84 (d, J=8.34 Hz, 1 H) 8.62 (dd, J=4.29, 1.26 Hz, 1 H) 8.82 (dd, J=8.72, 1.39 Hz, 1 H).

Step 2: 8-(Benzyloxy)quinoline-5-sulfonyl chloride

To a stirring solution of sodium 8-(benzyloxy)quinoline-5-sulfonate (8.54 g, 25.3 mmol) in thionyl chloride (55.4 mL, 760 mmol), DMF (10 drops) was added. The solution was heated at 85° C. for 5 h. The solution became homogeneous. The solution was concentrated under vacuum. Toluene (100 mL) was added. The solution was evaporated to dryness. The residue was dried under vacuum to give the title compound as a slightly colored solid (9.8 g, 99% yield). MS (ES+) m/z 334.0 [M+H]+. 1H NMR (400 MHz, DMSO-d6) δ ppm 5.55 (s, 2 H) 7.33-7.53 (m, 3 H) 7.57-7.76 (m, 3 H) 8.14 (d, J=8.34 Hz, 1 H) 8.22 (dd, J=8.59, 5.31 Hz, 1H) 9.18 (dd, J=5.31, 1.52 Hz, 1 H) 9.84 (dd, J=8.72, 1.39 Hz, 1 H).

Step 3: 8-(Benzyloxy)quinoline-5-sulfonyl fluoride

To a stirring solution of 8-(benzyloxy)quinoline-5-sulfonyl chloride (2 g, 5.99 mmol) in acetonitrile (30 mL), potassium fluoride (1.044 g, 17.98 mmol) was added. The solution was stirred at 60° C. for two days. Ethyl acetate (100 mL) was added. The solution was extracted with water (30 mL) (1×), brine (1×), then dried over sodium sulfate. The solution was filtered and concentrated. The residue was purified by Biotage, eluted with ethyl acetate/hexanes (0-80%) to give the title compound as a white solid (1.22 g, 3.83 mmol, 63.9% yield). MS (ES+) m/z 227.0 [M+H]+. 1H NMR (400 MHz, chloroform-d) δ ppm 5.58 (s, 2 H) 7.13 (dd, J=8.59, 0.76 Hz, 1 H) 7.33-7.46 (m, 3 H) 7.49-7.59 (m, 2 H) 7.73 (dd, J=8.72, 4.17 Hz, 1 H) 8.32 (d, J=8.84 Hz, 1 H) 8.83-8.92 (m, 1 H) 9.14 (dd, J=4.17, 1.64 Hz, 1 H).

Step 4: 8-Benzyloxy-5-(4-fluorophenyl)sulfonyl-quinoline

To a stirring solution of 1-fluoro-4-iodo-benzene (0.209 g, 0.95 mmol) in THF (2 mL) at −78° C., n-butyl lithium (2.5 N, 0.38 mL, 0.95 mmol) was added dropwise into the solution. The solution was stirred at −78° C. for 10 min. It was added dropwise into a stirring solution of 8-(benzyloxy)quinoline-5-sulfonyl fluoride (100 mg, 0.315 mmol) in THF (2 mL) at −78° C. The solution was stirred at −78° C. for 1 hour and then room temperature for 60 min. Methanol (1.0 mL) was added. The solution was concentrated. The residue was purified by Biotage, eluted with ethyl acetate/hexane (0-80%) to give the title compound as a white solid (68 mg, 54.8% yield) MS (ES+) m/z 394.0 [M+H]+. 1H NMR (400 MHz, chloroform-d) δ ppm 5.53 (s, 2 H) 7.11-7.19 (m, 3 H) 7.32-7.45 (m, 3 H) 7.49-7.59 (m, 3 H) 7.90-7.98 (m, 2 H) 8.42 (d, J=8.59 Hz, 1 H) 8.95 (dd, J=8.72, 1.64 Hz, 1 H) 9.03 (dd, J=4.17, 1.64 Hz, 1 H).

Step 5: 5-(4-fluorophenyl)sulfonylquinolin-8-ol hydrobromide

To a stirring solution of 8-benzyloxy-5-(4-fluorophenyl)sulfonyl-quinoline (30 mg, 0.076 mmol) in acetic acid (0.1 mL), hydrobromic acid (48%, 0.8 mL, 0.076 mmol) was added. The solution was stirred at 100° C. overnight. The solution was cooled to 0° C. The solution was diluted with diethyl ether. The precipitate was collected by filtration and dried to give the title compound as its HBr salt, a white solid (17.7 mg, 60% yield). MS (ES+) m/z 304.0 [M+H]+. 1H NMR (400 MHz, methanol-d4) δ ppm 7.27-7.48 (m, 2 H) 7.57 (d, J=8.59 Hz, 1 H) 8.08-8.34 (m, 3 H) 8.73 (d, J=8.34 Hz, 1 H) 9.15 (br. s., 1 H) 9.81 (d, J=9.09 Hz, 1 H).

The following compounds were synthesized according Method B:

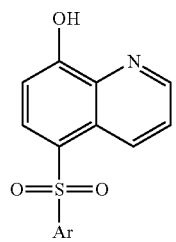

| Example | Name | Ar | Data | Preparation Information |
|---|---|---|---|---|
| 3 | 5-(3,4-dimethyl-phenyl)sulfonyl-quinolin-8-ol | 3,4-dimethylphenyl | MS (ES+) m/z 314.0 [M + H]$^+$. $^1$H NMR (400 MHz, methanol-d4) δ ppm 2.31 (br. s., 6 H) 7.34 (d, J = 6.32 Hz, 1 H) 7.56 (d, J = 7.83 Hz, 1 H) 7.71-7.90 (m, 2 H) 8.23 (d, J = 5.05 Hz, 1 H) 8.71 (d, J = 8.59 Hz, 1 H) 9.13 (br. s., 1 H) 9.81 (d, J = 8.59 Hz, 1 H) | B, Using 4-iodo-1,2-dimethyl-benzene |
| 4 | 5-(3,5-dimethyl-phenyl)sulfonyl-quinolin-8-ol | 3,5-dimethylphenyl | MS (ES+) m/z 314.0 [M + H]$^+$. $^1$H NMR (400 MHz, DMSO-d6) δ ppm 2.30 (s, 6 H) 7.26 (s, 1 H) 7.32 (d, J = 8.34 Hz, 1 H) 7.57 (s, 2 H) 7.81 (dd, J = 8.84, 4.29 Hz, 1 H) 8.43 (d, J = 8.59 Hz, 1 H) 8.95-9.06 (m, 2 H) | B, Using 1-bromo-3,5-dimethyl-benzene |
| 5 | 5-(4-tert-butylphenyl)sulfonyl-quinolin-8-ol | 4-tert-butylphenyl | MS (ES+) m/z 342.0 [M + H]$^+$. $^1$H NMR (400 MHz, DMSO-d6) δ ppm 1.23-1.38 (m, 9 H) 7.35-7.46 (m, 1 H) 7.61-7.74 (m, 2 H) 7.85-8.03 (m, 3 H) 8.4-8.58 (m, 1 H) 9.07 (br. s., 1 H) 9.16 (d, J = 8.34 Hz, 1 H) | B, Using 1-bromo-4-tert-butyl-benzene |
| 6 | 5-(3-phenylphenyl)sulfonyl-quinolin-8-ol | 3-biphenyl | MS (ES+) m/z 362.0 [M+H]$^+$. $^1$H NMR (400 MHz, DMSO-d6) δ ppm 7.35 (d, J = 8.34 Hz, 1 H) 7.39-7.46 (m, 1 H) 7.46-7.54 (m, 2 H) 7.63-7.72 (m, 3 H) 7.87 (dd, J = 8.84, 4.29 Hz, 1 H) 7.95 (d, J = 7.58 Hz, 2 H) 8.18 (s, 1 H) 8.55 (d, J = 8.59 Hz, 1 H) 8.99 (d, J = 4.29 Hz, 1 H) 9.14 (d, J = 8.84 Hz, 1H) | B, Using 1-bromo-3-phenyl-benzene |
| 7 | 5-(m-tolylsulfonyl)quinolin-8-ol | 3-methylphenyl | MS (ES+) m/z 300.0 [M + H]$^+$. $^1$H NMR (400 MHz, DMSO-d6) δ ppm 2.35 (s, 3 H) 7.29 (d, J = 8.34 Hz, 1 H) 7.40-7.51 (m, 2 H) 7.71-7.81 (m, 3 H) 8.42 (d, J = 8.34 Hz, 1 H) 8.87-9.01 (m, 2 H) | B, Using 1-bromo-3-methyl-benzene |
| 8 | 5-(3,5-dichlorophenyl)sulfonyl-quinolin-8-ol | 3,5-dichlorophenyl | MS (ES+) m/z 355.0 [M + H]$^+$. $^1$H NMR (400 MHz, DMSO-d6) δ ppm 7.30 (d, J = 8.59 Hz, 1 H) 7.77-7.83 (m, 1 H) 7.95-7.99 (m, 1 H) 8.03 (d, J = 1.77 Hz, 2 H) 8.50 (d, J = 8.34 Hz, 1 H) 8.94-9.01 (m, 2 H) | B, Using 1-bromo-3,5-dichloro-benzene |
| 9 | 5-(4-chlorophenyl)sulfonyl-quinolin-8-ol | 4-chlorophenyl | MS (ES+) m/z 320.0 [M + H]$^+$. $^1$H NMR (400 MHz, DMSO-d6) δ ppm 7.32 (d, J = 8.59 Hz, 1 H) 7.65 (d, J = 8.34 Hz, 2 H) 7.79 (dd, J = 8.84, 4.29 Hz, 1 H) 7.98 (d, J = 8.34 Hz, 2 H) 8.45 (d, J = 8.34 Hz, 1 H) 8.90-9.02 (m, 2 H) | B, Using 1-bromo-4-chloro-benzene |

-continued

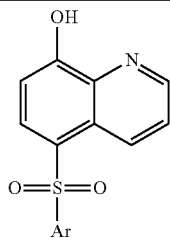

| Example | Name | Ar | Data | Preparation Information |
|---|---|---|---|---|
| 10 | 5-(2,4-dimethyl-phenyl)sulfonyl-quinolin-8-ol | 2,4-dimethylphenyl | MS (ES+) m/z 314.0 [M + H]$^+$.<br>$^1$H NMR (400 MHz, DMSO-d6) δ ppm 2.26 (s, 3 H) 2.30 (s, 3 H) 7.10-7.19 (m, 1 H) 7.27-7.37 (m, 2 H) 7.71 (dd, J = 8.84, 4.29 Hz, 1 H) 8.07-8.18 (m, 1 H) 8.39 (d, J = 8.34 Hz, 1 H) 8.71 (dd, J = 8.84, 1.52 Hz, 1 H) 8.94 (dd, J = 4.17, 1.39 Hz, 1 H) | B, Using 1-bromo-2,4-dimethyl-benzene |
| 11 | 5-[4-(trifluoro-methyl)phenyl]sulfonyl-quinolin-8-ol | 4-(trifluoromethyl)phenyl | MS (ES+) m/z 354.0 [M + H]$^+$.<br>$^1$H NMR (400 MHz, DMSO-d6) δ ppm 7.33 (d, J = 8.34 Hz, 1 H) 7.77 (dd, J = 8.84, 4.29 Hz, 1 H) 7.96 (d, J = 8.34 Hz, 2 H) 8.18 (d, J = 8.34 Hz, 2 H) 8.49 (d, J = 8.34 Hz, 1 H) 8.91 (dd, J = 8.84, 1.52 Hz, 1 H) 8.97 (dd, J = 4.17, 1.39 Hz, 1 H) | B, Using 1-bromo-4-(trifluoromethyl)benzene |
| 12 | 5-(2-naphthyl-sulfonyl)quinolin-8-ol | 2-naphthyl | MS (ES+) m/z 336.0 [M + H]$^+$.<br>$^1$H NMR (400 MHz, DMSO-d6) δ ppm 7.33 (d, J = 8.34 Hz, 1 H) 7.64-7.76 (m, 3 H) 7.78-7.83 (m, 1 H) 7.97-8.03 (m, 1 H) 8.04-8.10 (m, 1 H) 8.20-8.25 (m, 1 H) 8.48-8.56 (m, 1 H) 8.82 (d, J = 1.77 Hz, 1 H) 8.93 (dd, J = 4.29, 1.52 Hz, 1 H) 8.99-9.07 (m, 1 H) | B, Using 2-bromo-naphthalene |
| 13 | 5-[3-(trifluoro-methyl)phenyl]sulfonyl-quinolin-8-ol | 3-(trifluoromethyl)phenyl | MS (ES+) m/z 354.0 [M + H]$^+$.<br>$^1$H NMR (400 MHz, DMSO-d6) δ ppm 7.32 (d, J = 8.34 Hz, 1 H) 7.76-7.87 (m, 2 H) 8.06 (d, J = 7.33 Hz, 1 H) 8.24-8.31 (m, 2 H) 8.51 (d, J = 8.59 Hz, 1 H) 8.93-9.01 (m, 2 H) | B, Using 1-bromo-3-(trifluoromethyl)benzene |
| 14 | 5-(3-chlorophenyl)sulfonyl-quinolin-8-ol | 3-chlorophenyl | MS (ES+) m/z 320.0 [M + H]$^+$. | B, Using 1-bromo-3-chloro-benzene |
| 15 | 5-(3,4-dichlorophenyl)sulfonyl-quinolin-8-ol | 3,4-dichlorophenyl | MS (ES+) m/z 355.0 [M + H]$^+$.<br>$^1$H NMR (400 MHz, DMSO-d6) δ ppm 7.31 (d, J = 8.59 Hz, 1 H) 7.77-7.87 (m, 2 H) 7.91-7.96 (m, 1 H) 8.25 (d, J = 2.27 Hz, 1 H) 8.48 (d, J = 8.59 Hz, 1 H) 8.94-9.01 (m, 2 H) | B, Using 4-bromo-1,2-dichloro-benzene |
| 16 | 5-(2-pyridylsulfonyl)quinolin-8-ol | 2-pyridyl | MS (ES+) m/z 287.0 [M + H]$^+$.<br>$^1$H NMR (400 MHz, DMSO-d6) δ ppm 7.34 (d, J = 8.59 Hz, 1 H) 7.66 (ddd, J = 7.64, 4.74, 1.01 Hz, 1 H) 7.81-7.88 (m, 1 H) 8.16 (td, J = 7.77, 1.64 Hz, 1 H) 8.31 (dt, J = 8.02, 0.92 Hz, 1 H) 8.42 (d, J = 8.34 Hz, 1 H) 8.59-8.64 (m, 1 H) 8.97-9.03 (m, 1 H) 9.14 (dd, J = 8.84, 1.52 Hz, 1 H) | B, Using 2-bromopyridine |

-continued

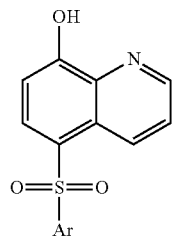

| Example | Name | Ar | Data | Preparation Information |
|---|---|---|---|---|
| 17 | 5-(4-pyridylsulfonyl)quinolin-8-ol | 4-pyridyl | MS (ES+) m/z 287.0 [M + H]⁺.<br>¹H NMR (400 MHz, DMSO-d6) δ ppm 7.33 (d, J = 8.34 Hz, 1 H) 7.78 (dd, J = 8.84, 4.04 Hz, 1 H) 7.89-7.95 (m, 2 H) 8.48 (d, J = 8.34 Hz, 1 H) 8.8 -8.87 (m, 2 H) 8.89 (dd, J = 8.72, 1.39 Hz, 1 H) 8.98 (dd, J = 4.17, 1.14 Hz, 1 H) | B, Using 4-iodopyridine |
| 18 | 5-(4-methoxyphenyl)sulfonyl-quinolin-8-ol | 4-methoxyphenyl | MS (ES+) m/z 316.0 [M + H]⁺.<br>¹H NMR (400 MHz, DMSO-d6) δ ppm 3.79 (s, 3 H) 7.04-7.12 (m, 2 H) 7.26 (d, J = 8.34 Hz, 1 H) 7.73 (dd, J = 8.72, 4.17 Hz, 1 H) 7.86-7.92 (m, 2H) 8.37 (d, J = 8.34 Hz, 1 H) 8.87-8.98 (m, 2 H) | B, Using 1-bromo-4-methoxy-benzene |
| 19 | 5-(3-pyridylsulfonyl)quinolin-8-ol | 3-pyridyl | MS (ES+) m/z 287.0 [M + H]⁺.<br>¹H NMR (400 MHz, DMSO-d6) δ ppm 7.32 (d, J = 8.34 Hz, 1 H) 7.62 (ddd, J = 8.15, 4.86, 0.88 Hz, 1 H) 7.80 (dd, J = 8.84, 4.29 Hz, 1 H) 8.35-8.41 (m, 1 H) 8.49 (d, J = 8.34 Hz, 1 H) 8.82 (dd, J = 4.80, 1.52 Hz, 1 H) 8.95-9.04 (m, 2 H) 9.17-9.21 (m, 1 H) | B, Using 3-bromopyridine |
| 20 | 5-(4-fluoro-2-methyl-phenyl)sulfonyl-quinolin-8-ol | 4-fluoro-2-methylphenyl | MS (ES+) m/z 318.0 [M + H]⁺.<br>¹H NMR (400 MHz, DMSO-d6) δ ppm 2.32 (s, 3 H) 7.26 (dd, J = 9.85, 2.53 Hz, 1 H) 7.29-7.34 (m, 1 H) 7.34-7.38 (m, 1 H) 7.72 (dd, J = 8.72, 4.17 Hz, 1 H) 8.31 (dd, J = 8.84, 5.81 Hz, 1 H) 8.40 (d, J = 8.34 Hz, 1 H) 8.70 (dd, J = 8.72, 1.39 Hz, 1 H) 8.95 (dd, J = 4.29, 1.52 Hz, 1 H) | B, Using 1-bromo-4-fluoro-2-methyl-benzene |
| 21 | 5-[2-(trifluoromethyl)phenyl]sulfonyl-quinolin-8-ol | 2-(trifluoromethyl)phenyl | MS (ES+) m/z 314.0 [M + H]⁺.<br>¹H NMR (400 MHz, DMSO-d6) δ ppm 7.28-7.39 (m, 1 H) 7.67-7.79 (m, 1 H) 7.82-7.97 (m, 2 H) 7.99-8.16 (m, 2 H) 8.32 (d, J = 8.59 Hz, 1 H) 8.60-8.70 (m, 1 H) 8.97 (dd, J = 4.29, 1.52 Hz, 1 H) | B, Using 1-bromo-2-(trifluoromethyl)benzene |
| 22 | 5-(benzenesulfonyl)quinolin-8-ol | phenyl | MS (ES+) m/z 285.9 [M + H]⁺.<br>¹H NMR (400 MHz, DMSO-d6) δ ppm 7.27-7.34 (m, 1 H) 7.54-7.69 (m, 3 H) 7.73-7.80 (m, 1 H) 7.92-8.00 (m, 2 H) 8.41-8.47 (m, 1 H) 8.90-9.00 (m, 2 H) | B, Using iodobenzene |

Example 23

5-[3-(4-pyridyl)phenyl]sulfonylquinolin-8-ol—Method C

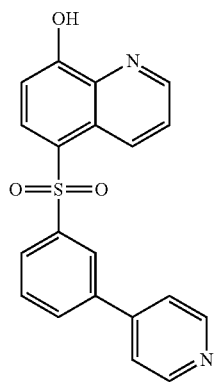 [SMILES: O=S(=O)(c1cccc(-c2ccncc2)c1)c1ccc(O)c2ncccc12]

Step 1: 8-Benzyloxy-5-(3-bromophenyl)sulfonyl-quinoline

Following Method B, step 4, and substituting 1-fluoro-4-iodo-benzene with 1-bromo-3-iodobenzene (0.63 mmol), the title compound was obtained as a white solid (0.39 g, 21% yield). MS (ES+) m/z 455.0 [M+H]$^+$. $^1$H NMR (400 MHz, chloroform-d) δ ppm 5.54 (s, 2 H) 7.17 (d, J=8.59 Hz, 1 H) 7.32-7.48 (m, 4 H) 7.49-7.62 (m, 3 H) 7.63-7.73 (m, 1 H) 7.85 (ddd, J=7.83, 1.77, 1.01 Hz, 1 H) 8.04 (t, J=1.89 Hz, 1 H) 8.44 (d, J=8.34 Hz, 1 H) 8.90-8.99 (m, 1 H) 9.04 (dd, J=4.17, 1.64 Hz, 1 H).

Step 2: 8-Benzyloxy-5-[3-(4-pyridyl)phenyl]sulfonyl-quinoline

To a stirring solution of 8-benzyloxy-5-(3-bromophenyl)sulfonyl-quinoline (92 mg, 0.20 mmol) and 4-pyridylboronic acid (37 mg, 0.30 mmol) in dioxane (1 mL), sodium carbonate solution (1 M, 0.60 mL, 0.61 mmol) and Pd(dppf)Cl$_2$.CH$_2$Cl$_2$ (8.0 mg, 0.01 mmol) were added. Water (0.5 mL) was added afterward. The contents were heated at 100° C. for 2 h. The reaction mixture was filtered and transferred to Gilson HPLC for purification to give the title compound as a black solid (62 mg, 67% yield). MS (ES+) m/z 453.0 [M+H]$^+$. $^1$H NMR (400 MHz, chloroform-d) δ ppm 5.51 (s, 2 H) 7.37-7.46 (m, 3 H) 7.49-7.58 (m, 2 H) 7.63-7.78 (m, 2 H) 7.85-7.97 (m, 3 H) 8.12 (d, J=7.07 Hz, 1 H) 8.24 (s, 1 H) 8.55 (d, J=8.59 Hz, 1 H) 8.93 (d, J=6.06 Hz, 2 H) 9.06-9.15 (m, 2 H).

Step 3: 5-[3-(4-pyridyl)phenyl]sulfonylquinolin-8-ol dihydrobromide

Following Method B, step 5, and substituting 8-benzyloxy-5-(4-fluorophenyl)sulfonyl-quinoline with 8-benzyloxy-5-[3-(4-pyridyl)phenyl]sulfonyl-quinoline (0.13 mmol), the title compound was obtained as an off-white solid (26 mg, 37% yield). MS (ES+) m/z 363.0 [M+H]$^+$. $^1$H NMR (400 MHz, DMSO-d6) δ ppm 7.33 (d, J=8.34 Hz, 1 H) 7.73-7.87 (m, 2 H) 8.13-8.20 (m, 1 H) 8.23-8.29 (m, 1 H) 8.43-8.50 (m, 2H) 8.51-8.58 (m, 2 H) 8.94-8.99 (m, 1 H) 9.00-9.09 (m, 3 H).

The following compounds were synthesized using Method C:

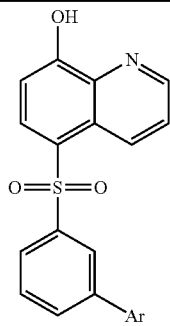

| Example | Name | Ar | Data | Preparation Information |
|---|---|---|---|---|
| 24 | 5-[3-(3-chloro-4-fluorophenyl)phenyl]sulfonyl-quinolin-8-ol | 3-chloro-4-fluorophenyl | MS (ES+) m/z 413.9 [M + H]$^+$. $^1$H NMR (400 MHz, DMSO-d6) δ ppm 7.28 (d, J = 8.34 Hz, 1 H) 7.50-7.59 (m, 1 H) 7.63-7.70 (m, 1 H) 7.71-7.79 (m, 2 H) 7.91-8.03 (m, 3 H) 8.24 (s, 1 H) 8.49 (d, J = 8.59 Hz, 1 H) 8.94 (d, J = 4.29 Hz, 1 H) 9.00 (d, J = 8.84 Hz, 1 H) | C, Using 3-chloro-4-fluorobenzene-boronic acid |
| 25 | 5-[3-(5-quinolyl)phenyl]sulfonl-quinolin-8-ol | 5-quinolyl | MS (ES+) m/z 413.0 [M + H]$^+$. $^1$H NMR (400 MHz, DMSO-d6) δ ppm 7.32 (d, J = 8.59 Hz, 1 H) 7.73 (d, J = 8.08 Hz, 1 H) 7.81 (dt, J = 8.65, 4.14 Hz, 1 H) 7.86 (d, J = 7.58 Hz, 1 H) 7.88-7.94 (m, 7 H) 8.02-8.15 (m, 13 H) 8.16-8.24 (m, 2 H) 8.49 (d, J = 8.34 Hz, 1 H) 8.62 (d, J = 8.34 Hz, 1 H) 8.73 (s, 1 H) 9.01 (dd, J = 4.17, 1.39 Hz, 1 H) 9.03-9.10 (m, 1 H) 9.93 (s, 1 H) | C, Using 5-quinoline-boronic acid |

-continued

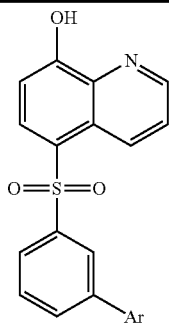

| Example | Name | Ar | Data | Preparation Information |
|---|---|---|---|---|
| 26 | 5-[3-(1H-indazol-4-yl)phenyl]sulfonyl-quinolin-8-ol | | MS (ES+) m/z 402.0 [M + H]+. 1H NMR (400 MHz, DMSO-d6) δ ppm 7.27 (d, J = 7.07 Hz, 1 H) 7.34 (d, J = 8.34 Hz, 1 H) 7.43-7.50 (m, 1 H) 7.62 (d, J = 8.34 Hz, 1 H) 7.72-7.79 (m, 1 H) 7.84 (dd, J = 8.84, 4.29 Hz, 1 H) 7.93 (s, 1 H) 8.03 (t, J = 7.71 Hz, 2 H) 8.19 (s, 1 H) 8.54 (d, J = 8.34 Hz, 1 H) 8.99 (dd, J = 4.29, 1.26 Hz, 1H) 9.11 (d, J = 9.09 Hz, 1 H) | C, Using 1H-indazol-4-ylboronic acid |

Example 27

5-[(3-methyl-4-pyridyl)sulfonyl]quinolin-8-ol—Method D

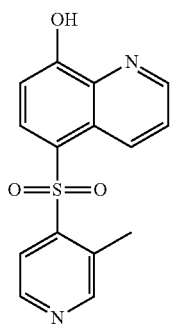 [SMILES: Cc1cnccc1S(=O)(=O)c1ccc(O)c2ncccc12]

Step 1: 8-benzyloxy-5-[(3-methyl-4-pyridyl)sulfanyl]quinolone

To a stirring solution of 8-benzyloxyquinoline-5-sulfonyl chloride (100 mg, 0.30 mmol) in THF (2 mL) with stirring, triphenylphosphine (236 mg, 0.90 mmol) was added. The solution was heated at 60° C. for 50 min. The solution was cooled to room temperature. Diethyl ether (1.5 mL) was added. The precipitate was isolated by filtration and dried. The residue was dissolved in dioxane (2 mL). $Pd_2(dba)_3$ (6.8 mg, 0.007 mmol), 4-bromo-3-methyl-pyridine (62 mg, 0.36 mmol), DIPEA (0.11 mL, 0.60 mmol) were added. The solution was heated at 110° C. overnight. The solution was transferred to Gilson HPLC for purification to provide the title compound (TFA salt) as a colorless oil (41.5 mg, 38% yield). MS (ES+) m/z 359.0 [M+H]+. 1H NMR (400 MHz, chloroform-d) δ ppm 2.65 (s, 3 H) 5.51 (s, 2 H) 6.60 (d, J=6.32 Hz, 1 H) 7.34 (d, J=8.34 Hz, 1 H) 7.38-7.48 (m, 3 H) 7.53-7.60 (m, 2 H) 7.74 (dd, J=8.59, 4.55 Hz, 1 H) 7.96 (d, J=8.34 Hz, 1 H) 8.17 (d, J=6.32 Hz, 1 H) 8.53-8.58 (m, 2 H) 9.22 (dd, J=4.55, 1.52 Hz, 1 H).

Step 2: 8-benzyloxy-5-[(3-methyl-4-pyridyl)sulfonyl]-1-oxido-quinolin-1-ium

To a stirring solution of 8-benzyloxy-5-[(3-methyl-4-pyridyl)sulfanyl]quinolone (70 mg, 0.19 mmol) in methanol (1.5 mL)/water (0.5 mL), oxone monopersulfate (300 mg, 0.49 mmol) was added. The solution was stirred at room temperature overnight. The solution was transferred to Gilson HPLC for purification to give the title compound as a white solid (26 mg, 32% yield). MS (ES+) m/z 407.0 [M+H]+. 1H NMR (400 MHz, DMSO-d6) δ ppm 2.21 (s, 3 H) 5.45 (s, 2 H) 7.36-7.51 (m, 3 H) 7.54-7.62 (m, 3H) 7.67-7.76 (m, 1 H) 8.11-8.18 (m, 1 H) 8.24-8.32 (m, 2 H) 8.51 (d, J=8.59 Hz, 1 H) 8.61-8.69 (m, 1 H) 8.97 (dd, J=4.04, 1.52 Hz, 1 H).

Step 3: 8-benzyloxy-5-[(3-methyl-4-pyridyl)sulfonyl]quinolone

To a stirring solution of 8-benzyloxy-5-[(3-methyl-4-pyridyl)sulfonyl]-1-oxido-quinolin-1-ium (17.6 mg, 0.04 mmol) in methanol (1 mL), ammonium formate (5.4 mg, 0.087 mmol) and Raney nickel (10 mg) were added. The solution was heated at 50° C. overnight. The solution was filtered and transferred Gilson HPLC for purification to give the title compound as a white solid (15 mg, 89% yield). MS (ES+) m/z 391.0 [M+H]+. 1H NMR (400 MHz, chloroform-d) δ ppm 2.52 (s, 3 H) 5.51 (s, 2 H) 7.28 (s, 1 H) 7.31-7.38 (m, 1 H) 7.38-7.48 (m, 3 H) 7.52 (dd, J=7.58,1.52 Hz, 2 H) 7.72 (dd, J=8.84, 4.29 Hz, 1 H) 8.07 (d, J=5.31 Hz, 1 H) 8.57 (d, J=8.59 Hz, 1 H) 8.64 (s, 1 H) 8.77 (d, J=5.31 Hz, 1 H) 8.90 (dd, J=8.84, 1.26 Hz, 3 H) 9.12-9.20 (m, 1 H).

Step 4: 5-[(3-methyl-4-pyridyl)sulfonyl]quinolin-8-ol

Following Method B, step 5, substituting 8-benzyloxy-5-(4-fluorophenyl)sulfonyl-quinoline with 8-benzyloxy-5-[(3-methyl-4-pyridyl)sulfonyl]quinolone (0.038 mmol), the title compound was obtained as an off-white solid (5 mg, 31% yield). MS (ES+) m/z 301.0 [M+H]+. 1H NMR (400 MHz, DMSO-d6) δ ppm 2.33 (s, 3 H) 7.33 (d, J=8.59 Hz, 1 H) 7.70 (dd, J=8.72, 4.17 Hz, 1 H) 8.01 (d, J=5.31 Hz, 1 H) 8.46 (d, J=8.34 Hz, 1H) 8.59-8.66 (m, 2 H) 8.73 (d, J=5.05 Hz, 1 H) 8.95 (dd, J=4.17, 1.64 Hz, 1 H).

Example 28

5-[1-[(2-chlorophenyl)methyl]benzimidazol-4-yl]sulfonylquinolin-8-ol—Method E

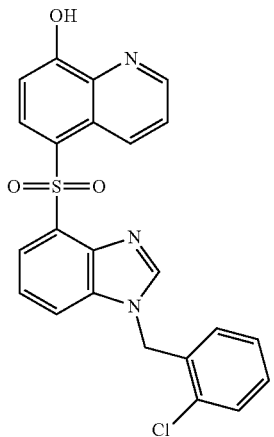 [SMILES: O=S(=O)(c1ccc(O)c2ncccc12)c1cccc2c1ncn2Cc1ccccc1Cl]

Step 1: N-[(2-chlorophenyl)methyl]-3-fluoro-2-nitro-aniline

To a stirring solution of 2,6-difluoro nitrobenzene (3.83 g, 24 mmol) in acetonitrile (50 mL), 2-chlorobenzylamine (2.9 mL, 24 mmol) and DIPEA (5.1 mL, 28.9 mmol) were added. The solution was stirred at room temperature overnight. Water (100 mL) was added and the solution was extracted with ethyl acetate (3×50 mL). The combined organic solution was extracted with water (50 mL), brine (50 mL) and dried over sodium sulfate. The solution was filtered and concentrated. The residue was purified by ISCO, eluting with ethyl acetate/hexane (0-20%) to give the title compound as a purple solid (2.87 g, 43% yield). MS (ES+) m/z 281.0 [M+H]+. 1H NMR (400 MHz, chloroform-d) δ ppm 4.56-4.65 (m, 2 H) 6.44-6.55 (m, 2 H) 7.22-7.37 (m, 3 H) 7.40-7.52 (m, 1 H) 7.62 (br. s., 1H).

Step 2: 3-[(8-benzyloxy-5-quinolyl)sulfanyl]-N1-[(2-chlorophenyl)methyl]benzene-1,2-diamine Following Method D, step 1, and substituting 4-bromo-3-methyl-pyridine with N-[(2-chlorophenyl)methyl]-3-fluoro-2-nitro-aniline (5.1 mmol), 3-[(8-benzyloxy-5-quinolyl)sulfanyl]-N-[(2-chlorophenyl)methyl]-2-nitro-aniline (red solid, 138 mg, 6% yield) and the title compound (white solid, 100 mg, 5% yield) were obtained. MS (ES+) m/z 498.0 [M+H]+. 1H NMR (400 MHz, chloroform-d) δ ppm 4.06 (br. s., 2 H) 4.44 (br. s., 2 H) 5.40-5.49 (m, 2 H) 6.59-6.66 (m, 1 H) 6.71 (t, J=7.83 Hz, 1 H) 6.80-6.86 (m, 1 H) 6.92 (d, J=8.59 Hz, 1 H) 7.12-7.19 (m, 1 H) 7.21-7.25 (m, 1 H) 7.33-7.64 (m, 9 H) 8.69 (dd, J=8.59, 1.77 Hz, 1 H) 9.03 (dd, J=4.17, 1.89 Hz, 1 H).

Step 3: 8-benzyloxy-5-[1-[(2-chlorophenyl)methyl]benzimidazol-4-yl]sulfanyl-quinoline 3-[(8-benzyloxy-5-quinolyl)sulfanyl]-N1-[(2-chlorophenyl)methyl]benzene-1,2-diamine was dissolved in formic acid and heated at 100° C. overnight. The solution was concentrated. The residue was purified by Gilson HPLC to give the title compound (TFA salt) as a slightly colored solid (87 mg, 87% yield). MS (ES+) m/z 509.0 [M+H]+. 1H NMR (400 MHz, chloroform-d) δ ppm 5.45 (s, 2 H) 5.57 (s, 2 H) 6.70 (d, J=7.83 Hz, 1 H) 7.14-7.21 (m, 2 H) 7.26-7.43 (m, 6 H) 7.46-7.52 (m, 2 H) 7.55 (d, J=6.82 Hz, 2 H) 7.75 (dd, J=8.59, 4.80 Hz, 1H) 7.95-8.02 (m, 1 H) 8.80 (s, 1H) 9.11 (d, J=8.59 Hz, 1 H) 9.23 (d, J=4.04 Hz, 1 H).

Step 4: 8-benzyloxy-5-[1-[(2-chlorophenyl)methyl]benzimidazol-4-yl]sulfonyl-quinoline To a stirring solution of 8-benzyloxy-5-[1-[(2-chlorophenyl)methyl]benzimidazol-4-yl]sulfanyl-quinoline (80 mg, 0.16 mmol) in dichloromethane (5 mL), mCPBA (77.6 mg, 0.31 mmol) was added. The solution was stirred at room temperature for 1 hour. The solution was concentrated. The residue was purified by Gilson HPLC to give the title compound (TFA salt) as a white solid (45.8 mg, 54% yield). MS (ES+) m/z 541.0 [M+H]+. 1H NMR (400 MHz, DMSO-d6) δ ppm 5.42 (s, 2 H) 5.58 (s, 2 H) 5.77 (s, 1 H) 7.03 (dd, J=7.58, 1.52 Hz, 1 H) 7.23-7.29 (m, 1 H) 7.30-7.53 (m,6 H) 7.54-7.66 (m, 4 H) 7.83-7.89 (m, 1 H) 8.15 (d, J=7.07 Hz, 1 H) 8.43 (s, 1 H) 8.74 (d, J=8.34 Hz, 1 H) 8.86 (dd, J=4.04, 1.52 Hz, 1 H) 8.93(dd, J=8.72, 1.64 Hz, 1 H).

Step 5: 5-[1-[(2-chlorophenyl)methyl]benzimidazol-4-yl]sulfonylquinolin-8-ol dihydrobromide To a stirring solution of 8-benzyloxy-5-[1-[(2-chlorophenyl)methyl]benzimidazol-4-yl]sulfonyl-quinoline (42 mg, 0.078 mmol) in formic acid (0.2 mL), HBr (48%, 0.8 mL) was added. The solution was heated at 100° C. for 1 hour. The solution was concentrated. The residue was washed with ethyl acetate and dried to give the title compound as white solid (45 mg, 94% yield). MS (ES+) m/z 450.0 [M+H]+. 1H NMR (400 MHz, DMSO-d6) δ ppm 5.59 (s, 2 H) 7.07 (dd, J=7.58, 1.77 Hz, 1 H) 7.22-7.30 (m, 1 H) 7.31-7.40 (m, 2 H) 7.46-7.55 (m, 2 H)7.75 (dd, J=8.84, 4.29 Hz, 1 H) 7.87 (dd, J=8.21, 0.88 Hz, 1 H) 8.10-8.18 (m, 1 H) 8.53 (s, 1 H) 8.71 (d, J=8.59 Hz, 1 H) 8.92 (dd, J=4.29, 1.52 Hz, 1 H) 9.07-9.13 (m, 1 H).

Example 29

5-[2-(p-tolyl)ethylsulfonyl]quinolin-8-ol—Method F

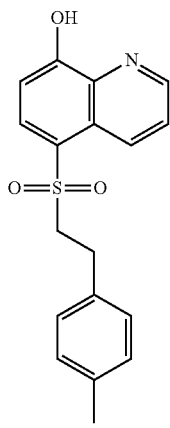 [SMILES: Cc1ccc(CCS(=O)(=O)c2ccc(O)c3ncccc23)cc1]

Step 1: 8-benzyloxy-5-[2-(p-tolyl)ethylsulfanyl]quinoline

To a stirring solution of 8-benzyloxyquinoline-5-sulfonyl chloride (100 mg, 0.30 mmol) in THF (2 mL) with stirring, triphenylphosphine (236 mg, 0.90 mmol) was added. The solution was heated at 60° C. for 30 min. The solution was cooled to room temperature. Diethyl ether (1.5 mL) was added. The precipitate was isolated by filtration and dried. Tetrahydrofuran (2 mL) was added followed by sodium borohydride (11 mg, 0.30 mmol). The solution was stirred at room temperature 30 min. Diethyl ether (2 mL) was added. The solvents were removed. The residue was dried and then dissolved in THF (2 mL)/DMF (1 mL). Sodium hydride (18 mg, 60%, 0.45 mmol) was added followed by 4-Methylphenethyl bromide (59 mg, 0.30 mmol). The solution was heated to 80° C. for 3 hrs. The solution was transferred on Gilson HPLC for purification to give the title compound as purple solid (36 mg, 31% yield). MS (ES+) m/z 386.0 [M+H]+. 1H NMR (400 MHz, chloroform-d) δ ppm 2.32 (s, 3 H) 2.84 (t, J=7.58 Hz, 2 H) 3.12 (t, J=7.58 Hz, 2 H) 5.45 (s, 2 H) 6.97-7.03 (m, 2 H) 7.05-7.11 (m, 2 H) 7.22-7.25 (m, 1 H) 7.32 -7.45 (m, 3 H) 7.54-7.61 (m, 2 H) 7.79-7.86 (m, 2 H) 9.16 (d, J=8.84 Hz, 1 H) 9.33 (d, J=3.79 Hz, 1 H).

Step 2: 8-benzyloxy-5-[2-(p-tolyl)ethylsulfonyl]quinoline

To a stirring solution of 8-benzyloxy-5-[2-(p-tolyl)ethylsulfanyl]quinoline (35 mg, 0.09 mmol) in dichloromethane (2 mL), mCPBA (46 mg, 0.19 mmol) was added. The solution was stirred at room temperature for 60 min. The solution was concentrated. The residue was purified by Gilson HPLC to give the title compound as white solid (25.6 mg, 65% yield). MS (ES+) m/z 418.0 [M+H]+. 1H NMR (400 MHz, chloroform-d) δ ppm 2.06-2.35 (m, 3 H) 3.00 (br. s., 2 H) 3.48 (br. s., 2 H) 5.53 (br. s., 2 H) 6.82-7.08 (m, 4 H) 7.33-7.62 (m, 6 H) 7.76 (br. s., 1 H) 8.33 (d, J=8.59 Hz, 1 H) 9.11-9.30 (m, 2 H).

Step 3: 5-[2-(p-tolyl)ethylsulfonyl]quinolin-8-ol hydrobromide

To a stirring solution of 8-benzyloxy-5-[2-(p-tolyl)ethylsulfonyl]quinolone (24 mg, 0.06 mmol) in acetic acid (0.1 mL), hydrobromic acid (48%, 1 mL) was added. The solution was stirred at 100° C. for 4 hrs. The solution was cooled to room temperature. The solution was diluted with diethyl ether. The precipitate was collected by filtration and dried to give the title compound as a HBr salt, a white solid (19 mg, 81% yield). MS (ES+) m/z 328.0 [M+H]+. 1H NMR (400 MHz, DMSO-d6) δ ppm 2.13-2.22 (s, 3 H) 2.77-2.88 (m, 2 H) 3.62-3.72 (m, 2 H) 6.89-7.01 (m, 4 H) 7.20-7.29 (m, 1 H) 7.83 (dd, J=8.59, 4.29 Hz, 1 H) 8.11-8.20 (m, 1 H) 8.97-9.09 (m, 2 H).

The following compounds were synthesized using Method F:

| Example | Name | R1 | Data | Preparation Information |
|---|---|---|---|---|
| 30 | 5-cyclohexyl-sulfonyl-quinolin-8-ol | 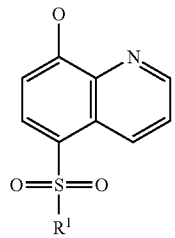 | MS (ES+) m/z 292.0 [M + H]+. 1H NMR (400 MHz, DMSO-d6) δ ppm 0.99-1.25 (m, 3 H) 1.26-1.41 (m, 2 H) 1.56 (d, J = 12.13 Hz, 1 H) 1.72 (d, J = 12.63 Hz, 2 H) 1.84 (d, J = 11.87 Hz, 2 H) 3.15-3.30 (m, 1 H) 7.30 (d, J = 8.34 Hz, 1 H) 7.87 (dd, J = 8.84, 4.29 Hz, 1 H) 8.12 (d, J = 8.34 Hz, 1 H) 9.04 (dd, J = 4.29, 1.01 Hz, 1 H) 9.13 (d, J = 8.59 Hz, 1 H) | F, Using iodocyclohexane |

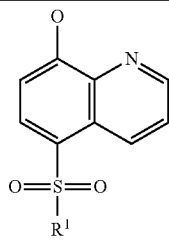

| Example | Name | R¹ | Data | Preparation Information |
|---|---|---|---|---|
| 31 | 5-cyclopentyl-sulfonyl-quinolin-8-ol | | MS (ES+) m/z 278.0 [M + H]⁺. ¹H NMR (400 MHz, DMSO-d6) δ ppm 1.47-1.60 (m, 2 H) 1.60-1.80 (m, 4 H) 1.81-1.92 (m, 2 H) 3.82 (dt, J = 15.16, 7.58 Hz, 1 H) 7.27 (dd, J = 8.46, 2.15 Hz, 1 H) 7.80-7.92 (m, 1 H) 8.16 (dd, J = 8.08, 1.77 Hz, 1 H) 9.01-9.05 (m, 1 H) 9.09 (br. s., 1 H) | F, Using cyclopentyl iodide |
| 32 | 5-(p-tolylmethyl-sulfonyl) quinolin-8-ol | | MS (ES+) m/z 314.0 [M + H]⁺ | F, Using 4-fluorobenzyl bromide |
| 33 | 5-ethylsulfonyl quinolin-8-ol | | MS (ES+) m/z 238.0 [M + H]⁺ 1H NMR (400 MHz. DMSO-d6) δ ppm 1.00-1.14 (m, 12 H) 3.31-3.44 (m, 2 H) 7.26-7.35 (m, 4 H) 7.90 (dd, J = 8.84, 4.29 Hz, 4 H) 8.14-8.23 (m, 4 H) 9.06 (dd, J = 4.55, 1.52 Hz, 4 H) 9.11 (dd, J = 8.84, 1.26 Hz, 4 H) | F |

Example 34

5-(4-piperidylsulfonyl)quinolin-8-ol—Method G

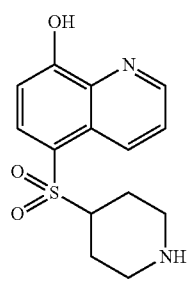 [SMILES: O=S(=O)(c1ccc(O)c2ncccc12)C1CCNCC1]

Step 1: tert-butyl 4-[(8-benzyloxy-5-quinolyl)sulfonyl]piperidine-1-carboxylate Following Method F, steps 1 and 2, and substituting 4-methylphenethyl bromide with tert-butyl 4-iodopiperidine-1-carboxylate (12.58 mmol), the title compound was obtained as a colorless oil (1.39 g, 25% yield). MS (ES+) m/z 483.0 [M+H]⁺. ¹H NMR (400 MHz, chloroform-d) δ ppm 1.44 (s, 9 H) 1.60 (s, 2 H) 1.67-1.80 (m, 2 H) 2.03-2.11 (m, 2 H) 3.12 (tt, J=11.91, 3.63 Hz, 2 H) 5.54 (s, 2 H) 7.15 (d, J=8.34 Hz, 1 H) 7.33-7.46 (m, 3 H) 7.50-7.58 (m, 2 H) 7.66 (dd, J=8.72, 4.17 Hz, 1 H) 8.18 (d, J=8.34 Hz, 1 H) 9.07-9.19 (m, 2 H).

Step 2: 5-(4-piperidylsulfonyl)quinolin-8-ol; 2,2,2-trifluoroacetic acid

To a stirring solution of tert-butyl 4-[(8-benzyloxy-5-quinolyl)sulfonyl]piperidine-1-carboxylate (1.03 g, 2.1 mmol) in dichloromethane (15 mL), TFA (15 mL) was added. The solution was stirred at room temperature for 1 h. The solution was concentrated. The residue was dissolved in water (50 mL). Sodium hydroxide solution (1 N, 10 mL) was added until a white precipitate was produced, then extracted with dichloromethane (3×40 mL). The combined dichloromethane solution was extracted with brine (1×40 mL), dried over sodium sulfate, filtered and concentrated to give the title compound (8.2 mg, 24% yield) as an off-white solid. MS (ES+) m/z 383.0 [M+H]⁺. ¹H NMR (400 MHz, DMSO-d6) δ ppm 1.42 (qd, J=12.08, 4.17 Hz, 2 H) 1.68 (d, J=10.36 Hz, 2 H) 2.29-2.41 (m, 2 H) 2.93 (d, J=12.13 Hz, 2 H) 3.29-3.42 (m, 3 H) 5.42 (s, 2 H) 7.37-7.49 (m, 3 H) 7.53 (d, J=8.59 Hz, 1 H) 7.58 (d, J=7.07 Hz, 2 H) 7.78 (dd, J=8.84, 4.29 Hz, 1 H) 8.17 (d, J=8.59 Hz, 1 H) 8.98-9.06 (m, 2 H).

Step 3: 5-(4-piperidylsulfonyl)quinolin-8-ol

To a stirring solution of tert-butyl 4-[(8-benzyloxy-5-quinolyl)sulfonyl]piperidine-1-carboxylate (35 mg, 0.065 mmol) in acetic acid (0.05 mL), hydrobromic acid (48%, 0.6 mL) was added. The solution was heated at 100° C. for 50 min to give a black solution, which was cooled to room temperature and transferred to Gilson HPLC for purification to give the title compound as a TFA salt (8.2 mg, 24% yield). MS (ES+) m/z 293.0 [M+H]⁺. ¹H NMR (400 MHz, methanol-d4) δ ppm 1.28-1.40 (m, 2 H) 1.92-2.08 (m, 2 H) 2.19 (d, J=13.14 Hz, 2 H) 3.01 (t, J=11.37 Hz, 2 H) 3.23(q, J=7.33 Hz, 1 H) 7.35 (d, J=8.34 Hz, 1 H) 7.85-7.95 (m, 1 H) 8.30 (d, J=8.34 Hz, 1 H) 9.04(d, J=4.55 Hz, 1 H) 9.32 (d, J=8.34 Hz, 1 H).

Example 35

5-[[1-[(4-fluorophenyl)methyl]-4-piperidyl]sulfonyl]quinolin-8-ol

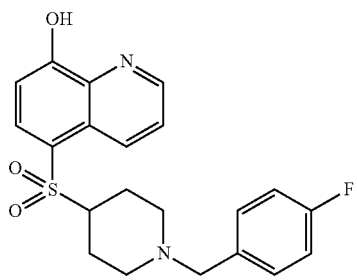 [SMILES: O=S(=O)(c1ccc(O)c2ncccc12)C1CCN(Cc2ccc(F)cc2)CC1]

Step 1: 8-benzyloxy-5-[[1-[(4-fluorophenyl)methyl]-4-piperidyl]sulfonyl]quinoline To a stirring mixture of 8-benzyloxy-5-(4-piperidylsulfonyl)quinoline (55 mg, 0.14 mmol) and 4-fluorobenzaldehyde (21 mg, 0.17 mmol) in dichloromethane (3 mL) and THF (3 mL), a few drops of acetic acid was added. The resulting solution was heated briefly to dissolve the starting material and cooled to room temperature. Sodium triacetoxylborohydride (60.9 mg, 0.29 mmol) was added. The solution was stirred at room temperature overnight. The solution was concentrated. The residue was purified by Gilson HPLC to give the title compound as a white solid (TFA salt) (54.6 mg, 77% yield). MS (ES+) m/z 491.0 [M+H]⁺. ¹H NMR (400 MHz, DMSO-d6) δ ppm 1.76-1.93 (m, 2 H) 1.99-2.13 (m, 2 H) 2.87 (br. s., 1 H) 3.43 (d, J=12.13 Hz, 2 H) 3.65 (t, J=12.25 Hz, 2 H) 4.24 (br. s., 2 H) 5.43 (s, 2 H) 7.23-7.36 (m, 3 H) 7.36-7.63 (m, 8 H) 7.80 (dd, J=8.72, 4.17 Hz, 1 H) 8.19 (d, J=8.34 Hz, 1 H) 8.93-9.08 (m, 2 H).

Step 2: 5-[[1-[(4-fluorophenyl)methyl]-4-piperidyl]sulfonyl]quinolin-8-ol

To a stirring solution of 8-benzyloxy-5-[[1-[(4-fluorophenyl)methyl]-4-piperidyl]sulfonyl]quinoline (54 mg, 0.11 mmol) in acetic acid (0.05 mL), hydrobromic acid (48%, 0.6 mL) was added. The solution was heated at 100° C. for 60 min. The solution was concentrated. The residue was washed with diethyl ether and dried to give the title compound as a white solid, as its hydrobromide salt (48 mg, 79% yield). MS (ES+) m/z 401.1 [M+H]⁺. ¹H NMR (400 MHz, DMSO-d4) δ ppm 1.81-1.96 (m, 2 H) 2.04 (d, J=12.63 Hz, 2 H) 2.81-2.96 (m, 2 H) 3.43 (d, J=12.38 Hz, 2 H) 3.57-3.70 (m, 1 H) 4.27 (d, J=4.55 Hz, 2 H) 7.24-7.37 (m, 3 H) 7.53 (dd, J=8.59, 5.31 Hz, 2 H) 7.89 (dd, J=8.84, 4.29 Hz, 1 H) 8.14 (d, J=8.59 Hz, 1 H) 9.03-9.15 (m, 2 H).

Example 36

5-[[1-[(2,3-dichlorophenyl)methyl]-4-piperidyl]sulfonyl]quinolin-8-ol

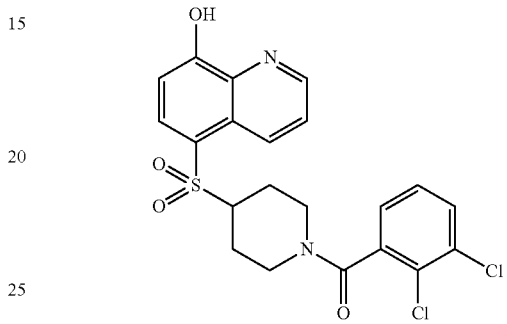

Step 1: [4-[(8-benzyloxy-5-quinolyl)sulfonyl]-1-piperidyl]-(2,3-dichlorophenyl)methanone To a stirring mixture of 8-benzyloxy-5-(4-piperidylsulfonyl)quinoline (52 mg, 0.14 mmol), 2,3-dichlorobenzoic acid (39 mg, 0.20 mmol) and DIPEA (0.048 mL, 0.27 mmol) in DMF (1 mL), HBTU (61.9 mg, 0.16 mmol) was added. The solution was stirred at room temperature overnight. The solution was transferred to Gilson HPLC for purification to give the title compound as a white solid, TFA salt (33 mg, 43% yield). MS (ES+) m/z 555 [M+H]⁺. ¹H NMR (400 MHz, DMSO-d6) δ ppm 1.46-1.68 (m, 2 H) 1.79 (t, J=13.14 Hz, 1 H) 1.93 (t, J=10.36 Hz, 1 H) 2.78 (t, J=12.25 Hz, 1 H) 3.03 (m, 2 H) 3.30 (d, J=13.14 Hz, 1 H) 3.61-3.76 (m, 1 H) 4.56 (d, J=7.33 Hz, 1 H) 5.43 (s, 2 H) 7.29 (dd, J=7.58, 1.52 Hz, 1 H) 7.35-7.63 (m, 7H) 7.69 (ddd, J=7.89, 4.23, 1.77 Hz, 1 H) 7.76-7.89 (m, 1 H) 8.19 (dd, J=8.34, 6.32 Hz, 1 H) 8.98-9.10 (m, 2 H).

Step 2: 5-[[1-[(2,3-dichlorophenyl)methyl]-4-piperidyl]sulfonyl]quinolin-8-ol

Following Method G, step 3, substituting tert-butyl 4-[(8-benzyloxy-5-quinolyl)sulfonyl]piperidine-1-carboxylate with [4-[(8-benzyloxy-5-quinolyl)sulfonyl]-1-piperidyl]-(2,3-dichlorophenyl)methanone (0.059 mmol), the title compound was obtained as a TFA salt (15 mg, 18% yield). MS (ES+) m/z 451.0 [M+H]⁺. ¹H NMR (400 MHz, DMSO-d6) δ ppm 1.86 (d, J=12.38 Hz, 2 H) 2.04 (d, J=12.63 Hz, 2 H) 3.06 (br. s., 2 H) 3.36-3.72 (m, 3 H) 4.42 (br. s., 2 H) 7.27 (d, J=8.59 Hz, 1 H) 7.44-7.55 (m, 1 H) 7.60 (d, J=7.33 Hz, 1 H) 7.73-7.94 (m, 2 H) 8.10 (d, J=8.84 Hz, 1 H) 8.95-9.14 (m, 2 H).

Example 37

5-[[1-(4-fluorophenyl)-4-piperidyl]sulfonyl]quinolin-8-ol

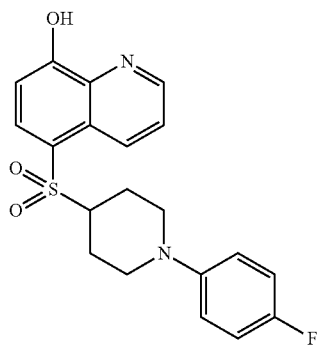 [SMILES: O=S(=O)(c1ccc(O)c2ncccc12)C1CCN(c2ccc(F)cc2)CC1]

Step 1: 8-benzyloxy-5-[[1-(4-fluorophenyl)-4-piperidyl]sulfonyl]quinolone

To a stirring mixture of 8-benzyloxy-5-(4-piperidylsulfonyl)quinoline (53 mg, 0.14 mmol), 4-fluoroidobenzene (61 mg, 0.28 mmol), potassium carbonate (38 mg, 0.28 mmol), CuI (2.6 mg, 0.014 mmol) in DMSO (1.5 mL), L-proline sodium (3.8 mg, 0.028 mmol) was added. The solution was heated at 90° C. for 40 hrs. The solution was cooled to room temperature, filtered and purified by Gilson HPLC to give the title compound as its TFA salt (18 mg, 27% yield). MS (ES+) m/z 477.1 [M+H]$^+$. $^1$H NMR (400 MHz, methanol-d4) δ ppm 2.00-2.21 (m, 3 H) 2.64-2.73 (m, 2 H) 3.09 (t, J=12.13 Hz, 2 H) 3.71 (d, J=11.87 Hz, 2 H) 5.57(s,2 H) 7.09-7.19 (m, 2 H) 7.26 (dd, J=8.84, 4.55 Hz, 2 H) 7.34-7.47 (m, 4 H) 7.54-7.66 (m, 4 H) 8.38 (d, J=8.59 Hz, 1 H) 9.45(d, J=8.59 Hz, 1 H).

Step 2: 5-[[1-(4-fluorophenyl)-4-piperidyl]sulfonyl]quinolin-8-ol

Following Method G, step 3, substituting tert-butyl 4-[(8-benzyloxy-5-quinolyl)sulfonyl]piperidine-1-carboxylate with 8-benzyloxy-5-[[1-(4-fluorophenyl)-4-piperidyl]sulfonyl] (0.059 mmol), the title compound was obtained as TFA salt (5.3 mg, 22% yield). MS (ES+) m/z 387.0 [M+H]$^+$. $^1$H NMR (400 MHz, methanol-d4) δ ppm 2.33-2.47 (m, 8 H) 3.47-3.90 (m, 1 H) 7.30-7.43 (m, 2 H) 7.52-7.63 (m, 1 H) 7.71 (dd, J=9.22,4.17 Hz, 2 H) 8.31 (dd, J=8.97, 5.18 Hz, 1 H) 8.53 (d, J=8.59 Hz, 1 H) 9.18-9.28 (m, 1 H) 9.88 (d, J=8.59 Hz, 1 H).

The following compounds were made according the same method:

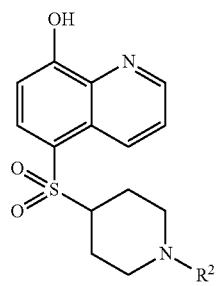

| Example | Name | R2 | Data | Preparation Information |
|---|---|---|---|---|
| 38 | 5-[[1-[(2,3-dichlorophenyl)methyl]-4-piperidyl]sulfonyl]quinolin-8-ol | Cl, Cl-phenyl-CH$_2$– | MS (ES+) m/z 451.0 [M + H]$^+$. $^1$H NMR (400 MHz, DMSO-d6) δ ppm 1.86 (d, J = 12.38 Hz, 2 H) 2.04 (d, J = 12.63 Hz, 2 H) 3.06 (br. s., 2 H) 3.36-3.72 (m, 3 H) 4.42 (br. s., 2 H) 7.27 (d, J = 8.59 Hz, 1 H) 7.44-7.55 (m, 1 H) 7.60 (d, J = 7.33 Hz, 1 H) 7.73-7.94 (m, 2 H) 8.10 (d, J = 8.84 Hz, 1 H) 8.95-9.14 (m, 2 H) | G, Using 2,3-dichlorobenzaldehyde |
| 39 | 5-[[1-(2,3-dimethylphenyl)-4-piperidyl]sulfonyl]quinolin-8-ol | 2,3-dimethylphenyl | MS (ES+) m/z 397.0 [M + H]$^+$. $^1$H NMR (400 MHz, methanol-d4) δ ppm 2.16 (br. s., 3 H) 2.28 (d, J = 9.35 Hz, 6 H) 3.04 (br. s., 1 H) 7.10 (d, J = 8.59 Hz, 3 H) 7.39 (d, J = 8.34 Hz, 1 H) 7.95 (dd, J = 8.72, 4.67 Hz, 1 H) 8.36 (d, J = 8.34 Hz, 1 H) 9.07 (dd, J = 4.55, 1.52 Hz, 1 H) 9.45 (d, J = 9.09 Hz, 1 H) | G, Using 3-iodo-o-xylene |

Example 40

5-(3,4-dihydro-1H-isoquinolin-2-ylsulfonyl)quinolin-8-ol—Method I

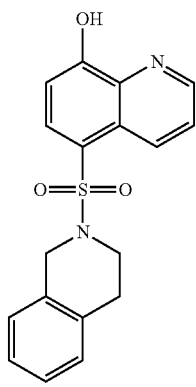 [SMILES: O=S(=O)(c1ccc(O)c2ncccc12)N1CCc2ccccc2C1]

Step 1: 8-hydroxyquinoline-5-sulfonyl chloride 8-hydroxyquinoline-5-sulfonic acid hydrate (3.11 g, 12.8 mmol) was suspended in thionyl chloride (10 mL, 137 mmol) and DMF (49.5 µL, 0.64 mmol). The suspension was stirred at 70° C. for 14 h. After cooling, the solvent was removed in vacuo followed by addition of toluene and further solvent removal in vacuo (2×) to give 8-hydroxyquinoline-5-sulfonyl chloride (3.08 g, 12.6 mmol, 98% yield) as a yellow solid. $^1$H NMR (400 MHz, DMSO-d6) δ ppm 9.80 (dd, J=8.72, 1.39 Hz, 1 H) 9.10 (dd, J=5.31, 1.52 Hz, 1 H) 8.15 (dd, J=8.84, 5.30 Hz, 1 H) 8.09 (d, J=8.08 Hz, 1 H) 7.38 (d, J=8.08 Hz, 1 H).

Step 2: 5-(3,4-dihydro-1H-isoquinolin-2-ylsulfonyl)quinolin-8-ol

To a solution of 1,2,3,4-tetrahydroisoquinoline (109 mg, 103 µL, 0.41 mmol) in DCM (2 mL) was added triethylamine (125 mg, 172 µL, 1.23 mmol). To this solution was added 8-hydroxyquinoline-5-sulfonyl chloride (100 mg, 0.41 mmol) in portions over 1 h. The reaction mixture was allowed to stir overnight, then the balance of the material was added over 1 h. After stirring 1 h after final addition of sulfonyl chloride, the reaction mixture was applied directly to a 10 g silica gel cartridge and purified by automated normal-phase chromatography (2-20% MeOH/DCM). The product-containing fractions were combined and the solvent removed in vacuo to give 5-(3,4-dihydro-1H-isoquinolin-2-ylsulfonyl)quinolin-8-ol (33 mg, 0.097 mmol, 24% yield) as a tan solid. MS (ES+) m/z 341.0 [M+H]$^+$. $^1$H NMR (400 MHz, DMSO-d6) δ ppm 8.99 (dd, J=8.72, 1.64 Hz, 1 H) 8.96 (dd, J=4.30, 1.52 Hz, 1 H) 8.18 (d, J=8.34 Hz, 1 H) 7.74 (dd, J=8.72, 4.17 Hz, 1 H) 7.21 (d, J=8.59 Hz, 1 H) 7.11 (d, J=3.03 Hz, 3 H) 7.05-7.09 (m, 1 H) 4.30 (s, 2 H) 3.43 (t, J=5.94 Hz, 2 H) 2.78 (t, J=5.94 Hz, 2 H).

Example 41

5-(4-phenylpiperazin-1-yl)sulfonylquinolin-8-ol—Method J

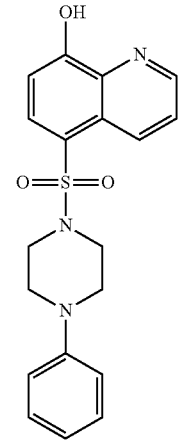 [SMILES: O=S(=O)(c1ccc(O)c2ncccc12)N1CCN(c2ccccc2)CC1]

To a suspension of 8-hydroxyquinoline-5-sulfonyl chloride (50 mg, 0.21 mmol) in DCM (1 mL) was added N,O-bis(trimethylsilyl)acetamide (63 mg, 75 µL, 0.31 mmol). The contents were stirred 15 min at room temperature, then a solution of 1-phenylpiperazine (50 mg, 0.31 mmol) and triethylamine (31 mg, 43 µL, 0.31 mmol) in DCM (1 mL) was added. The resulting mixture was stirred at room temperature for 2 h. The reaction mixture was treated with 2 mL saturated NaHCO$_3$, agitated vigorously, then eluted through a phase separator tube. The collected DCM fraction was applied directly to a 10 g silica gel cartridge and purified by automated normal-phase chromatography (2-25% MeOH/CH$_2$Cl$_2$). The product-containing fractions were combined and the solvent removed in vacuo to give 5-(4-phenylpiperazin-1-yl)sulfonylquinolin-8-ol (20 mg, 0.049 mmol, 24% yield) as a light green solid. MS (ES+) m/z 370.0 [M+H]$^+$. $^1$H NMR (400 MHz, DMSO-d6) δ ppm 9.04 (dd, J=8.84, 1.52 Hz, 1 H) 8.99 (dd, J=4.04, 1.52 Hz, 1 H) 8.13 (d, J=8.34 Hz, 1 H) 7.79 (dd, J=8.84, 4.04 Hz, 1 H) 7.21-7.26 (m, 2 H) 7.18 (dd, J=8.72, 7.20 Hz, 2 H) 6.87 (dd, J=8.84, 1.01 Hz, 2 H) 6.75-6.81 (m, 1 H) 3.48-3.54 (m, 1 H) 3.07-3.16 (m, 7 H).

Example 42

8-hydroxy-N-[(3-methoxyphenyl)methyl]-N-methylquinoline-5-sulfonamide—Method K

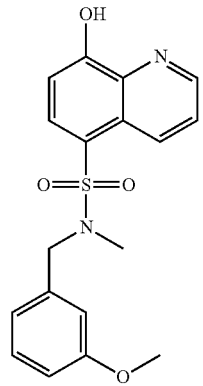 [SMILES: COc1cccc(CN(C)S(=O)(=O)c2ccc(O)c3ncccc23)c1]

Step 1: 8-fluoroquinoline-5-sulfonyl chloride 8-fluoroquinoline (2.24 g, 15.22 mmol) was added dropwise with stirring to chlorosulfonic acid (10 mL, 150.45 mmol). The resulting mixture was stirred at 100° C. for 16 h, 125° C. for 6 h, then 100° C. for 26 h. Reaction complete by LCMS. Carefully added the reaction mixture dropwise to ice-water with stirring. Collected solid by filtration and air-dried to give 8-fluoroquinoline-5-sulfonyl chloride (2.61 g, 70% yield) as a white solid. MS (ES+) m/z 246.0 [M+H]+. $^1$H NMR (400 MHz, DMSO-d6) δ ppm 9.36 (d, J=8.59 Hz, 1 H) 9.04 (d, J=3.28 Hz, 1 H) 8.02 (dd, J=8.08, 5.31 Hz, 1 H) 7.82 (dd, J=8.72, 4.42 Hz, 1 H) 7.62 (dd, J=10.61, 8.08 Hz, 1 H).

Step 2: 8-tert-butoxy-N-[(3-methoxyphenyl) methyl]-N-methyl-quinoline-5-sulfonamide 8-fluoroquinoline-5-sulfonyl chloride (50 mg, 0.20 mmol) was dissolved in THF (1 mL). To this solution was added a solution of 3-methoxy-N-methylbenzylamine (31 mg, 36 μL, 0.20 mmol) and DIPEA (70.9 μL, 0.41 mmol) in THF (0.50 mL). The resulting mixture was stirred at room temperature for 5 min. Complete conversion to intermediate fluoroquinoline sulfonamide by LCMS. Added potassium t-butoxide (68.5 mg, 0.61 mmol) and stirred at ambient temperature overnight. The reaction mixture was treated with 2 mL water and 2 mL DCM, agitated vigorously, then eluted through a phase separator tube. The collected DCM fraction was purified directly by automated normal-phase chromatography (12-100% EtOAc/hexanes, 10 g silica gel cartridge). The product-containing fractions were combined and the solvent removed in vacuo to give 8-tert-butoxy-N-[(3-methoxyphenyl)methyl]-N-methyl-quinoline-5-sulfonamide (28 mg, 0.068 mmol, 33% yield) as a colorless oil. MS (ES+) m/z 415.0 [M+H]+. $^1$H NMR (400 MHz, DMSO-d6) δ ppm 9.02 (dd, J=4.04, 1.52 Hz, 1 H) 8.95 (dd, J=8.84, 1.77 Hz, 1 H) 8.17 (d, J=8.34 Hz, 1 H) 0.74 (dd, J=8.72, 4.17 Hz, 1 H) 7.54 (d, J=8.34 Hz, 1 H) 7.20-7.26 (m, 1 H) 6.79-6.86 (m, 2 H) 6.71-6.74 (m, 1 H) 4.29 (s, 2 H) 3.64 (s, 3 H) 2.66 (s, 3 H) 1.54 (s, 9 H).

Step 3: 8-hydroxy-N-[(3-methoxyphenyl)methyl]-N-methyl-quinoline-5-sulfonamide 4M HCl in dioxane (0.5 mL, 2 mmol) was added to 8-tert-butoxy-N-[(3-methoxyphenyl)methyl]-N-methyl-quinoline-5-sulfonamide (25 mg, 0.060 mmol) and stirred at ambient temperature for 2 h. Complete conversion to product by LCMS. Added Et$_2$O, collected solid by filtration, washed with Et$_2$O and air-dried to give 8-hydroxy-N-[(3-methoxyphenyl)methyl]-N-methyl-quinoline-5-sulfonamide hydrochloride (19.2 mg, 0.049 mmol, 81% yield) as a yellow solid. MS (ES+) m/z 359.0 [M+H]+. $^1$H NMR (400 MHz, DMSO-d6) δ ppm 9.00-9.11 (m, 2 H) 8.18 (d, J=8.34 Hz, 1 H) 7.85 (dd, J=8.84, 4.29 Hz, 1 H) 7.19-7.29 (m, 2 H) 6.78-6.87 (m, 2 H) 6.72 (s, 1 H) 4.24 (s, 2 H) 3.65 (s, 3 H) 2.61 (s, 3 H).

Example 43

5-(4-benzylpiperazin-1-yl)sulfonylquinolin-8-ol— Method L

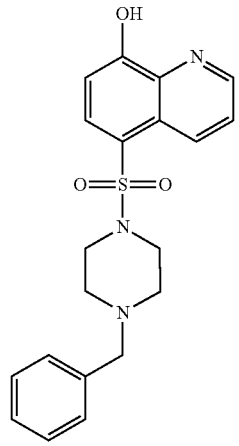 [SMILES: O=S(=O)(c1ccc(O)c2ncccc12)N1CCN(Cc2ccccc2)CC1]

Step 1: 2-[[5-(4-benzylpiperazin-1-yl)sulfonyl-8-quinolyl]oxy]ethyl-trimethyl-silane 8-fluoroquinoline-5-sulfonyl chloride (50 mg, 0.20 mmol) was suspended in THF (1 mL). To this suspension was added DIPEA (70.9 μL, 0.41 mmol), followed by 1-benzylpiperazine (36 mg, 36 μL, 0.20 mmol). The resulting mixture was stirred at room temperature for 15 min. A suspension of 2-(trimethylsilyl)ethanol (0.15 mL, 1.02 mmol) and 60% sodium hydride (40.71 mg, 1.02 mmol) in THF (1 mL) were added and the resulting mixture was stirred at ambient temperature for 30 min. Water was added and the mixture extracted with CHCl$_3$. The organic layer was concentrated in vacuo, and the residue purified by automated normal-phase chromatography (0-100% EtOAc/hexanes, 4 g silica gel cartridge). The product-containing fractions were combined, and the solvent removed in vacuo to give 2-[[5-(4-benzylpiperazin-1-yl)sulfonyl-8-quinolyl]oxy]ethyl-trimethyl-silane (75.6 mg, 0.156 mmol, 77% yield) as a colorless syrup. MS (ES+) m/z 484.2 [M+H]+. $^1$H NMR (400 MHz, DMSO-d6) δ ppm 9.08 (dd, J=8.84, 1.52 Hz, 1 H) 9.02 (dd, J=4.04, 1.52 Hz, 1 H) 8.19 (d, J=8.59 Hz, 1 H) 7.56 (dd, J=8.84, 4.04 Hz, 1 H) 7.20-7.31 (m, 5 H) 7.05 (d, J=8.59 Hz, 1 H) 4.40-4.47 (m, 2 H) 3.45 (s, 2 H) 3.13 (br. s., 4 H) 2.43-2.49 (m, 4 H) 1.41-1.47 (m, 2 H) 0.13-0.17 (m, 9 H).

Step 2: 5-(4-benzylpiperazin-1-yl)sulfonylquinolin-8-ol

To a solution of 2-[[5-(4-benzylpiperazin-1-yl)sulfonyl-8-quinolyl]oxy]ethyl-trimethyl-silane (53.4 mg, 0.11 mmol) in DMF (0.50 mL) was added cesium fluoride (50.3 mg, 0.33 mmol). The contents were stirred at 60° C. for 3 h. The reaction mixture was cooled to room temperature and diluted with EtOAc. The resulting mixture was then washed with water (3×), brine, dried with MgSO$_4$, filtered and the solvent removed in vacuo to give 5-(4-benzylpiperazin-1-yl)sulfonylquinolin-8-ol (23.6 mg, 0.062 mmol, 56% yield) as a beige solid. MS (ES+) m/z 384.2 [M+H]+. $^1$H NMR (400 MHz, DMSO-d6) δ ppm 11.11 (br. s, 1 H) 8.98 (dd, J=6.44, 1.14 Hz, 2 H) 8.07 (d, J=8.59 Hz, 1 H) 7.73-7.78 (m, 1 H) 7.17-7.29 (m, 6 H) 3.41 (s, 2 H) 2.99 (br. s., 4 H) 2.36 (br. s., 4 H).

The following compounds were synthesized using one of the previous methods:

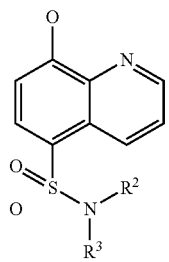

| Ex. | —NR²R³ | Name | Data | Prep Info |
|---|---|---|---|---|
| 44 | (4-methylbenzyl)NH— | 8-hydroxy-N-(4-methylbenzyl)quinoline-5-sulfonamide | MS (ES+) m/z 329.0 [M + H]⁺<br>¹H NMR (400 MHz, DMSO-d6) δ ppm 8.93-9.00 (m, 2 H) 8.29 (br. s., 1 H) 8.03 (d, J = 8.34 Hz, 1 H) 7.69-7.76 (m, 1 H) 7.09 (d, J = 8.34 Hz, 1 H) 6.88-6.97 (m, 5 H) 3.90 (s, 2 H) 2.18 (s, 3 H) | I |
| 45 | N-benzyl-N-methyl | N-benzyl-8-hydroxy-N-methylquinoline-5-sulfonamide | MS (ES+) m/z 329.0 [M + H]⁺<br>¹H NMR (400 MHz, DMSO-d6) δ ppm 11.07 (br. s., 1 H) 9.01 (d, J = 2.02 Hz, 1 H) 9.00 (s, 1 H) 8.15 (d, J = 8.34 Hz, 1 H) 7.78-7.82 (m, 1 H) 7.28-7.36 (m, 3 H) 7.23-7.26 (m, 2 H) 7.21 (d, J = 8.59 Hz, 1 H) 4.27 (s, 2 H) 2.59 (s, 3 H) | I |
| 46 | N-(4-methylphenyl)-N-methyl | 8-hydroxy-N-(4-methylphenyl)-N-methylquinoline-5-sulfonamide | MS (ES+) m/z 329.0 [M + H]⁺<br>¹H NMR (400 MHz, DMSO-d6) δ ppm 11.06 (br. s., 1 H) 8.89 (dd, J = 4.04, 1.52 Hz, 1 H) 8.34 (dd, J = 8.84, 1.52 Hz, 1 H) 7.98 (d, J = 8.34 Hz, 1 H) 7.47 (dd, J = 8.84, 4.29 Hz, 1 H) 7.17 (d, J = 8.34 Hz, 1 H) 7.06 (d, J = 7.83 Hz, 2 H) 6.92-6.97 (m, 2 H) 3.09 (s, 3 H) 2.26 (s, 3 H) | I |
| 47 | isoindolin-2-yl | 5-isoindolin-2-ylsulfonylquinolin-8-ol | MS (ES+) m/z 327.0 [M + H]⁺<br>¹H NMR (400 MHz, DMSO-d6) δ ppm 11.09 (br. s., 1 H) 9.09 (dd, J = 8.59, 1.52 Hz, 1 H) 8.98 (dd, J = 4.04, 1.52 Hz, 1 H) 8.16 (d, J = 8.34 Hz, 1 H) 7.79 (dd, J = 8.84, 4.04 Hz, 1 H) 7.24 (br. s, 4 H) 7.20 (d, J = 8.34 Hz, 1 H) 4.58 (s, 4 H) | I |
| 48 | N-methyl-N-phenethyl | 8-hydroxy-N-methyl-N-phenethyl-quinoline-5-sulfonamide | MS (ES+) m/z 343.0 [M + H]⁺<br>¹H NMR (400 MHz, DMSO-d6) δ ppm 8.95 (dd, J = 4.29, 1.52 Hz, 2 H) 8.78 (dd, J = 8.84, 1.52 Hz, 2 H) 8.08 (d, J = 8.34 Hz, 2 H) 7.69 (dd, J = 8.84, 4.04 Hz, 2 H) 7.07-7.22 (m, 11 H) 3.29-3.36 (m, 4 H) 2.71-2.78 (m, 9 H) | I |

-continued

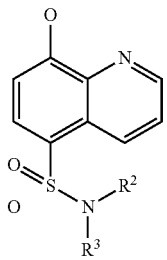

| Ex. | —NR²R³ | Name | Data | Prep Info |
|---|---|---|---|---|
| 49 | (4-fluorobenzyl)(methyl)amino | N-[(4-fluorophenyl)methyl]-8-hydroxy-N-methyl-quinoline-5-sulfonamide | MS (ES+) m/z 347.0 [M + H]⁺ ¹H NMR (400 MHz, DMSO-d6) δ ppm 8.97-9.03 (m, 2 H) 8.14 (d, J = 8.34 Hz, 1 H) 7.76-7.83 (m, 1 H) 7.26-7.33 (m, 2 H) 7.12-7.24 (m, 3 H), 4.26 (s, 2 H) 2.59 (s, 3 H) | I |
| 50 | ((1R)-1-phenylethyl)(methyl)amino | 8-hydroxy-N-methyl-N-[(1R)-1-phenylethyl]quinoline-5-sulfonamide | MS (ES+) m/z 343.0 [M + H]⁺ ¹H NMR (400 MHz, DMSO-d6) δ ppm 8.97-9.04 (m, 1 H) 8.89-8.96 (m, 1 H) 8.18 (d, J = 8.34 Hz, 1 H) 7.78 (dd, J = 8.72, 4.17 Hz, 1 H) 7.17-7.32 (m, 6 H) 5.19 (q, J = 7.33 Hz, 1 H) 2.51 (s, 3H) 1.27 (d, J = 7.07 Hz, 3 H) | I |
| 51 | ((1S)-1-phenylethyl)(methyl)amino | 8-hydroxy-N-methyl-N-[(1S)-1-phenylethyl]quinoline-5-sulfonamide | MS (ES+) m/z 343.0 [M + H]⁺ ¹H NMR (400 MHz, DMSO-d6) δ ppm 8.99 (dd, J = 4.17, 1.14 Hz, 1 H) 8.92 (dd, J = 8.84, 1.01 Hz, 1 H) 8.18 (d, J = 8.34 Hz, 1 H) 7.78 (dd, J = 8.84, 4.29 Hz, 1 H) 7.17-7.32 (m, 6 H) 5.19 (q, J = 6.65 Hz, 1 H) 2.51 (s, 3 H) 1.27 (d, J = 7.07 Hz, 3 H) | I |
| 52 | (2-fluorobenzyl)(methyl)amino | N-[(2-fluorophenyl)methyl]-8-hydroxy-N-methyl-quinoline-5-sulfonamide | MS (ES+) m/z 347.0 [M + H]⁺ ¹H NMR (400 MHz, DMSO-d6) δ ppm 11.09 (br. s., 1 H) 8.95-9.01 (m, 2 H) 8.15 (d, J = 8.59 Hz, 1 H) 7.77 (dd, J = 8.72, 4.17 Hz, 1 H) 7.31-7.39 (m, 2 H) 7.14-7.23 (m, 3 H) 4.34 (s, 2 H) 2.63 (s, 3 H) | I |
| 53 | (3-chlorobenzyl)(methyl)amino | N-[(3-chlorophenyl)methyl]-8-hydroxy-N-methyl-quinoline-5-sulfonamide | MS (ES+) m/z 363.0 [M + H]⁺ ¹H NMR (400 MHz, DMSO-d6) δ ppm 11.13 (br. s., 1 H) 8.95-9.04 (m, 2 H) 8.15 (d, J = 8.34 Hz, 1 H) 7.79 (dd, J = 8.72, 4.17 Hz, 1 H) 7.18-7.41 (m, 5 H) 4.29 (s, 2 H) 2.63 (s, 3 H) | I |

-continued

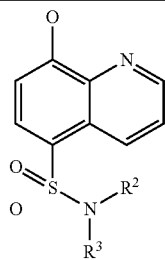

| Ex. | —NR²R³ | Name | Data | Prep Info |
|---|---|---|---|---|
| 54 | (N-methyl-N-(3-pyridylmethyl)) | 8-hydroxy-N-methyl-N-(3-pyridylmethyl)quinoline-5-sulfonamide | MS (ES+) m/z 330.0 [M + H]⁺ ¹H NMR (400 MHz, DMSO-d6) δ ppm 8.97-9.02 (m, 2 H) 8.49 (dd, J = 4.80, 1.77 Hz, 1 H) 8.43 (d, J = 1.77 Hz, 1 H) 8.16 (d, J = 8.59 Hz, 1 H) 7.79 (dd, J = 8.72, 4.17 Hz, 1 H) 7.67 (dt, J = 7.89, 1.99 Hz, 1 H) 7.37 (ddd, J = 7.83, 4.80, 0.76 Hz, 1 H) 7.22 (d, J = 8.34 Hz, 1 H) 4.33 (s, 2 H) 2.63 (s, 3 H) | I |
| 55 | (N-methyl-N-(2-naphthylmethyl)) | 8-hydroxy-N-methyl-N-(2-naphthylmethyl)quinoline-5-sulfonamide | MS (ES+) m/z 379.0 [M + H]⁺ ¹H NMR (400 MHz, DMSO-d6) δ ppm 9.15 (dd, J = 8.72, 1.39 Hz, 1 H) 9.01 (dd, J = 4.04, 1.52 Hz, 1 H) 8.23 (d, J = 8.34 Hz, 1 H) 8.17 (d, J = 8.34 Hz, 1 H) 7.95 (d, J = 7.33 Hz, 1 H) 7.90 (t, J = 4.80, 1 H) 7.78 (dd, J = 8.97, 4.17 Hz, 1 H) 7.42-7.57 (m, 4 H) 7.26 (d, J = 8.34 Hz, 1 H) 4.65 (s, 2 H) 2.50 (s, 3 H) | I |
| 56 | (N-benzyl-N-ethyl) | N-benzyl-N-ethyl-8-hydroxy-quinoline-5-sulfonamide | MS (ES+) m/z 379.0 [M + H]⁺ ¹H NMR (400 MHz, DMSO-d6) δ ppm 11.05 (br. s., 1 H) 9.00 (dd, J = 4.04, 1.52 Hz, 1 H) 8.91 (dd, J = 8.84, 1.52 Hz, 1 H) 8.15 (d, J = 8.34 Hz, 1 H) 7.79 (dd, J = 8.72, 4.17 Hz, 1 H) 7.16-7.36 (m, 6 H) 4.42 (s, 2 H) 3.17 (q, J = 7.07 Hz, 2 H) 0.82 (t, J = 7.07 Hz, 3 H) | I |
| 57 | (N-benzyl-N-(2-dimethylaminoethyl)) | N-benzyl-N-(2-dimethylaminoethyl)-8-hydroxy-quinoline-5-sulfonamide | MS (ES+) m/z 386.0 [M + H]⁺ ¹H NMR (400 MHz, DMSO-d6) δ ppm 9.00 (dd, J = 4.04, 1.52 Hz, 2 H) 8.92 (dd, J = 8.72, 1.64 Hz, 1 H) 8.18 (d, J = 8.34 Hz, 1 H) 7.79 (dd, J = 8.72, 4.17 Hz, 1 H) 7.19-7.32 (m, 5 H) 7.17 (d, J = 8.34 Hz, 1 H) 4.47 (s, 2 H) 3.17 (t, J = 6.95 Hz, 2 H) 2.06 (t, J = 7.07 Hz, 2 H) 1.88 (s, 6 H) | I |
| 58 | (2-phenylpyrrolidin-1-yl) | 5-(2-phenylpyrrolidin-1-yl)sulfonylquinolin-8-ol | MS (ES+) m/z 355.0 [M + H]⁺ ¹H NMR (400 MHz, DMSO-d6) δ ppm 8.93 (dd, J = 4.17, 1.39 Hz, 1 H) 8.86 (dd, J = 8.84, 1.26 Hz, 1 H) 8.02 (d, J = 8.59 Hz, 1 H) 7.68 (dd, J = 8.84, 4.04 Hz, 1 H) 7.11 (s, 5 H) 7.08 (d, J = 8.34 Hz, 1 H) 4.80 (dd, J = 8.21, 4.67 Hz, 1 H) 3.46-3.55 (m, 2 H) 2.06-2.17 (m, 1 H) 1.77-1.89 (m, 1 H) 1.61-1.74 (m, 2 H) | J |
| 59 | (pyrrolidin-1-yl) | 5-pyrrolidin-1-ylsulfonylquinolin-8-ol | MS (ES+) m/z 279.0 [M + H]⁺ ¹H NMR (400 MHz, DMSO-d6) δ ppm 11.02 (br. s., 1 H) 9.04 (dd, J = 8.84, 1.52 Hz, 1 H) 8.98 (dd, J = 4.04, 1.52 Hz, 1 H) 8.09 (d, J = 8.34 Hz, 1 H) 7.77 (dd, J = 8.72, 4.17 Hz, 1 H) 7.20 (d, J = 8.34 Hz, 1 H) 3.13-3.20 (m, 4 H) 1.70 (dt, J = 6.51, 3.44 Hz, 4 H) | J |

-continued

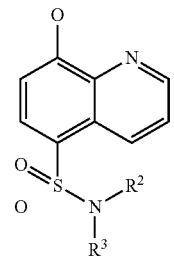

| Ex. | —NR²R³ | Name | Data | Prep Info |
|---|---|---|---|---|
| 60 | 4-methylpiperazin-1-yl | 5-(4-methylpiperazin-1-yl)sulfonylquinolin-8-ol | MS (ES+) m/z 308.0 [M + H]⁺ ¹H NMR (400 MHz. DMSO-d6) δ ppm 8.95-9.00 (m, 2 H) 8.08 (d, J = 8.34 Hz, 1 H) 7.75-7.79 (m, 1 H) 7.21 (d, J = 8.34 Hz, 1 H) 2.99 (br. s., 4 H) 2.28 (t, J = 4.67 Hz, 4 H) 2.10 (s, 3 H) | J |
| 61 | 2-phenyl-1-piperidyl | 5-[(2-phenyl-1-piperidyl)sulfonyl]quinolin-8-ol | MS (ES+) m/z 369.0 [M + H]⁺ ¹H NMR (400 MHz, DMSO-d6) δ ppm 9.01 (dd, J = 4.29, 1.52 Hz, 1 H) 8.94 (dd, J = 8.84, 1.52 Hz, 1 H) 8.19 (d, J = 8.34 Hz, 1 H) 7.80 (dd, J = 8.84, 4.04 Hz, 1 H) 7.27-7.34 (m, 4 H) 7.19-7.26 (m, 1 H) 7.16 (d, J = 8.34 Hz, 1 H) 5.25 (d, J = 3.54 Hz, 1 H) 3.69 (d, J = 12.88 Hz, 1 H) 2.92-3.01 (m, 1 H) 2.21 (d, J = 11.37 Hz, 1 H) 1.50 (ddd, J = 18.13, 9.54, 4.93 Hz, 1 H) 1.30-1.42 (m, 2 H) 1.09-1.19 (m, 1 H) 0.82-1.00 (m, 1 H) | J |
| 62 | 3-(4-fluorophenyl)pyrrolidin-1-yl | 5-(3-(4-fluorophenyl)pyrrolidin-1-yl)sulfonylquinolin-8-ol | MS (ES+) m/z 373.0 [M + H]⁺ ¹H NMR (400 MHz, DMSO-d6) δ ppm 9.05 (dd, J = 8.72, 1.64 Hz, 1 H) 8.99 (dd, J = 4.17, 1.64 Hz, 1 H) 8.13 (d, J = 8.34 Hz, 1 H) 7.77 (dd, J = 8.84, 4.29 Hz, 1,H) 7.16-7.23 (m, 3 H) 7 02-7 09 (m, 2 H) 3.68 (dd, J = 9.60, 7.58 Hz, 1 H) 3.45 (td, J = 8.97, 3.28 Hz, 1 H) 3.23-3.31 (m, 2 H) 3.04-3.11 (m, 1 H) 2.14-2.24 (m, 1 H) 1.79-1.91 (m, 1 H) | J |
| 63 | piperidin-1-yl | 5-(piperidin-1-yl)sulfonylquinolin-8-ol | MS (ES+) m/z 293.0 [M + H]⁺ ¹H NMR (400 MHz, DMSO-d6) δ ppm 8.96-9.02 (m, 2 H) 8.07 (d, J = 8.34 Hz, 1 H) 7.77 (dd, J = 8.84, 4.29 Hz, 1 H) 7.21 (d, J = 8.34 Hz, 1 H) 2.96-3.01 (m, 4H) 1.47 (d, J = 4.80 Hz, 4 H) 1.35 (d, J = 4.55 Hz, 2 H) | J |
| 64 | morpholin-4-yl | 5-(4-morpholin-1-yl)sulfonylquinolin-8-ol | MS (ES+) m/z 295.0 [M + H]⁺ ¹H NMR (400 MHz, DMSO-d6) δ ppm 8.98-9.04 (m, 2 H) 8.10 (d, J = 8.34 Hz, 1 H) 7.79 (dd, J = 8.59, 4.29 Hz, 1 H) 7.23 (d, J = 8.34 Hz, 1 H) 3.54-3.60 (m, 4 H) 2.94-2.99 (m, 4 H) | J |

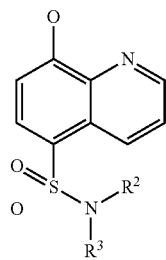

| Ex. | —NR²R³ | Name | Data | Prep Info |
|---|---|---|---|---|
| 65 | *N-methyl-N-(4-trifluoromethylbenzyl)* | N-[(4-(trifluoromethyl)phenyl)methyl]-8-hydroxy-N-methyl-quinoline-5-sulfonamide | MS (ES+) m/z 397.0 [M + H]⁺ ¹H NMR (400 MHz, DMSO-d6) δ ppm 11.10 (br. s., 1 H) 8.98-9.02 (m, 2 H) 8.16 (d, J = 8.34 Hz, 1 H) 7.77-7.82 (m, 1 H) 7.72 (d, J = 8.34 Hz, 2 H) 7.50 (d, J = 8.08 Hz, 2 H) 7.22 (d, J = 8.59 Hz, 1 H) 4.40 (s, 2 H) 2.64 (s, 3H) | J |
| 66 | *N-ethyl-N-(4-pyridylmethyl)* | N-ethyl-8-hydroxy-N-(4-pyridylmethyl)quinoline-5-sulfonamide | MS (ES+) m/z 344.0 [M + H]⁺ ¹H NMR (400 MHz, DMSO-d6) δ ppm 9.00 (dd, J = 4.04, 1.52 Hz, 1 H) 8.88-8.92 (m, 1 H) 8.46-8.48 (m, 2 H) 8.15 (d, J = 8.34 Hz, 1 H) 7.79 (dd, J = 8.72, 4.17 Hz, 1 H) 7.22-7.25 (m, 2 H) 7.18 (d, J = 8.59 Hz, 1 H) 4.49 (s, 2 H) 3.22 (q, J = 7.24 Hz, 2 H) 0.84 (t, J = 7.20 Hz, 3 H) | J |
| 67 | *5,6,7,8-tetrahydro-1,7-naphthyridin-7-yl* | 5-(6,8-dihydro-5H-1,7-naphthyridin-7-ylsulfonyl)quinolin-8-ol | MS (ES+) m/z 342.0 [M + H]⁺ ¹H NMR (400 MHz, DMSO-d6) δ ppm 8.94-9.01 (m, 2 H) 8.32 (dd, J = 4.80, 1.52 Hz, 1 H) 8.20 (d, J = 8.34 Hz, 1 H) 7.76 (dd, J = 8.72, 4.17 Hz, 1 H) 7.51 (d, J = 6.32 Hz, 1 H) 7.22 (d, J = 8.34 Hz, 1 H) 7.18 (dd, J = 7.71, 4.67 Hz, 1 H) 4.29 (s, 2 H) 3.48 (t, J = 5.81 Hz, 2 H) 2.80 (t, J = 5.81 Hz, 2 H) | J |
| 68 | *N,N-diethyl* | N,N-diethyl-8-hydroxy-quinoline-5-sulfonamide | MS (ES+) m/z 281.0 [M + H]⁺ ¹H NMR (400 MHz, DMSO-d6) δ ppm 8.98 (dd, J = 4.04, 1.52 Hz, 1 H) 8.86 (dd, J = 8.84, 1.52 Hz, 1 H) 8.08 (d, J = 8.34 Hz, 1 H) 7.78 (dd, J = 8.84, 4.04 Hz, 1 H) 7.17 (d, J = 8.34 Hz, 1 H) 3.25 (q, J = 7.07 Hz, 6 H) 0.98 (t, J = 7.07 Hz, 8 H) | J |
| 69 | *4-(5-chloro-2-pyridyl)piperazin-1-yl* | 5-[4-(5-chloro-2-pyridyl)piperazin-1-yl]sulfonylquinolin-8-ol | MS (ES+) m/z 405.0 [M + H]⁺ ¹H NMR (400 MHz, DMSO-d6) δ ppm 11.13 (br. s., 1 H) 9.02 (dd, J = 8.72, 1.64 Hz, 1 H) 8.97-8.99 (m, 1 H) 8.11 (d, J = 8.59 Hz, 1 H) 8.06 (d, J = 2.53 Hz, 1 H) 7.78 (dd, J = 8.84, 4.04 Hz, 1 H) 7.57 (dd, J = 9.10, 2.78 Hz, 1 H) 7.22 (d, J = 8.59 Hz, 1 H) 6.82 (d, J = 9.09 Hz, 1 H) 3.53 (d, J = 4.29 Hz, 4 H) 3.08 (d, J = 4.55 Hz, 4 H) | K |

-continued

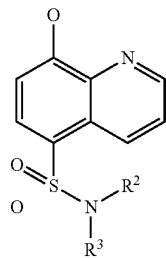

| Ex. | —NR²R³ | Name | Data | Prep Info |
|---|---|---|---|---|
| 70 | (3R,4R)-3,4-difluoropyrrolidin-1-yl | 5-[(3R,4R)-3,4-difluoropyrrolidin-1-yl]sulfonylquinolin-8-ol | MS (ES+) m/z 315.0 [M + H]⁺ ¹H NMR (400 MHz, DMSO-d6) δ ppm 8.98-9.05 (m, 2 H) 8.14 (d, J = 8.34 Hz, 1 H) 7.80 (dd, J = 8.84, 4.29 Hz, 1 H) 7.21 (d, J = 8.34 Hz, 1 H) 5.19-5.38 (m, 2 H) 3.44-3.65 (m, 4 H) | K |
| 71 | 2-(o-tolyl)pyrrolidin-1-yl | 5-[2-(o-tolyl)pyrrolidin-1-yl]sulfonylquinolin-8-ol | MS (ES+) m/z 369.2 [M + H]⁺ ¹H NMR (400 MHz, DMSO-d6) δ ppm 8.92-9.00 (m, 2 H) 8.06 (d, J = 8.34 Hz, 1 H) 7.74 (dd, J = 8.08, 4.04 Hz, 1 H) 7.11 (d, J = 8.34 Hz, 1 H) 6.94-7.06 (m, 3 H) 6.84 (d, J = 6.57 Hz, 1 H) 4.95 (d, J = 4.55 Hz, 1 H) 3.50-3.61 (m, 2 H) 2.21 (s, 3 H) 2.15 (d, J = 6.06 Hz, 1 H) 1.66-1.87 (m, 2 H) 1.55 (d, J = 6.82 Hz, 1 H) | K |
| 72 | 2-(3-pyridyl)pyrrolidin-1-yl | 5-[2-(3-pyridyl)pyrrolidin-1-yl]sulfonylquinolin-8-ol | MS (ES+) m/z 356.0 [M + H]⁺ ¹H NMR (400 MHz, DMSO-d6) δ ppm 8.98-9.05 (m, 2 H) 8.79 (br. s., 1 H) 8.72 (br. s., 1 H) 8.40 (d, J = 8.08 Hz, 1 H) 8.14 (dd, J = 8.21, 3.66 Hz, 1 H) 7.81-7.89 (m, 2 H) 7.25 (dd, J = 8.34, 3.54 Hz, 1 H) 4.95-5.02 (m, 1 H) 3.68 (d, J = 6.32 Hz, 1 H) 3.45-3.54 (m, 1 H) 2.21 (br. s., 1 H) 1.90 (br. s, 1 H) 1.81 (br. s., 1 H) 1.70 (br. s., 1 H) | K |
| 73 | 4-phenyl-1-piperidyl | 5-[(4-phenyl-1-piperidyl)sulfonyl]quinolin-8-ol | MS (ES+) m/z 369.0 [M + H]⁺ ¹H NMR (400 MHz, DMSO-d6) δ ppm 9.17 (d, J = 8.84 Hz, 1 H) 9.04 (br. s., 1 H) 8.16 (d, J = 8.34 Hz, 1 H) 7.88 (br. s., 1 H) 7.22-7.36 (m, 3 H) 7.10-7.21 (m, 3 H) 3.81 (d, J = 10.11 Hz, 2 H) 2.45 (br. s., 3 H) 1.78 (d, J = 11.12 Hz, 2 H) 1.58 (d, J = 9.85 Hz, 2 H) | K |
| 74 | 2-(4-fluorophenyl)pyrrolidin-1-yl | 5-[2-(4-fluorophenyl)pyrrolidin-1-yl]sulfonylquinolin-8-ol | MS (ES+) m/z 373.0 [M + H]⁺ ¹HNMR (400 MHz, DMSO-d6) δ ppm 10.97 (br. s, 1 H) 8.94 (dd, J = 4.30, 1.52 Hz, 1 H) 8.84 (dd, J = 8.84, 1.52 Hz, 1 H) 8.01 (d, J = 8.34 Hz, 1 H) 7.69 (dd, J = 8.72, 4.17 Hz, 1 H) 7.05-7.17 (m, 3 H) 6.85-6.96 (m, 2 H) 4.78 (dd, J = 7.71, 4.67 Hz, 1 H) 3.52 (t, J = 5.81 Hz, 2 H) 2.05-2.17 (m, 1H) 1.78-1.89 (m, 1 H) 1.59-1.76 (m, 2 H) | L |
| 75 | 2-benzylpyrrolidin-1-yl | 5-(2-benzylpyrrolidin-1-yl)sulfonylquinolin-8-ol | MS (ES+) m/z 369.0 [M + H]⁺ ¹H NMR (400 MHz, DMSO-d6) δ ppm 11.05 (br. s., 1 H) 9.09 (dd, J = 8.84, 1.52 Hz, 1 H) 8.98 (dd, J = 4.29, 1.52 Hz, 1 H) 8.18 (d, J = 8.34 Hz, 1 H) 7.79 (dd, J = 8.84, 4.04 Hz, 1 H) 7.10-7.31 (m, 6 H) 3.86 (t, J = 8.46 Hz, 1 H) 3.15-3.30 (m, 3 H) 2.84-2.95 (m, 1 H) 2.62 (dd, J = 13.14, 9.60 | L |

-continued

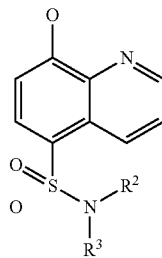

| Ex. | —NR²R³ | Name | Data | Prep Info |
|---|---|---|---|---|
| | | | Hz, 1 H) 1.63-1.76 (m, 1 H) 1.36-1.60 (m, 3H) | |
| 76 | | 5-(2-cyclohexylpyrrolidin-1-yl)sulfonylquinolin-8-ol | MS (ES+) m/z 361.2 [M + H]⁺ ¹H NMR (400 MHz, DMSO-d6) δ ppm 11.04 (br. s., 1 H) 9.04 (dd, J = 8.84, 1.52 Hz, 1 H) 8.98 (dd, J = 4.04, 1.52 Hz, 1 H) 8.13 (d, J = 8.34 Hz, 1 H) 7.78 (dd, J = 8.84, 4.04 Hz, 1 H) 7.20 (d, J = 8.34 Hz, 1 H) 3.58-3.65 (m, 1 H) 3.05-3.13 (m, 2 H) 1.35-1.68 (m, 10 H) 0.98-1.14 (m, 2 H) 0.83 (d, J = 7.83 Hz, 3 H) | L |
| 77 | | 5-[2-(4-methoxyphenyl)pyrrolidin-1-yl]sulfonylquinolin-8-ol | MS (ES+) m/z 385.0 [M + H]⁺ ¹H NMR (400 MHz, DMSO-d6) δ ppm 10.92 (br. s., 1 H) 8.93 (dd, J = 4.29, 1.52 Hz, 1 H) 8.83 (dd, J = 8.84, 1.52 Hz, 1 H) 7.98 (d, J = 8.34 Hz, 1 H) 7.67 (dd, J = 8.72, 4.17 Hz, 1 H) 7.06 (d, J = 8.34 Hz, 1 H) 6.98 (d, J = 8.84 Hz, 2 H) 6.63 (d, J = 8.59 Hz, 2 H) 4.72 (dd, J = 7.71, 4.93 Hz, 1 H) 3.67 (s, 3 H) 3.49 (t, J = 6.44 Hz, 2 H) 2.02-2.14 (m, 1 H) 1.77-1.89 (m, 1 H) 1.67 (td, J = 11.75, 5.56 Hz, 2 H) | L |
| 78 | | 5-(2-isopropylpyrrolidin-1-yl)sulfonylquinolin-8-ol | MS (ES+) m/z 321.0 [M + H]⁺ ¹H NMR (400 MHz, DMSO-d6) δ ppm 11.05 (br. s., 1 H) 9.06 (dd, J = 8.72, 1.39 Hz, 1 H) 8.98 (dd, J = 4.04, 1.52 Hz, 1 H) 8.13 (d, J = 8.59 Hz, 1 H) 7.79 (dd, J = 8.84, 4.04 Hz, 1 H) 7.20 (d, J = 8.34 Hz, 1 H) 3.60 (dt, J = 8.21, 4.86 Hz, 1 H) 3.30-3.40 (m, 1 H) 3.08-3.17 (m, 1 H) 1.87-2.00 (m, 1 H) 1.55-1.70 (m, 2 H) 1.43-1.55 (m, 1 H) 1.30-1.41 (m, 1 H) 0.78 (d, J = 6.82 Hz, 3 H) 0.73 (d, J = 6.82 Hz, 3 H) | L |
| 79 | | 5-[2-(4-pyridyl)pyrrolidin-1-yl]sulfonylquinolin-8-ol | MS (ES+) m/z 356.0 [M + H]⁺ ¹H NMR (400 MHz, DMSO-d6) δ ppm 11.06 (br. s, 1 H) 8.96 (dd, J = 4.04, 1.52 Hz, 1 H) 8.90 (dd, J = 8.84, 1.52 Hz, 1 H) 8.29-8.34 (m, 2 H) 8.06 (d, J = 8.34 Hz, 1 H) 7.73 (dd, J = 8.72, 4.17 Hz, 1 H) 7.13-7.16 (m, 2 H) 7.10 (d, J = 8.34 Hz, 1 H) 4.80 (dd, J = 8.46, 4.17 Hz, 1 H) 3.52-3.59 (m, 1 H) 3.46 (dt, J = 9.92, 6.79 Hz, 1 H) 2.08-2.19 (m, 1 H) 1.76-1.86 (m, 1 H) 1.61-1.73 (m, 2H) | L |
| 80 | | 5-[2-(2-pyridyl)pyrrolidin-1-yl]sulfonylquinolin-8-ol | MS (ES+) m/z 356.0 [M + H]⁺ ¹H NMR (400 MHz, DMSO-d6) δ ppm 10.96 (br. s., 1 H) 8.94 (dd, J = 4.04, 1.52 Hz, 1 H) 8.89 (dd, J = 8.84, 1.52 Hz, 1 H) 8.32-8.35 (m, 1 H) 8.05 (d, J = 8.34 Hz, 1 H) 7.69 (dd, J = 8.72, 4.17 Hz, 1 H) 7.56 (td, J = 7.71, 1.77 Hz, 1 H) 7.21 (d, J = 7.83 Hz, 1 H) 7.09-7.15 (m, 2 H) 4.83 (dd, J = 8.08, | L |

-continued

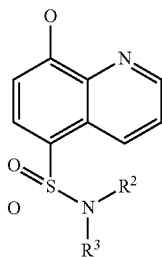

| Ex. | —NR²R³ | Name | Data | Prep Info |
|---|---|---|---|---|
| | | | 3.79 Hz, 1 H) 3.43-3.57 (m, 2 H) 2.07 (dt, J = 11.49, 8.02 Hz, 1 H) 1.80-1.94 (m, 2 H) 1.65-1.76 (m, 1 H) | |
| 81 | | 5-[2-[2-(trifluoromethyl)phenyl]pyrrolidin-1-yl]sulfonylquinolin-8-ol | MS (ES+) m/z 423.2 [M + H]⁺ ¹H NMR (400 MHz. DMSO-d6) δ ppm 11.00 (br. s, 1 H) 8.95 (dd, J = 4.04, 1.52 Hz, 1 H) 8.91 (dd, J = 8.84, 1.52 Hz, 1 H) 7.97 (d, J = 8.34 Hz, 1 H) 7.72 (dd, J = 8.84, 4.04 Hz, 1 H) 7.54 (d, J = 6.57 Hz, 1 H) 7.19-7.33 (m, 3 H) 7.03 (d, J = 8.34 Hz, 1 H) 5.05 (dd, J = 8.46, 4.42 Hz, 1 H) 3.67-3.74 (m, 1 H) 3.54-3.62 (m, 1 H) 2.16-2.27 (m, 1 H) 1.86-1.95 (m, 1 H) 1.72-1.81 (m, 1 H) 1.58 (dd, J = 11.75, 5.94 Hz, 1 H) | L |
| 82 | | 5-(2-isobutylpyrrolidin-1-yl)sulfonylquinolin-8-ol | MS (ES+) m/z 335.2 [M + H]⁺ ¹H NMR (400 MHz, DMSO-d6) δ ppm 11.04 (br. s, 1 H) 9.07 (dd, J = 8.84, 1.52 Hz, 1 H) 8.98 (dd, J = 4.04, 1.52 Hz, 1 H) 8.11 (d, J = 8.34 Hz, 1 H) 7.78 (dd, J = 8.84, 4.29 Hz, 1 H) 7.21 (d, J = 8.34 Hz, 1 H) 3.64-3.73 (m, 1 H) 3.24 (td, J = 6.57, 2.78 Hz, 2 H) 1.67-1.79 (m, 1 H) 1.33-1.63 (m, 5 H) 1.19-1.28 (m, 1 H) 0.79 (dd, J = 8.97, 6.44 Hz, 6 H) | L |
| 83 | | 5-[(4-hydroxy-4-phenyl-1-piperidyl)sulfonyl]quinolin-8-ol | MS (ES+) m/z 385.2 [M + H]⁺ ¹H NMR (400 MHz, DMSO-d6) δ ppm 11.09 (br. s., 1 H) 9.11 (dd, J = 8.84, 1.52 Hz, 1 H) 9.00 (dd, J = 4.17, 1.39 Hz, 1H) 8.13 (d, J = 8.34 Hz, 1 H) 7.79 (dd, J = 8.84, 4.04 Hz, 1 H) 7.34-7.40 (m, 2 H) 7.17-7.32 (m, 4 H) 4.94 (s, 1 H) 3.62 (d, J = 11.12 Hz, 2 H) 2.68-2.78 (m, 2 H) 1.90 (td, J = 12.82, 4.17 Hz, 2 H) 1.61 (d, J = 12.38 Hz, 2 H) | L |
| 84 | | 5-[(4-benzyl-1-piperidyl)sulfonyl]quinolin-8-ol | MS (ES-) m/z 383.2 [M + H]⁺ ¹H NMR (400 MHz, DMSO-d6) δ ppm 11.03 (br. s., 1 H) 8.94-8.99 (m, 2 H) 8.05 (d, J = 8.34 Hz, 1 H) 7.72-7.77 (m, 1 H) 7.11-7.26 (m, 4 H) 7.06-7.10 (m, 2 H) 3.65 (d, J = 11.87 Hz, 2 H) 2.42 (d, J = 6.82 Hz, 2 H) 2.29-2.38 (m, 2 H) 1.43-1.61 (m, 3 H) 1.03-1.17 (m, 2 H) | L |

-continued

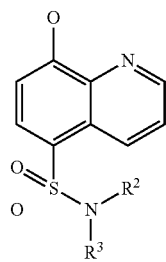

| Ex. | —NR²R³ | Name | Data | Prep Info |
|---|---|---|---|---|
| 85 | (piperidyl-phenylmethanone structure) | [1-[(8-hydroxy-5-quinolyl)sulfonyl]-4-piperidyl]-phenyl-methanone | MS (ES+) m/z 397.0 [M + H]⁺ ¹H NMR (400 MHz, DMSO-d6) δ ppm 11.07 (br. s, 1 H) 9.04 (dd, J = 8.84, 1.52 Hz, 1 H) 9.00 (dd, J = 4.17, 1.39 Hz, 1 H) 8.10 (d, J = 8.34 Hz, 1 H) 7.89-7.94 (m, 2 H) 7.79 (dd, J = 8.72, 4.17 Hz, 1 H) 7.57-7.64 (m, 1 H) 7.44-7.51 (m, 2 H) 7.23 (d, J = 8.34 Hz, 1 H) 3.72 (d, J = 12.13 Hz, 2 H) 3.41-3.51 (m, 1 H) 2.54-2.63 (m, 2 H) 1.81 (d, J = 11.12 Hz, 2 H) 1.42-1.56 (m, 2 H) | L |
| 86 | (4-phenyl-4-piperidyl ethanone structure) | 1-[1-[(8-hydroxy-5-quinolyl)sulfonyl]-4-phenyl-4-piperidyl]ethanone | MS (ES+) m/z 411.0 [M + H]⁺ ¹H NMR (400 MHz, DMSO-d6) δ ppm 11.09 (br. s, 1 H) 8.92-8.99 (m, 2 H) 8.07 (d, J = 8.34 Hz, 1 H) 7.76 (dd, J = 8.84, 4.29 Hz, 1 H) 7.31-7.38 (m, 2 H) 7.23-7.29 (m, 3 H) 7.19 (d, J = 8.34 Hz, 1 H) 3.33-3.40 (m, 2 H) 2.72-2.81 (m, 2H) 2.40 (d, J = 13.90 Hz, 2 H) 1.90-2.00 (m, 2 H) 1.78 (s, 3 H) | L |
| 87 | (triazaspiro[4.5]decan-4-one structure) | 8-[(8-hydroxy-5-quinolyl)sulfonyl]-1-phenyl-1,3,8-triazaspiro[4.5]decan-4-one | MS (ES+) m/z 439.0 [M + H]⁺ ¹H NMR (400 MHz, DMSO-d6) δ ppm 11.17 (br. s., 1 H) 8.99-9.07 (m, 2 H) 8.77 (s, 1 H) 8.16 (d, J = 8.59 Hz, 1 H) 7.83 (dd, J = 8.84, 4.29 Hz, 1 H) 7.22 (d, J = 8.34 Hz, 1 H) 7.11 (t, J = 8.08 Hz, 2 H) 6.69-6.75 (m, 1 H) 6.57 (d, J = 7.83 Hz, 2 H) 4.54 (s, 2 H) 3.68-3.77 (m, 2 H) 3.27-3.36 (m, 2 H) 2.35-2.47 (m, 2 H) 1.63 (d, J = 13.64 Hz, 2 H) | L |
| 88 | (piperazine-carboxylate structure) | methyl 4-[(8-hydroxy-5-quinolyl)sulfonyl]piperazine-1-carboxylate | MS (ES+) m/z 352.0 [M + H]⁺ ¹H NMR (400 MHz, DMSO-d6) δ ppm 11.13 (br. s., 1 H) 8.94-9.02 (m, 2 H) 8.08 (d, J = 8.34 Hz, 1 H) 7.77 (dd, J = 8.72, 4.17 Hz, 1 H) 7.21 (d, J = 8.34 Hz, 1 H) 3.52 (s, 3 H) 3.36-3.41 (m, 4 H) 2.96-3.05 (m, 4 H) | L |
| 89 | (4-(3-methoxypropyl)piperazin-1-yl structure) | 5-[4-(3-methoxypropyl)piperazin-1-yl]sulfonylquinolin-8-ol | MS (ES+) m/z 366.2 [M + H]⁺ ¹H NMR (400 MHz, DMSO-d6) δ ppm 11.11 (br. s, 1 H) 8.97-9.03 (m, 2 H) 8.08 (d, J = 8.34 Hz, 1 H) 7.74-7.80 (m, 1 H) 7.22 (d, J = 8.59 Hz, 1 H) 3.23 (t, J = 6.32 Hz, 2 H) 3.14 (s, 3 H) 2.97 (br. s., 4 H) 2.34 (br. s., 4 H) 2.25 (br. s., 2H) 1.49-1.59 (m, 2 H) | L |

-continued

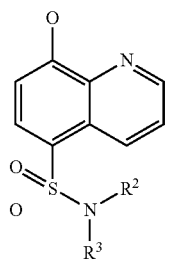

| Ex. | —NR²R³ | Name | Data | Prep Info |
|---|---|---|---|---|
| 90 | (piperazine with 2-cyanophenyl) | 2-[4-[(8-hydroxy-5-quinolyl)sulfonyl]piperazin-1-yl]benzonitrile | MS (ES+) m/z 395.0 [M + H]⁺ ¹H NMR (400 MHz, DMSO-d6) δ ppm 11.19 (br. s., 1 H) 9.04 (dd, J = 8.84, 1.52 Hz, 1 H) 8.99-9.02 (m, 1 H) 8.15 (d, J = 8.59 Hz, 1 H) 7.80 (dd, J = 8.84, 4.29 Hz, 1 H) 7.68 (dd, J = 7.83, 1.52 Hz, 1 H) 7.59 (td, J = 7.96, 1.52 Hz, 1 H) 7.25 (d, J = 8.34 Hz, 1 H) 7.09-7.17 (m, 2 H) 3.17 (d, J = 5.05 Hz, 8 H) | L |
| 91 | (3-azabicyclo[3.2.2]nonane) | 5-(3-azabicyclo[3.2.2]nonan-3-ylsulfonyl)quinolin-8-ol | MS (ES+) m/z 333.2 [M + H]⁺ ¹H NMR (400 MHz, DMSO-d6) δ ppm 11.02 (br. s, 1 H) 8.94-9.00 (m, 2 H) 8.06 (d, J = 8.34 Hz, 1 H) 7.78 (dd, J = 8.72, 4.17 Hz, 1 H) 7.18 (d, J = 8.34 Hz, 1 H) 3.27 (d, J = 4.04 Hz, 4 H) 2.01 (br. s., 2 H) 1.46-1.59 (m, 8 H) | L |
| 92 | (piperazine with 2-phenylphenyl) | 5-[4-(2-phenylphenyl)piperazin-1-yl]sulfonylquinolin-8-ol | MS (ES+) m/z 446.2 [M + H]⁺ ¹H NMR (400 MHz, DMSO-d6) δ ppm 11.14 (br. s., 1 H) 9.01 (dd, J = 4.04, 1.52 Hz, 1 H) 8.92 (dd, J = 8.84, 1.52 Hz, 1 H) 8.07 (d, J = 8.59 Hz, 1 H) 7.75 (dd, J = 8.72, 4.17 Hz, 1 H) 7.42-7.46 (m, 2 H) 7.18-7.29 (m, 5 H) 7.16 (dd, J = 7.45, 1.64 Hz, 1 H) 7.04-7.10 (m, 1 H) 7.01 (d, J = 8.08 Hz, 1 H) 2.89 (br. s., 4 H) 2.74 (d, J = 4.29 Hz, 4 H) | L |
| 93 | (piperazine with 2,5-dimethylphenyl) | 5-[4-(2,5-dimethylphenyl)piperazin-1-yl]sulfonylquinolin-8-ol | MS (ES+) m/z 398.2 [M + H]⁺ ¹H NMR (400 MHz, DMSO-d6) δ ppm 11.15 (br. s, 1 H) 8.99-9.06 (m, 2 H) 8.13 (d, J = 8.34 Hz, 1 H) 7.80 (dd, J = 8.84, 4.04 Hz, 1 H) 7.24 (d, J = 8.34 Hz, 1 H) 6.98 (d, J = 7.58 Hz, 1 H) 6.73-6.79 (m, 2 H) 3.14 (br. s., 4 H) 2.83 (t, J = 4.55 Hz, 4 H) 2.21 (s, 3 H) 2.04 (s, 3 H) | L |

-continued

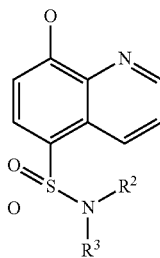

| Ex. | —NR²R³ | Name | Data | Prep Info |
|---|---|---|---|---|
| 94 | (piperazine linked to 4-(trifluoromethyl)phenyl) | 5-[4-[4-(trifluoromethyl)phenyl]piperazin-1-yl]sulfonylquinolin-8-ol | MS (ES+) m/z 438.0 [M + H]⁺ ¹H NMR (400 MHz, DMSO-d6) δ ppm 11.13 (br. s, 1 H) 9.03 (dd, J = 8.84, 1.52 Hz, 1 H) 8.99 (dd, J = 4.17, 1.39 Hz, 1 H) 8.13 (d, J = 8.34 Hz, 1 H) 7.79 (dd, J = 8.72, 4.17 Hz, 1 H) 7.47 (d, J = 9.09 Hz, 2 H) 7.23 (d, J = 8.34 Hz, 1 H) 7.00 (d, J = 8.84 Hz, 2 H) 3.29-3.32 (m, 4 H) 3.10-3.15 (m, 4 H) | L |
| 95 | (piperazine linked to bis(4-fluorophenyl)methyl) | 5-[4-[bis(4-fluorophenyl)methyl]piperazin-1-yl]sulfonylquinolin-8-ol | MS (ES+) m/z 496.2 [M + H]⁺ ¹H NMR (400 MHz, DMSO-d6) δ ppm 11.12 (br. s, 1 H) 8.98-9.02 (m, 2 H) 8.06 (d, J = 8.59 Hz, 1 H) 7.73-7.77 (m, 1 H) 7.34 (dd, J = 8.21, 5.68 Hz, 4 H) 7.23 (d, J = 8.34 Hz, 1 H) 7.02-7.10 (m, 4 H) 4.36 (s, 1 H) 3.00 (br. s., 4 H) 2.29 (br. s, 4 H) | L |
| 96 | (piperazine linked to 4-fluorophenyl) | 5-[4-(4-fluorophenyl)piperazin-1-yl]sulfonylquinolin-8-ol | MS (ES+) m/z 388.2 [M + H]⁺ ¹H NMR (400 MHz, DMSO-d6) δ ppm 11.12 (br.s., 1 H) 9.03 (dd, J = 8.84, 1.52 Hz, 1 H) 8.99 (dd, J = 4.04, 1.52 Hz, 1 H) 8.13 (d, J = 8.34 Hz, 1 H) 7.79 (dd, J = 8.84, 4.29 Hz, 1 H) 7.24 (d, J = 8.59 Hz, 1 H) 6.99-7.05 (m, 2 H) 6.87-6.92 (m, 2 H) 3.10 (dd, J = 16.67, 5.56 Hz, 8 H) | L |
| 97 | (piperazine linked to 2,3-dichlorophenyl) | 5-[4-(2,3-dichlorophenyl)piperazin-1-yl]sulfonylquinolin-8-ol | MS (ES+) m/z 438.0 [M+H]⁺ ¹H NMR (400 MHz, DMSO-d6) δ ppm 11.17 (br. s, 1 H) 9.05 (dd, J = 8.84, 1.52 Hz, 1 H) 9.01 (dd, J = 4.17, 1.39 Hz, 1 H) 8.14 (d, J = 8.59 Hz, 1 H) 7.80 (dd, J = 8.84, 4.29 Hz, 1 H) 7.27-7.33 (m, 2 H) 7.25 (d, J = 8.34 Hz, 1 H) 7.12 (dd, J = 6.95, 2.65 Hz, 1 H) 3.17 (br. s., 4 H) 3.01 (d, J = 4.29 Hz, 4 H) | L |

-continued

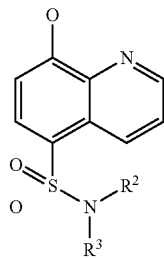

| Ex. | —NR²R³ | Name | Data | Prep Info |
|---|---|---|---|---|
| 98 | (1,2-benzothiazol-3-yl)piperazinyl | 5-[4-(1,2-benzothiazol-3-yl)piperazin-1-yl]sulfonylquinolin-8-ol | MS (ES+) m/z 427.2 [M + H]⁺ ¹H NMR (400 MHz, DMSO-d6) δ ppm 11.15 (br. s., 1 H) 9.06 (d, J = 8.84 Hz, 1 H) 9.01 (d, J = 4.04 Hz, 1 H) 8.14 (d, J = 8.34 Hz, 1 H) 8.03 (d, J = 8.08 Hz, 1 H) 7.99 (d, J = 8.34 Hz, 1 H) 7.80 (dd, J = 8.72, 4.17 Hz, 1 H) 7.53 (t, J = 7.33 Hz, 1 H) 7.35-7.41 (m, 1 H) 7.25 (d, J = 8.34 Hz, 1 H) 3.45 (br. s, 4 H) 3.25 (br. s, 4 H) | L |
| 99 | 3-[4-(trifluoromethoxy)phenoxy]azetidinyl | 5-[3-[4-(trifluoromethoxy)phenoxy]azetidin-1-yl]sulfonylquinolin-8-ol | MS (ES+) m/z 441.0 [M + H]⁺ ¹H NMR (400 MHz, DMSO-d6) δ ppm 11.23 (br. s, 1 H) 9.00 (dd, J = 4.04, 1.52 Hz, 1 H) 8.96 (dd, J = 8.84, 1.52 Hz, 1 H) 8.15 (d, J = 8.34 Hz, 1 H) 7.80 (dd, J = 8.72, 4.17 Hz, 1 H) 7.24 (t, J = 8.97 Hz, 3 H) 6.84-6.89 (m, 2 H) 4.91-4.99 (m, 1 H) 4.21 (dd, J = 9.35, 6.32 Hz, 2 H) 3.73 (dd, J = 9.47, 4.67 Hz, 2 H) | L |
| 100 | 4-(2,3-dimethylphenyl)piperazinyl | 5-[4-(2,3-dimethylphenyl)piperazin-1-yl]sulfonylquinolin-8-ol | MS (ES+) m/z 398.0 [M + H]⁺ ¹H NMR (400 MHz, DMSO-d6) δ ppm 11.13 (br. s, 1 H) 9.04 (dd, J = 8.84, 1.52 Hz, 1 H) 9.01 (dd, J = 4.04, 1.52 Hz, 1 H) 8.13 (d, J = 8.34 Hz, 1 H) 7.80 (dd, J = 8.72, 4.17 Hz, 1 H) 7.25 (d, J = 8.34 Hz, 1 H) 6.98-7.03 (m, 1 H) 6.85 (dd, J = 10.86, 7.83 Hz, 2 H) 3.16 (br. s., 4 H) 2.80 (br. s, 4 H) 2.15 (s, 3 H) 2.01 (s, 3H) | L |
| 101 | 4-[(4-fluorophenyl)methyl]piperazinyl | 5-[4-[(4-fluorophenyl)methyl]piperazin-1-yl]sulfonylquinolin-8-ol | MS (ES+) m/z 402.2 [M + H]⁺ ¹H NMR (400 MHz, DMSO-d6) δ ppm 11.10 (br. s, 1 H) 8.98 (dq, J = 6.44, 1.39 Hz, 2 H) 8.07 (d, J = 8.34 Hz, 1 H) 7.73-7.78 (m, 1 H) 7.19-7.26 (m, 3 H) 7.04-7.11 (m, 2 H) 3.40 (s, 2 H) 2.99 (br. s., 4 H) 2.35 (br. s., 4 H) | L |
| 102 | 3-phenylpiperidinyl | 5-[(3-phenyl-1-piperidyl)sulfonyl]quinolin-8-ol | MS (ES+) m/z 369.2 [M + H]⁺ ¹H NMR (400 MHz, DMSO-d6) δ ppm 11.06 (br. s, 1 H) 9.01 (dd, J = 8.72, 1.64 Hz, 1 H) 8.98 (dd, J = 4.04, 1.52 Hz, 1 H) 8.09 (d, J = 8.34 Hz, 1 H) 7.77 (dd, J = 8.84, 4.29 Hz, 1 H) 7.25-7.30 (m, 2 H) 7.18-7.23 (m, 4 H) 3.73 (d, J = 10.86, 1 H) 3.66 (d, J = 11.37 Hz, 1 H) 2.68 (d, J = 10.36, 1 H) 2.46-2.58 (m, 2 H) 1.75 (d, J = 9.35 Hz, 2 H) 1.47-1.55 (m, 2 H) | L |

-continued

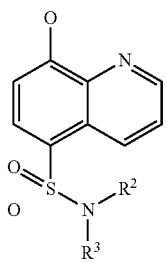

| Ex. | —NR²R³ | Name | Data | Prep Info |
|---|---|---|---|---|
| 103 | *tert-butyl piperazine-1-carboxylate structure* | tert-butyl 4-[(8-hydroxy-5-quinolyl)sulfonyl]piperazine-1-carboxylate | MS (ES+) m/z 394.2 [M + H]⁺ ¹H NMR (400 MHz, DMSO-d6) δ ppm 11.09 (br. s, 1 H) 9.00 (s, 1 H) 8.97-8.99 (m, 1 H) 8.08 (d, J = 8.34 Hz, 1 H) 7.75-7.79 (m, 1 H) 7.21 (d, J = 8.34 Hz, 1 H) 3.34 (d, J = 4.29 Hz, 4 H) 2.94-2.99 (m, 4 H) 1.32 (s, 9 H) | L |
| 104 | *piperazine structure* | 5-piperazin-1-ylsulfonylquinolin-8-ol | MS (ES+) m/z 294.0 [M + H]⁺ ¹H NMR (400 MHz, DMSO-d6) δ ppm 9.23 (br. s, 2 H) 9.02-9.09 (m, 2 H) 8.16 (d, J = 8.34 Hz, 1 H) 7.86 (dd, J = 8.72, 4.42 Hz, 1 H) 7.32 (d, J = 8.34 Hz, 1 H) 3.24 (d, J = 5.05 Hz, 4 H) 3.10 (br. s., 4 H) | L |
| 105 | *3-methyl-piperazine-1-carboxylate structure* | tert-butyl 4-[(8-hydroxy-5-quinolyl)sulfonyl]-3-methyl-piperazine-1-carboxylate | MS (ES+) m/z 408.2 [M + H]⁺ ¹H NMR (400 MHz, DMSO-d6) δ ppm 11.08 (br. s., 1 H) 8.99 (dd, J = 4.04, 1.52 Hz, 1 H) 8.78 (dd, J = 8.84, 1.26 Hz, 1 H) 8.14 (d, J = 8.34 Hz, 1 H) 7.79 (dd, J = 8.84, 4.04, 1 H) 7.18 (d, J = 8.34 Hz, 1 H) 4.07 (br. s., 1 H) 3.85 (br. s., 1 H) 3.70 (d, J = 13.90 Hz, 1 H) 3.40-3.46 (m, 2 H) 3.00-3.11 (m, 1 H) 2.70-2.91 (m, 1 H) 1.35 (s, 9 H) 0.98 (d, J = 5.56 Hz, 3 H) | L |
| 106 | *2-methylpiperazine structure* | 5-(2-methylpiperazin-1-yl)sulfonylquinolin-8-ol | MS (ES+) m/z 308.0 [M + H]⁺ ¹H NMR (400 MHz, DMSO-d6) δ ppm 9.60 (br. s., 1 H) 9.01-9.14 (m, 2 H) 8.82 (d, J = 8.84 Hz, 1 H) 8.19 (d, J = 8.34 Hz, 1 H) 7.85 (dd, J = 8.59, 4.29 Hz, 1 H) 7.25 (d, J = 8.34 Hz, 1 H) 4.27 (br. s, 1 H) 3.55-3.63 (m, 1 H) 3.29 (t, J = 12.00 Hz, 1 H) 3.08-3.21 (m, 2 H) 2.90 (d, J = 12.38 Hz, 1 H) 2.60 (d, J = 12.63 Hz, 1 H) 1.24 (d, J = 7.07 Hz, 3 H) | L |

Example 107

7-iodo-5-(p-tolylsulfonyl)quinolin-8-ol—Method N

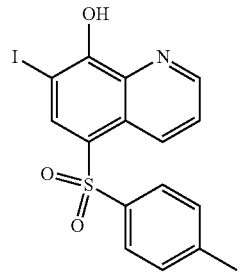 [SMILES: Cc1ccc(S(=O)(=O)c2cc(I)c(O)c3ncccc23)cc1]

Step 1: 5-iodo-8-((4-methoxybenzyl)oxy)quinolone

The compound was prepared as previously described in WO198901465 and *Synthesis* 2006, 8, 1325-1332.

Step 2: 8-((4-methoxybenzyl)oxy)-5-tosylquinoline

A mixture of 5-iodo-8-((4-methoxybenzyl)oxy)quinoline (740 mg, 1.892 mmol), copper(I) iodide (36.0 mg, 0.189 mmol), sodium (S)-pyrrolidine-2-carboxylate (51.9 mg, 0.378 mmol) and sodium 4-methylbenzenesulfinate (404 mg, 2.27 mmol) in DMSO (10 ml) was heated to 90° C. overnight. The DMSO mixture was concentrated further under a nitrogen stream with heating at 50° C. to approximately 15 ml of volume. All materials were poured onto a silica pad atop a Thomson (90 g) column. The material was purified by automated normal-phase chromatography using 0-80% ethyl acetate/hexanes as an eluent. Two peaks were collected one as the title compound (200.9 mg, 25% yield) and recovered starting material (5-iodo-8-((4-methoxybenzyl)oxy)quinolone, 465 mg). MS (ES+) m/z 420.0 [M+H]$^+$. $^1$H NMR (400 MHz, DMSO-d6) δ ppm 2.32 (s, 3 H) 3.77 (s, 3 H) 5.33 (s, 2 H) 7.00 (d, J=8.59 Hz, 2 H) 7.38 (d, J=8.34 Hz, 2 H) 7.48 (d, J=8.59 Hz, 2 H) 7.54 (d, J=8.59 Hz, 1 H) 7.69 (dd, J=8.72, 4.17 Hz, 1 H) 7.84 (d, J=8.34 Hz, 2 H) 8.47 (d, J=8.34 Hz, 1 H) 8.86 (dd, J=8.72, 1.39 Hz, 1 H) 8.91 (dd, J=4.04, 1.26 Hz, 1 H).

Step 3: 5-(p-tolylsulfonyl)quinolin-8-ol

To a slurry of 8-((4-methoxybenzyl)oxy)-5-tosylquinoline (500 mg, 1.192 mmol) in dichloromethane was added trifluoroacetic acid (0.092 ml, 1.192 mmol). The reaction was maintained at ambient temperature for 1 hour prior to concentration to an oily residue. Water was added and a gooey solid formed. The aqueous solution was neutralized with 6 M sodium hydroxide and diluted with dichloromethane. The layers were separated and organic dried over sodium sulfate. Concentration gave a sticky solid that was purified by automated normal-phase chromatography using 0-10% methanol/dichloromethane as an eluent. (420 mg, 85% yield). MS (ES+) m/z 301.0 [M+H]$^+$. $^1$H NMR (400 MHz, DMSO-d6) δ ppm 2.32 (s, 3 H) 3.34 (br. s., 1 H) 7.27 (d, J=8.34 Hz, 1 H) 7.37 (d, J=8.34 Hz, 2 H) 7.72 (dd, J=8.72, 4.17 Hz, 1 H) 7.83 (d, J=8.34 Hz, 2 H) 8.39 (d, J=8.34 Hz, 1 H) 8.88 (dd, J=8.84, 1.52 Hz, 1 H) 8.94 (dd, J=4.04, 1.52 Hz, 1 H).

Step 4: 7-iodo-5-(p-tolylsulfonyl)quinolin-8-ol

A solution of 5-(p-tolylsulfonyl)quinolin-8-ol (50 mg, 0.17 mmol) and N-iodosuccinimide (37.57 mg, 0.17 mmol) in chloroform was vigorously stirred at 40° C. After 1 hour, the resulting solution was filtered and the organic phase was washed with 10% aqueous sodium thiosulfate solution (1×2 ml) and layers separated. The solvent was removed by nitrogen stream and product suspended in ethyl acetate and diluted with diethyl ether to yield yellow solids. The solids were collected by filtration and dried. The solids were placed in a vacuum oven for several hours to remove trace solvent. (33.6 mg, 47% yield). MS (ES+) m/z 448.9 [M+Na]$^+$. $^1$H NMR (400 MHz, DMSO-d6) δ ppm 2.33 (s, 3 H) 7.39 (d, J=8.08 Hz, 2 H) 7.77 (dd, J=8.21, 4.17 Hz, 1 H) 7.89 (d, J=8.08 Hz, 2 H) 8.64 (s, 1 H) 8.86 (d, J=8.84 Hz, 1 H) 8.95 (d, J=4.29 Hz, 1 H).

The following analogs were synthesized using the Method N as described above.

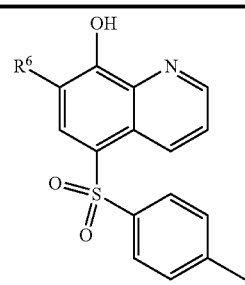

| Example | Name | R$^6$ | Data | Preparation Information |
|---|---|---|---|---|
| 108 | 7-bromo-5-(p-tolylsulfonyl)quinolin-8-ol | Br | MS (ES+) m/z 379.1 [M + H]$^+$ $^1$H NMR (400 MHz, DMSO-d6) δ ppm 2.33 (s, 3 H) 7.39 (d, J = 8.59 Hz, 2 H) 7.77 (dd, J = 8.59, 4.29 Hz, 1 H) 7.91 (d, J = 8.34 Hz, 2 H) 8.51 (s, 1 H) 8.88 (d, J = 7.83 Hz, 1 H) 8.96 (d, J = 4.04 Hz, 1 H) | Using N-bromosuccinimide |
| 109 | 7-chloro-5-(p-tolylsulfonyl)quinolin-8-ol | Cl | MS (ES+) m/z 334.0 [M + H]$^+$ $^1$H NMR (400 MHz, DMSO-d6) δ ppm 2.33 (s, 3 H) 7.39 (d, J = 8.59 Hz, 2 H) 7.77 (d, J = 8.72, 4.17 Hz, 1 H) 7.92 (d, J = 8.08 Hz, 2 H) 8.42 (s, 1 H) 8.89 (dd, J = 8.72, 1.39 Hz, 1 H) 8.99 (dd, J = 4.17, 1.39 Hz, 1 H) | Using N-chlorosuccinimide |

Example 110

7-fluoro-5-(p-tolylsulfonyl)quinolin-8-ol

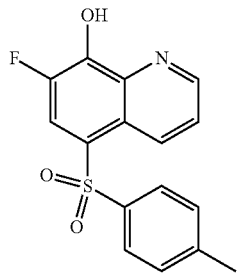 [SMILES: Cc1ccc(S(=O)(=O)c2cc(F)c(O)c3ncccc23)cc1]

Step 1: 7-fluoroquinolin-8-ol

To a solution of 2-amino-6-fluoro-phenol (2000 mg, 15.73 mmol) and nitrobenene (10 ml) in a sealable reaction pressure vessel was added in portions sulfuric acid (2 mL, 37.52 mmol). Glycerol (4.8 mL, 65.15 mmol) was added in one portion, and the solution turned to dark brown. The vessel was flushed with nitrogen, sealed and heated to 140° C. for 6 hours. The reaction mixture was cooled to ambient, diluted with (30 mL) ice/water mixture, extracted (2×200 mL) methyl tert-butyl ether. The aqueous phase was neutralized to pH-6-7 by slow addition of 6N sodium hydroxide. The resulting black precipitate was collected by filtration and the water solution was extracted with ethyl acetate 3 times. The organic extracts were combined with the black precipitate, concentrated in vacuo, and purified by automated normal-phase chromatography using 0-10% methanol/dichloromethane as an eluent. The title compound was isolated as a solid (1.56 g, 59% yield). MS (ES+) m/z 164.9 [M+H]$^+$. $^1$H NMR (400 MHz, DMSO-d6) δ ppm 7.43-7.49 (m, 1 H) 7.50-7.57 (m, 2 H) 8.37 (dd, J=8.21, 1.64 Hz, 1 H) 8.90 (dd, J=4.17, 1.64 Hz, 1 H) 10.26 (br. s., 1 H).

Step 2: 7-fluoro-5-iodo-quinolin-8-ol

A solution of 7-fluoroquinolin-8-ol (250 mg, 1.53 mmol) and N-iodosuccinimide (413.69 mg, 1.84 mmol) in chloroform was vigorously stirred at 40° C. After 15 minutes the reaction was diluted with dichloromethane, extracted (2×20 mL) 10% sodium thiosulfate solution and dried over sodium sulfate. The pale yellow solids were taken on in subsequent reactions without additional purification. (429.6 mg, 97% yield). MS (ES+) m/z 290.9 [M+H]$^+$.$^1$H NMR (400 MHz, DMSO-d6) δ ppm 7.67 (dd, J=8.59, 4.29 Hz, 1 H) 8.17 (d, J=10.61 Hz, 1 H) 8.25-8.35 (m, 1 H) 8.90 (dd, J=4.04, 1.52 Hz, 1 H) 10.62 (br. s., 1 H).

Step 3: 7-fluoro-5-iodo-8-benzyloxyqunioline

To a solution of 7-fluoro-5-iodo-quinolin-8-ol (425 mg, 1.47 mmol) in (5 mL) DMF was added sodium hydride, 60% suspension in mineral oil (70.58 mg, 1.76 mmol). After 5 minutes benzyl bromide (0.21 mL, 1.76 mmol) was added slowly dropwise. The reaction was maintained at ambient temperature. The reaction was quenched by addition of water. Ethyl acetate was added and the layers separated. The aqueous layer was extracted (2×20 mL) ethyl acetate. The organics were combined and dried over sodium sulfate. Concentration gave an oily residue that was purified by automated normal-phase chromatography using 0-100% ethyl acetate/hexanes as an eluent. (446.9 mg, 80% yield). MS (ES+) m/z 401.9 [M+2H]$^+$, $^1$H NMR (400 MHz, DMSO-d6) δ ppm 5.47 (s, 2 H) 7.28-7.41 (m, 3 H) 7.44-7.52 (m, 2 H) 7.69 (dd, J=8.59, 4.29 Hz, 1 H) 8.25 (d, J=10.11 Hz, 1 H) 8.36 (dd, J=8.72, 1.39 Hz, 1 H) 9.00 (dd, J=4.04, 1.52 Hz, 1 H).

Step 4: 8-benzyloxy-7-fluoro-5-(p-tolylsulfanyl)quinolone 4-mercaptotoluene (163.12 mg, 1.31 mmol), potassium carbonate (121.02 mg, 0.88 mmol) and 7-fluoro-5-iodo-8-benzyloxyqunioline (166 mg, 0.44 mmol) were charged in a microwave vial. The vial was placed under nitrogen and copper (I) iodide (4.17 mg, 0.02 mmol), ethylene glycol (0.02 mL, 0.44 mmol) and isopropyl alcohol (2 mL) were added at ambient temperature. The vial was submitted to microwave irradiation on high absorption at 100° C. for 30 minutes. The mixture was cooled to ambient temperature and filtered through a cake of Celite washing with ethyl acetate. Purification was accomplished by automated normal-phase chromatography using 0-30% ethyl acetate/hexanes as an eluent to afford the title compound (85.9 mg, 52% yield). MS (ES+) m/z 376.0 [M+H]$^+$. $^1$H NMR (400 MHz, DMSO-d6) δ ppm 2.27 (s, 3 H) 5.49 (s, 2 H) 7.13-7.23 (m, 4 H) 7.30-7.43 (m, 3 H) 7.45-7.54 (m, 2 H) 7.58 (d, J=10.61 Hz, 1 H) 7.63 (dd, J=8.59, 4.04 Hz, 1 H) 8.62 (dd, J=8.59, 1.77 Hz, 1 H) 9.04 (dd, J=4.04, 1.52 Hz, 1 H).

Step 5: 8-benzyloxy-7-fluoro-5-(p-tolylsulfonyl)quinolone

To a stirred solution of 8-benzyloxy-7-fluoro-5-(p-tolylsulfanyl)quinoline (100 mg, 0.27 mmol) in (2 mL) dry acetonitrile was added N-methylmorpholine N-oxide (93.61 mg, 0.80 mmol) at ambient temperature. After 5 minutes tetrapropylammonium perruthenate (4.68 mg, 0.01 mmol) was added to the mixture and warmed to 40° C. Additional tetrapropylammoniumperruthenate (1 equivalent) and N-methylmorpholine N-oxide (1 equivalent) were added after one hour and the reaction mixture was resubjected to the reaction conditions overnight. The mixture was cooled to ambient temperature and concentrated to a residue. The material was suspended in ethyl acetate and filtered through a cake of silica gel. The filtrate was concentrated and purified by automated normal-phase chromatography using 0-30% ethyl acetate/hexanes as an eluent to afford the title compound (60.2 mg, 55% yield). MS (ES+) m/z 408.0 [M+H]$^+$. $^1$H NMR (400 MHz, DMSO-d6) δ ppm 2.34 (s, 3 H) 5.61 (s, 2 H) 7.30-7.44 (m, 5 H) 7.47-7.54 (m, 2 H) 7.71 (dd, J=8.72, 4.17 Hz, 1 H) 7.90-7.98 (m, 2 H) 8.46 (d, J=10.61 Hz, 1 H) 8.90-8.97 (m, 1 H) 9.06 (dd, J=4.04, 1.52 Hz, 1 H).

Step 6: 7-fluoro-5-(p-tolylsulfonyl)quinolin-8-ol

A mixture of 8-benzyloxy-7-fluoro-5-(p-tolylsulfonyl) quinoline (70 mg, 0.17 mmol) dissolved in acetic acid (0.50 mL) was added hydrobromic acid (0.50 mL). The resultant mixture was heated to 100° C. for 3 hours. The material was cooled to ambient temperature and neutralized with 6 M sodium hydroxide. The aqueous solution was extracted (3×2 mL) dichloromethane, organics combined, filtered through a phase separator tube and concentrated to a residue. Purification was accomplished by automated normal-phase chromatography using with 0-10% methanol/dichloromethane as an eluent. The impure material was dissolved in a minimum amount of dichloromethane and purified by reversed phase HPLC-Gilson eluting 5-95% acetonitrile/water, 0.05% trifluoroacetic acid. An orange solid (38.3 mg, 70% yield) was obtained. MS (ES+) m/z 318.0 [M+H]+. 1H NMR (400 MHz, DMSO-d6) δ ppm 2.33 (s, 3 H) 3.42 (br. s, 1 H) 7.39 (d, J=8.34 Hz, 2 H) 7.71 (dd, J=8.72, 4.17 Hz, 1 H) 7.91 (d, J=7.83 Hz, 2 H) 8.42 (d, J=11.12 Hz, 1 H) 8.90 (dt, J=8.34, 1.01 Hz, 1 H) 8.97 (d, J=4.04 Hz, 1 H).

Example 111

7-methyl-5-pyrrolidin-1-ylsulfonyl-quinolin-8-ol

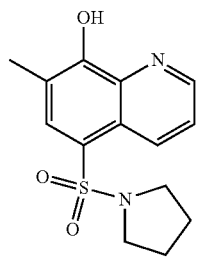 [SMILES: Cc1cc(S(=O)(=O)N2CCCC2)c2cccnc2c1O]

Step 1: 8-fluoro-7-methyl-quinoline 8-fluoro-7-methyl-quinoline was prepared in a similar manner as Example 110, step 1. The product was prepared from 2-fluoro-3-methyl-aniline (15.98 mmol) providing 2.29 g (89% yield). 1H NMR (400 MHz, DMSO-d6) δ ppm 2.46 (d, J=2.53 Hz, 3 H) 7.51 (dd, J=8.08, 7.07 Hz, 1 H) 7.57 (dd, J=8.34, 4.04 Hz, 1 H) 7.73 (d, J=8.34 Hz, 1 H) 8.39 (dt, J=8.34, 1.77 Hz, 1 H) 8.92 (dd, J=4.17, 1.64 Hz, 1 H).

Step 2: 8-fluoro-7-methyl-quinoline-5-sulfonyl chloride 8-fluoro-7-methyl-quinoline-5-sulfonyl chloride was prepared in a similar manner as in Method K, Step 1. The product was prepared from 8-fluoro-7-methyl-quinoline (3.1 mmol) providing 509.2 mg (63% yield) of the title compound. MS (ES+) m/z 260.9 [M+H]+. 1H NMR (400 MHz, DMSO-d6) δ ppm 2.51-2.52 (m, 3 H) 7.90 (dd, J=8.72, 4.67 Hz, 1 H) 8.01 (d, J=7.33 Hz, 1 H) 9.09 (dd, J=4.80, 1.52 Hz, 1 H) 9.48 (dt, J=8.72, 1.71 Hz, 1 H).

Step 3: 8-tert-butoxy-7-methyl-5-pyrrolidin-1-ylsulfonyl-quinoline 8-tert-butoxy-7-methyl-5-pyrrolidin-1-ylsulfonyl-quinoline was prepared in a similar manner as in Method K, Step 2. The product was prepared from 8-fluoro-7-methyl-quinoline-5-sulfonyl chloride (0.20 mmol) to give 45.2 mg (63% yield) of the title compound. MS (ES+) m/z 349.0 [M+H]+. 1H NMR (400 MHz, DMSO-d6) δ ppm 1.44 (s, 9 H) 1.72 (dt, J=6.51, 3.44 Hz, 4 H) 3.17-3.27 (m, 4 H) 3.34 (s, 3 H) 7.61-7.70 (m, 1 H) 8.06 (s, 1 H) 8.96-9.03 (m, 2 H).

Step 4: 7-methyl-5-pyrrolidin-1-ylsulfonyl-quinolin-8-ol 7-methyl-5-pyrrolidin-1-ylsulfonyl-quinolin-8-ol was prepared in a similar manner as in Method K, Step 3. The product was prepared from 8-tert-butoxy-7-methyl-5-pyrrolidin-1-ylsulfonyl-quinoline (0.129 mmol) to provide 35 mg (92% yield) of the title compound. MS (ES+) m/z 293.0 [M+H]+. 1H NMR (400 MHz, DMSO-d6) δ ppm 1.65-1.73 (m, 4 H) 2.43 (s, 3 H) 3.11-3.20 (m, 4 H) 7.76 (dd, J=8.84, 4.29 Hz, 1 H) 8.06 (d, J=0.51 Hz, 1 H) 8.98 (dd, J=4.29, 1.52 Hz, 1 H) 9.08 (dd, J=8.59, 1.52 Hz, 1 H).

Example 112

7-chloro-5-[4-[(4-fluorophenyl)methyl]piperazin-1-yl]sulfonyl-quinolin-8-ol—Method O

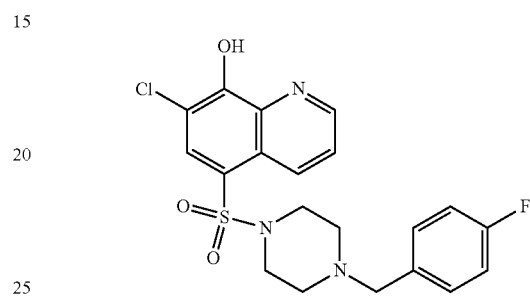

Step 1: 8-fluoroquinoline-5-sulfonyl chloride

8-Fluoroquinoline (2.5 g, 16.99 mmol) was added dropwise with stirring to chlorosulfonic acid (7.04 mL, 105.95 mmol). The resulting mixture was stirred at 110° C. for 18 h. The reaction mixture was added dropwise to ice-water with stirring. The solid was collected by filtration and air-dried to give the product as a beige solid (903 mg, 21.7% yield). MS (ES+) m/z 246.0 [M+H]+. 1H NMR (400 MHz, DMSO-d6) δ ppm: 7.56 (dd, J=10.86, 8.08 Hz, 3 H) 7.74 (dd, J=8.72, 4.17 Hz, 3 H) 7.98 (dd, J=8.08, 5.31 Hz, 3 H) 8.99 (dd, J=4.17, 1.64 Hz, 3 H) 9.27 (dt, J=8.72, 1.71 Hz, 3 H).

Step 2: 8-tert-butoxy-5-[4-[(4-fluorophenyl)methyl]piperazin-1-yl]sulfonyl-quinoline 8-fluoroquinoline-5-sulfonyl chloride (250 mg, 1.02 mmol) was dissolved in THF (1.5 mL). To this solution was added DIPEA (531.85 uL, 3.05 mmol), followed by 1-[(4-fluorophenyl)methyl]piperazine (197.68 mg, 1.02 mmol). The resulting mixture was stirred at room temperature for 15 min. Complete conversion to intermediate sulfonamide was indicated by LCMS. A solution of potassium t-butoxide (3053.5 uL, 3.05 mmol, 1M in THF) was added and the resulting mixture stirred at ambient temperature for 1 hour. The reaction mixture was treated with about 2 mL saturated NaHCO3 and about 2 mL ethyl acetate, agitated vigorously and the layers separated. Solvent was removed from the organic fraction in vacuo to give a brown residue. The material was taken on without additional purification and or characterization. MS (ES+) m/z 458.0 [M+H]+.

Step 3: 5-[4-[(4-fluorophenyl)methyl]piperazin-1-yl]sulfonylquinolin-8-ol

Crude (8-tert-butoxy-5-[4-[(4-fluorophenyl)methyl]piperazin-1-yl]sulfonyl-quinoline (465.34 mg, 1.02 mmol) dissolved in 2 mL THF was treated with 4M HCl in dioxane (0.25 mL, 1.02 mmol) overnight. The suspensions were diluted with ether and solids collected by filtration. The material was used in subsequent reactions without additional purification and/or characterization. MS (ES+) m/z 402.0 [M+H]+.

Step 4: 7-chloro-5-[4-[(4-fluorophenyl)methyl]piperazin-1-yl]sulfonyl-quinolin-8-ol A solution of 5-[4-[(4-fluorophenyl)methyl]piperazin-1-yl]sulfonylquinolin-8-ol (150 mg, 0.370 mmol) suspended in chloroform (2 mL) was added DIPEA (0.07 mL, 0.370 mmol). When the mixture became a solution, N-chlorosuccinimide (49.89 mg, 0.370 mmol) was added at ambient temperature. LC/MS at 1 hour shows only starting material. The reaction was heated to 40° C. and an additional equivalent of N-chlorosuccinimide was added. The vial was cooled to ambient temperature and filtered. The solids were suspended between water and 10% sodium thiosulfate solution for 1 hour. The suspension was filtered and yellow solids obtained. MS (ES+) m/z 436.0 [M+H]+. $^1$H NMR (400 MHz, DMSO-d6) δ ppm: 8.98 (d, J=4.04 Hz, 1 H) 8.95 (dd, J=8.84, 1.52 Hz, 1 H) 8.05 (s, 1 H) 7.76 (dd, J=8.84, 4.29 Hz, 1 H) 7.24 (dd, J=8.72, 5.68 Hz, 2 H) 7.08 (t, J=8.84 Hz, 2 H) 3.31-3.37 (m, 2 H) 3.02 (br. s., 4 H) 2.36 (br. s., 4 H).

Example 113

7-fluoro-5-pyrrolidin-1-ylsulfonyl-quinolin-8-ol—Method P

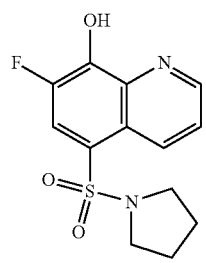 [SMILES: O=S(=O)(c1cc(F)c(O)c2ncccc12)N1CCCC1]

Step 1: 7-fluoroquinolin-8-ol

To a solution of 2-amino-6-fluoro-phenol (2000 mg, 15.73 mmol) and nitrobenzene (10 mL) in a sealable reaction vessel was added in portions sulfuric acid (2 mL, 37.52 mmol). Glycerol (4.8 mL, 65.15 mmol) was added in one portion. The vessel was flushed with nitrogen, sealed and heated to 140° C. for 6 hours. The reaction mixture was cooled to ambient temperature, nitrobenzene decanted off, oily brown/black residue diluted with 30 ml ice/water mixture, extracted (2×200 ml) with methyl t-butyl ether. The aqueous phase was neutralized to pH=6-7 by slow addition of 6N NaOH. The resulting black precipitate was collected (pouring over a pad of Celite) and the water solution was extracted with ethyl acetate 3 times. The organics were combined and concentrated to a residue and combined with the black solids collected by filtration. The material was purified by SiO$_2$ chromatography-Biotage eluting 0-10% methanol/dichloromethane yielding a pale green/white solid (1.39 g, 8.54 mmol, 54% yield). MS (ES+) m/z 164.0 [M+H]+. $^1$H NMR (400 MHz, DMSO-d6) δ ppm: 10.24 (br. s., 1 H) 8.90 (dd, J=4.17, 1.64 Hz, 1 H) 8.37 (dd, J=8.34, 1.77 Hz, 1 H) 7.50-7.58 (m, 2 H) 7.41-7.49 (m, 1 H).

Step 2: 7-fluoro-5-pyrrolidin-1-ylsulfonyl-quinolin-8-ol

To a suspension of in 7-fluoroquinolin-8-ol (0.12 mL, 0.92 mmol) in 5 ml dichloroethane was added chlorosulfonic acid (20 drops) at ambient temperature. The resultant solution was heated to reflux overnight. The reaction mixture was cooled to 0° C. and pyrrolidine (1 mL, 12.18 mmol) was added. The reaction mixture was allowed to warm to ambient temperature and concentrated to a residue. Purification was accomplished by reversed phase HPLC eluting 10-100% acetonitrile/water with 0.05% trifluoroacetic acid as modifier. The product containing fractions were pooled and concentrated to a tan solid (123.4 mg, 33%) as the trifluoroacetic acid salt. MS (ES+) m/z 297.1 [M+H]. $^1$H NMR (400 MHz, DMSO-d6) δ ppm 1.71 (dt, J=6.51, 3.44 Hz, 4 H) 3.17-3.23 (m, 4 H) 7.77 (dd, J=8.84, 4.04 Hz, 1 H) 8.09 (d, J=10.86 Hz, 1 H) 9.03 (dd, J=4.17, 1.39 Hz, 1 H) 9.07 (dd, J=8.84, 1.52 Hz, 1 H).

The following compounds were synthesized according to one of the previous methods.

| Ex | Structure | Name | Data | Prep info |
|---|---|---|---|---|
| 114 | (structure) | 5-[4-[(4-fluorophenyl)methyl]piperazin-1-yl]sulfonyl-7-methyl-quinolin-8-ol | MS (ES+) m/z 416.0 [M + H]+ $^1$H NMR (400 MHz, DMSO-d6) δ ppm: 9.31-9.56 (m, 1 H) 8.86-9.03 (m, 2 H) 8.05 (s, 1 H) 7.73 (dd, J = 8.84, 4.29 Hz, 1 H) 7.44 (d, J = 5.31 Hz, 2 H) 7.28 (t, J = 8.72 Hz, 2 H) 4.28 (br. s., 2 H) 3.70-3.88 (m, 2 H) 3.23-3.40 (m, 2H) 2.99-3.17 (m, 2H) 2.56-2.73 (m, 2H) 2.41 (s, 3 H) | N |

| Ex | Structure | Name | Data | Prep info |
|---|---|---|---|---|
| 115 | 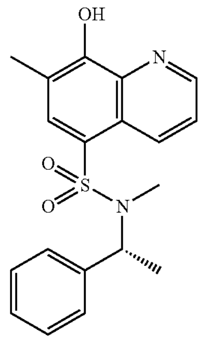 [SMILES: Cc1cc(S(=O)(=O)N(C)[C@H](C)c2ccccc2)c2cccnc2c1O] | 8-hydroxy-N,7-dimethyl-N-[(1R)-1-phenylethyl]quinoline-5-sulfonamide | MS (ES+) m/z 357.0 [M + H]$^+$ $^1$H NMR (400 MHz, DMSO-d6) δ ppm: 10.72-10.92 (m, 1 H) 8.98 (dd, J = 4.04, 1.52 Hz, 1 H) 8.90 (dd, J = 8.84, 1.52 Hz, 1 H) 8.11 (s, 1 H) 7.73 (dd, J = 8.59, 4.04 Hz, 1 H) 7.16-7.34 (m, 4 H) 5.21 (d, J = 7.07 Hz, 1 H) 2.52 (d, J = 2.53 Hz, 3 H) 2.41 (s, 3H) 1.23-1.30 (m, 3 H). | N |
| 116 | 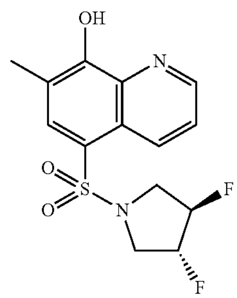 [SMILES: Cc1cc(S(=O)(=O)N2C[C@@H](F)[C@H](F)C2)c2cccnc2c1O] | 5-[(3R,4R)-3,4-difluoropyrrolidin-1-yl]sulfonyl-7-methyl-quinolin-8-ol | MS (ES+) m/z 329.0 [M + H]$^+$ $^1$H NMR (400 MHz, Chloroform-d) δ ppm: 8.98-9.14 (m, 2 H) 8.18 (d, J = 6.57 Hz, 1 H) 7.54-7.68 (m, 1 H) 5.14-5.25 (m, 1 H) 5.02-5.13 (m, 1 H) 3.56-3.88 (m, 4 H) 2.59 (d, J = 2.53 Hz, 3 H) | N |
| 117 | 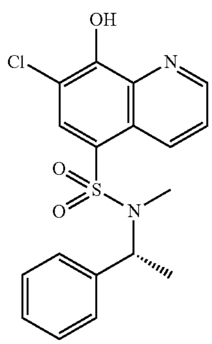 [SMILES: C[C@H](c1ccccc1)N(C)S(=O)(=O)c1cc(Cl)c(O)c2ncccc12] | 7-chloro-8-hydroxy-N-methyl-N-[(1R)-1-phenylethyl]quinoline-5-sulfonamide | MS (ES+) m/z 377.0 [M + H]$^+$ $^1$H NMR (400 MHz, DMSO-d6) δ ppm: 9.05 (dd, J = 4.17, 1.39 Hz, 1 H) 8.93 (dd, J = 8.84, 1.52 Hz, 1 H) 8.17 (s, 1 H) 7.83 (dd, J = 8.84, 4.04 Hz, 1 H) 7.19-7.35 (m, 5 H) 5.20-5.31 (m, 1 H) 2.56 (s, 3 H) 1.29 (d, J = 7.07 Hz, 3H) | O |
| 118 | 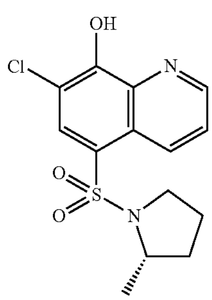 [SMILES: C[C@H]1CCCN1S(=O)(=O)c1cc(Cl)c(O)c2ncccc12] | 7-chloro-5-[(2S)-2-methylpyrrolidin-1-yl]sulfonyl-quinolin-8-ol | MS (ES+) m/z 327.0 [M + H]$^+$ $^1$H NMR (400 MHz, DMSO-d6) δ ppm: 9.02-9.08 (m, 2H) 8.12 (s, 1H) 7.84 (dd, J = 8.72, 4.17 Hz, 1 H) 3.82 (td, J = 6.88, 3.92 Hz, 1 H) 3.26-3.36 (m, 1 H) 3.17 (dt, J = 9.92, 7.17 Hz, 1 H) 1.66-1.88 (m, 2H) 1.56 (dd, J = 6.95, 4.93 Hz, 1 H) 1.47 (dd, J = 10.11, 6.06 Hz, 1H) 1.15 (d, J = 6.32 Hz, 3 H) | O |
| 119 | 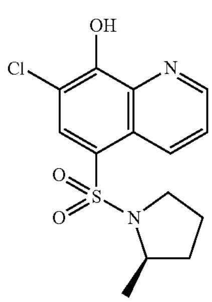 [SMILES: C[C@@H]1CCCN1S(=O)(=O)c1cc(Cl)c(O)c2ncccc12] | 7-chloro-5-[(2R)-2-methylpyrrolidin-1-yl]sulfonyl-quinolin-8-ol | MS (ES+) m/z 327.0 [M + H]$^+$ $^1$H NMR (400 MHz, DMSO-d6) δ ppm: 9.02-9.08 (m, 2 H) 8.12 (s, 1 H) 7.84 (dd, J = 8.72, 4.17 Hz, 1 H) 3.82 (td, J = 6.88, 3.92 Hz, 1 H) 3.26-3.36 (m, 1 H) 3.17 (dt, J = 9.92, 7.17 Hz, 1 H) 1.66-1.88 (m, 2H) 1.56 (dd, J = 6.95, 4.93 Hz, 1 H) 1.47 (dd, J = 10.11, 6.06 Hz, 1 H) 1.15 (d, J = 6.32 Hz, 3 H) | O |

| Ex | Structure | Name | Data | Prep info |
|---|---|---|---|---|
| 120 | 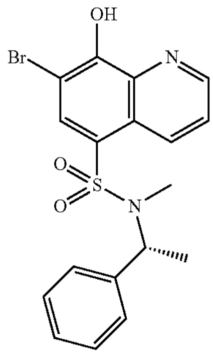 [SMILES: C[C@H](c1ccccc1)N(C)S(=O)(=O)c1cc(Br)c(O)c2ncccc12] | 7-bromo-8-hydroxy-N-methyl-N-[(1R)-1-phenylethyl]quinoline-5-sulfonamide | MS (ES+) m/z 422.0 [M + H]$^+$ $^1$H NMR (400 MHz, DMSO-d6) δ ppm: 8.99-9.10 (m, 1 H) 8.86-8.96 (m, 1 H) 8.27 (s, 1 H) 7.85 (dd, J = 8.72, 4.17 Hz, 1 H) 7.13-7.37 (m, 5 H) 5.25 (d, J = 6.82 Hz, 1 H) 2.51-2.59 (m, 3 H) 1.30 (d, J = 6.82 Hz, 3 H) | O |
| 121 | 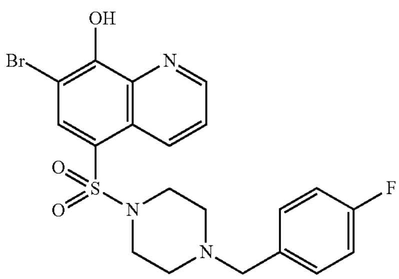 [SMILES: O=S(=O)(c1cc(Br)c(O)c2ncccc12)N1CCN(Cc2ccc(F)cc2)CC1] | 7-bromo-5-[4-[(4-fluorophenyl)methyl]piperazin-1-yl]sulfonyl-quinolin-8-ol | MS (ES+) m/z 482.0 [M + H]$^+$ $^1$H NMR (400 MHz, DMSO-d6) δ ppm: 9.05 (dd, J = 4.04, 1.52 Hz, 1 H) 8.96 (dd, J = 8.72, 1.39 Hz, 1 H) 8.22 (s, 1 H) 7.84 (dd, J = 8.84, 4.29 Hz, 1 H) 7.43 (br. s., 2 H) 7.26 (t, J = 7.96 Hz, 2 H) 4.21 (br. s., 2H) 3.78 (br. s., 4 H) 3.06 (br. s., 4 H) | O (Using NBS in step 3) |
| 122 | 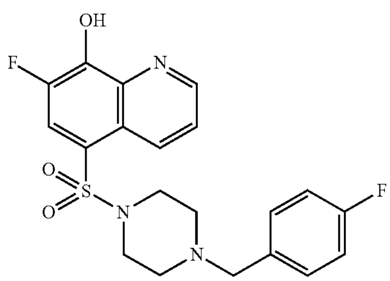 [SMILES: O=S(=O)(c1cc(F)c(O)c2ncccc12)N1CCN(Cc2ccc(F)cc2)CC1] | 7-fluoro-5-[4-[(4-fluorophenyl)methyl]piperazin-1-yl]sulfonyl-quinolin-8-ol | MS (ES+) m/z 420.0 [M +H ]$^+$. $^1$H NMR (400 MHz, DMSO-d6) δ ppm: 9.05 (d, J = 4.29 Hz, 1 H) 8.97 (d, J = 7.07 Hz, 1 H) 8.15 (d, J = 10.86 Hz, 1 H) 7.78 (dd, J = 8.97, 4.17 Hz, 1 H) 7.45 (d, J = 5.31 Hz, 2 H) 7.30 (t, J = 8.72 Hz, 2 H) 4.29 (br, s., 2 H) 3.84 (br. s., 2 H) 3.22-3.42 (m, 2 H) 3.10 (br. s., 2 H) 2.65-2.83 (m, 2 H). | P |
| 123 | 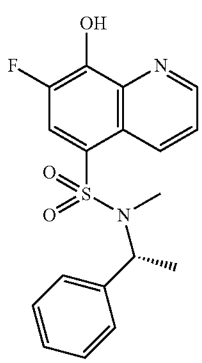 [SMILES: C[C@H](c1ccccc1)N(C)S(=O)(=O)c1cc(F)c(O)c2ncccc12] | 7-fluoro-8-hydroxy-N-methyl-N-[(1R)-1-phenylethyl]quinoline-5-sulfonamide | MS (ES+) m/z 361.0 [M + H]$^+$ $^1$H NMR (400 MHz, DMSO-d6) δ ppm: 9.00-9.10 (m, 1 H) 8.95 (dd, J = 8.84, 1.52 Hz, 1 H) 8.18 (d, J = 10.86 Hz, 1 H) 7.78 (dd, J = 8.84, 4.04 Hz, 1 H) 7.13-7.35 (m, 5 H) 5.16-5.32 (m, 1 H) 2.57 (s, 3 H) 1.27 (d, J = 6.82 Hz, 3H) | P |

REFERENCES

Apud, J. A. and D. R. Weinberger (2007). "Treatment of cognitive deficits associated with schizophrenia—Potential role of catechol-O-methyltransferase inhibitors." Cns Drugs 21(7): 535-557.

Bonifacio, M. J., P. N. Palma et al. (2007). "Catechol-O-methyltransferase and its inhibitors in Parkinson's disease." Cns Drug Reviews 13(3): 352-379.

Borchardt, R. T., D. R. Thakker et al. (1976). "Catechol O-Methyltransferase .8. Structure-Activity-Relationships for Inhibition by 8-Hydroxyquinolines." Journal of Medicinal Chemistry 19(4): 558-560.

Ciliax, B. J., C. Heilman et al. (1995). "The Dopamine Transporter—Immunochemical Characterization and Localization in Brain." Journal of Neuroscience 15(3): 1714-1723.

Fatemi, S. H. and T. D. Folsom (2009). "The Neurodevelopmental Hypothesis of Schizophrenia, Revisited." Schizophrenia Bulletin 35(3): 528-548.

Goldman-Rakic, P. S., S. A. Castner et al. (2004). "Targeting the dopamine D-1 receptor in schizophrenia: insights for cognitive dysfunction." Psychopharmacology 174(1): 3-16.

Howes, O. D. and S. Kapur (2009). "The Dopamine Hypothesis of Schizophrenia: Version III—The Final Common Pathway." Schizophrenia Bulletin 35(3): 549-562.

Lin Y. et al. (2012), "Detecting S-adenosyl-1-methionine-induced conformational change of a histone methyltransferase using a homogeneous time-resolved fluorescence-based binding assay" Analytical Biochemistry, 423(1): 171-177. Kaenmaki, M., A. Tammimaki et al. (2010). "Quantitative role of COMT in dopamine clearance in the prefrontal cortex of freely moving mice." J Neurochem 114(6): 1745-1755.

Lachman, H. M., D. F. Papolos et al. (1996). "Human catechol-O-methyltransferase pharmacogenetics: Description of a functional polymorphism and its potential application to neuropsychiatric disorders." Pharmacogenetics 6(3): 243-250.

Learmonth, D. A., L. E. Kiss et al. (2010). "The Chemistry of Catechol O-Methyltransferase Inhibitors." Basic Aspects of Catechol-O-Methyltransferase and the Clinical Applications of Its Inhibitors 95: 119-162.

Marenco, S. and D. R. Weinberger (2000). "The neurodevelopmental hypothesis of schizophrenia: Following a trail of evidence from cradle to grave." Development and Psychopathology 12(3): 501-527.

Nutt, J. G. and J. H. Fellman (1984). "Pharmacokinetics of Levodopa." Clinical Neuropharmacology 7(1): 35-49.

Nutt, J. G., W. R. Woodward et al. (1985). "The Effect of Carbidopa on the Pharmacokinetics of Intravenously Administered Levodopa—the Mechanism of Action in the Treatment of Parkinsonism." Annals of Neurology 18(5): 537-543.

Olanow, C. W. and P. B. Watkins (2007). "Tolcapone." Clinical Neuropharmacology 30(5): 287-294.

Pickard, B. (2011). "Progress in defining the biological causes of schizophrenia." Expert Reviews in Molecular Medicine 13.

Russ, H., et al. (1999). "Detection of tolcapone in the cerebrospinal fluid of parkinsonian subjects." Naunyn-Schmiedeberg's Archives of Pharmacology 360(6): 719-720.

Yavich, L., M. M. Forsberg et al. (2007). "Site-specific role of catechol-O-methyltransferase in dopamine overflow within prefrontal cortex and dorsal striatum." Journal of Neuroscience 27(38): 10196-10202.

The invention claimed is:

1. A COMT-inhibiting compound in accordance with formula I, or a pharmaceutically acceptable salt thereof:

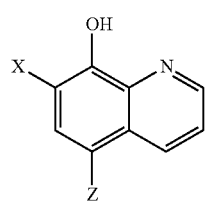

I wherein:
X is selected from halogen, C≡N, CF$_3$, and C$_3$-C$_4$ alkyl;
Z is selected from SO$_2$R$^1$ and SO$_2$NR$^2$R$^3$;
R$^1$ is selected from C$_1$-C$_{10}$ alkyl, C$_3$-C$_{10}$ cycloalkyl, aryl, aralkyl, heterocyclyl, heteroaryl and heteroarylalkyl, any of which may be substituted with one or more groups selected from halogen, C≡N, CF$_3$, OH, C$_1$-C$_4$ alkyl, C$_2$-C$_4$ alkenyl, alkoxy, nitro, amino, C$_1$-C$_4$ alkylamino, oxo, C$_3$-C$_{10}$ cycloalkyl, acyl, aryl, aralkyl, heterocyclyl, heteroaryl, CON(R)$_2$, SO$_2$R, and SO$_2$N(R)$_2$, where each R is independently C$_1$-C$_4$ alkyl or where (R)$_2$ forms a carbocyclic ring;

R$^2$ and R$^3$ are independently selected from-hydrogen C$_3$-C$_{10}$ alkyl, C$_3$-C$_{10}$ cycloalkyl, aryl, aralkyl, heterocyclyl, heteroaryl and heteroarylalkyl, any of which may be substituted with one or more groups selected from halogen, C≡N, CF$_3$, OH, C$_1$-C$_4$ alkyl, C$_2$-C$_4$ alkenyl, alkoxy, nitro, amino, C$_1$-C$_4$ alkylamino, oxo, C$_3$-C$_{10}$ cycloalkyl, acyl, aryl, aralkyl, heterocyclyl, heteroaryl, CON(R)$_2$, SO$_2$R, and SO$_2$N(R)$_2$, where each R is independently C$_1$-C$_4$ alkyl or where (R)$_2$ forms a carbocyclic ring, with the proviso that at least one of R$^2$ or R$^3$ is different from hydrogen; or R$^2$ and R$^3$ may together form a 3-10 membered monocyclic, bicyclic or spirocyclic nitrogen-containing ring system that contains 0-3 additional heteroatoms selected from oxygen (O), nitrogen (N), and sulfur (S), and which may be further substituted with one or more groups selected from halogen, C≡N, CF$_3$, OH, C$_1$-C$_4$ alkyl or C$_2$-C$_4$ alkenyl, C$_3$-C$_6$ cycloalkyl, alkoxy, nitro, amino, C$_1$-C$_4$ alkoxycarbonyl, acyl, C$_1$-C$_4$ alkylamino, oxo, SO$_2$CH$_3$, aryl, aralkyl, heterocyclyl, heteroaryl and heteroarylalkyl;

and with the provisos that:
when X is Cl and Z is SO$_2$R$^1$, R$^1$ is not C$_3$ alkyl, C$_4$ alkyl, C$_5$-C$_6$ cycloalkyl, thiazolyl, pyridyl, pyridyl-N-oxide, and phenyl substituted with one or two groups selected from fluoro, chloro, methyl, trifluoromethyl, phenyl and tert-butyl; or when X is Cl and Z is SO$_2$NR$^2$R$^3$, R$^2$ and R$^3$ do not together form an unsubstituted, 1-pyrrolidinyl ring; or when X is F and Z is SO$_2$R$^1$, R$^1$ is not pyridyl, cyclopentyl and phenyl substituted with fluoro, or trifluoromethyl.

2. A compound selected from the group consisting of:
5-(4-fluorophenyl)sulfonylquinolin-8-ol;
5-(3,4-dimethylphenyl)sulfonylquinolin-8-ol;
5-(3,5-dimethylphenyl)sulfonylquinolin-8-ol;
5-(4-tert-butylphenyl)sulfonylquinolin-8-ol;
5-(3-phenylphenyl)sulfonylquinolin-8-ol;
5-(m-tolylsulfonyl)quinolin-8-ol;
5-(3,5-dichlorophenyl)sulfonylquinolin-8-ol;
5-(4-chlorophenyl)sulfonylquinolin-8-ol;
5-(2,4-dimethylphenyl)sulfonylquinolin-8-ol;
5-[4-(trifluoromethyl)phenyl]sulfonylquinolin-8-ol;
5-(2-naphthylsulfonyl)quinolin-8-ol;
5-[3-(trifluoromethyl)phenyl]sulfonylquinolin-8-ol;
5-(3-chlorophenyl)sulfonylquinolin-8-ol;
5-(3,4-dichlorophenyl)sulfonylquinolin-8-ol;
5-(2-pyridylsulfonyl)quinolin-8-ol;
5-(4-pyridylsulfonyl)quinolin-8-ol;
5-(3-pyridylsulfonyl)quinolin-8-ol;
5-(4-fluoro-2-methyl-phenyl)sulfonylquinolin-8-ol;
5-[2-(trifluoromethyl)phenyl]sulfonylquinolin-8-ol;
5-[3-(4-pyridyl)phenyl]sulfonylquinolin-8-ol;
5-[3-(3-chloro-4-fluoro-phenyl)phenyl]sulfonylquinolin-8-ol;
5-[3-(5-quinolyl)phenyl]sulfonylquinolin-8-ol;
5-[3-(1H-indazol-4-yl)phenyl]sulfonylquinolin-8-ol;
5-[(3-methyl-4-pyridyl)sulfonyl]quinolin-8-ol;

5-[1-[(2-chlorophenyl)methyl]benzimidazol-4-yl]sulfonylquinolin-8-ol;
5-[2-(p-tolyl)ethylsulfonyl]quinolin-8-ol;
5-cyclohexylsulfonylquinolin-8-ol;
5-cyclopentylsulfonylquinolin-8-ol;
5-(p-tolylmethylsulfonyl)quinolin-8-ol;
5-ethylsulfonylquinolin-8-ol;
5-(4-piperidylsulfonyl)quinolin-8-ol;
5-[[1-[(4-fluorophenyl)methyl]-4-piperidyl]sulfonyl]quinolin-8-ol;
5-[[1-[(2,3-dichlorophenyl)methyl]-4-piperidyl]sulfonyl]quinolin-8-ol;
5-[[1-(2,3-dimethylphenyl)-4-piperidyl]sulfonyl]quinolin-8-ol;
5-(3,4-dihydro-1H-isoquinolin-2-ylsulfonyl)quinolin-8-ol;
5-(4-phenylpiperazin-1-yl)sulfonylquinolin-8-ol ;
8-hydroxy-N-[(3-methoxyphenyl)methyl]-N-methyl-quinoline-5-sulfonamide;
5-(4-benzylpiperazin-1-yl)sulfonylquinolin-8-ol ;
8-hydroxy-N-(4-methylbenzyl)quinoline-5-sulfonamide;
N-benzyl-8-hydroxy-N-methylquinoline-5-sulfonamide;
8-hydroxy-N-(4-methylphenyl)-N-methylquinoline-5-sulfonamide;
5-isoindolin-2-ylsulfonylquinolin-8-ol;
8-hydroxy-N-methyl-N-phenethyl-quinoline-5-sulfonamide;
N-[(4-fluorophenyl)methyl]-8-hydroxy-N-methyl-quinoline-5-sulfonamide;
8-hydroxy-N-methyl-N-[(1R)-1-phenylethyl]quinoline-5-sulfonamide;
8-hydroxy-N-methyl-N-[(1S)-1-phenylethyl]quinoline-5-sulfonamide;
N-[(2-fluorophenyl)methyl]-8-hydroxy-N-methyl-quinoline-5-sulfonamide;
N-[(3-chlorophenyl)methyl]-8-hydroxy-N-methyl-quinoline-5-sulfonamide;
8-hydroxy-N-methyl-N-(3-pyridylmethyl)quinoline-5-sulfonamide;
8-hydroxy-N-methyl-N-(2-naphthylmethyl)quinoline-5-sulfonamide;
N-benzyl-N-ethyl-8-hydroxy-quinoline-5-sulfonamide;
N-benzyl-N-(2-dimethylaminoethyl)-8-hydroxy-quinoline-5-sulfonamide;
5-(2-phenylpyrrolidin-1-yl)sulfonylquinolin-8-ol;
5-(4-methylpiperazin-1-yl)sulfonylquinolin-8-ol;
5-[(2-phenyl-1-piperidyl)sulfonyl]quinolin-8-ol;
5-(3-(4-fluorophenyl)pyrrolidin-1-yl)sulfonylquinolin-8-ol;
N-[(4-(trifluoromethyl)phenyl)methyl]-8-hydroxy-N-methyl-quinoline-5-sulfonamide;
N-ethyl-8-hydroxy-N-(4-pyridylmethyl)quinoline-5-sulfonamide;
5-(6,8-dihydro-5H-1,7-naphthyridin-7-ylsulfonyl)quinolin-8-ol;
5-[4-(5-chloro-2-pyridyl)piperazin-1-yl]sulfonylquinolin-8-ol;
5-[(3R,4R)-3,4-difluoropyrrolidin-1-yl]sulfonylquinolin-8-ol;
5-[2-(o-tolyl)pyrrolidin-1-yl]sulfonylquinolin-8-ol;
5-[2-(3-pyridyl)pyrrolidin-1-yl]sulfonylquinolin-8-ol;
5-[(4-phenyl-1-piperidyl)sulfonyl]quinolin-8-ol;
5-[2-(4-fluorophenyl)pyrrolidin-1-yl]sulfonylquinolin-8-ol;
5-(2-benzylpyrrolidin-1-yl)sulfonylquinolin-8-ol;
5-(2-cyclohexylpyrrolidin-1-yl)sulfonylquinolin-8-ol ;
5-[2-(4-methoxyphenyl)pyrrolidin-1-yl]sulfonylquinolin-8-ol;
5-(2-isopropylpyrrolidin-1-yl)sulfonylquinolin-8-ol;
5-[2-(4-pyridyl)pyrrolidin-1-yl]sulfonylquinolin-8-ol;
5-[2-(2-pyridyl)pyrrolidin-1-yl]sulfonylquinolin-8-ol;
5-[2-[2-(trifluoromethyl)phenyl]pyrrolidin-1-yl]sulfonylquinolin-8-ol;
5-(2-isobutylpyrrolidin-1-yl)sulfonylquinolin-8-ol;
5-[(4-hydroxy-4-phenyl-1-piperidyl)sulfonyl]quinolin-8-ol;
5-[(4-benzyl-1-piperidyl)sulfonyl]quinolin-8-ol;
[1-[(8-hydroxy-5-quinolyl)sulfonyl]-4-piperidyl]-phenyl-methanone;
1-[1-[(8-hydroxy-5-quinolyl)sulfonyl]-4-phenyl-4-piperidyl]ethanone;
8-[(8-hydroxy-5-quinolyl)sulfonyl]-1-phenyl-1,3,8-triazaspiro[4.5]decan-4-one;
methyl 4-[(8-hydroxy-5-quinolyl)sulfonyl]piperazine-1-carboxylate;
5-[4-(3-methoxypropyl)piperazin-1-yl]sulfonylquinolin-8-ol;
2-[4-[(8-hydroxy-5-quinolyl)sulfonyl]piperazin-1-yl]benzonitrile;
5-(3-azabicyclo[3.2.2]nonan-3-ylsulfonyl)quinolin-8-ol;
5-[4-(2-phenylphenyl)piperazin-1-yl]sulfonylquinolin-8-ol;
5-[4-(2, 5-dimethylphenyl)piperazin-1-yl]sulfonylquinolin-8-ol;
5-[4-[4-(trifluoromethyl)phenyl]piperazin-1-yl]sulfonylquinolin-8-ol;
5-[4-[bis(4-fluorophenyl)methyl]piperazin-1-yl]sulfonylquinolin-8-ol;
5-[4-(4-fluorophenyl)piperazin-1-yl]sulfonylquinolin-8-ol;
5-[4-(2,3-dichlorophenyl)piperazin-1-yl]sulfonylquinolin-8-ol;
5-[4-(1,2-benzothiazol-3-yl)piperazin-1-yl]sulfonylquinolin-8-ol;
5-[3-[4-(trifluoromethoxy)phenoxy]azetidin-1-yl]sulfonylquinolin-8-ol;
5-[4-(2,3-dimethylphenyl)piperazin-1-yl]sulfonylquinolin-8-ol;
5-[4-[(4-fluorophenyl)methyl]piperazin-1-yl]sulfonylquinolin-8-ol;
5-[(3-phenyl-1-piperidyl)sulfonyl]quinolin-8-ol;
tert-butyl 4-[(8-hydroxy-5-quinolyl)sulfonyl]piperazine-1-carboxylate;
5-piperazin-1-ylsulfonylquinolin-8-ol;
tert-butyl 4-[(8-hydroxy-5-quinolyl)sulfonyl]-3-methyl-piperazine-1-carboxylate;
5-(2-methylpiperazin-1-yl)sulfonylquinolin-8-ol;
7-iodo-5-(p-tolylsulfonyl)quinolin-8-ol;
7-bromo-5-(p-tolylsulfonyl)quinolin-8-ol;
7-chloro-5-(p-tolylsulfonyl)quinolin-8-ol;
7-fluoro-5-(p-tolylsulfonyl)quinolin-8-ol;
7-methyl-5-pyrrolidin-1-ylsulfonyl-quinolin-8-ol;
7-chloro-5-[4-[(4-fluorophenyl)methyl]piperazin-1-yl]sulfonyl-quinolin-8-ol;
7-fluoro-5-[4-[(4-fluorophenyl)methyl]piperazin-1-yl]sulfonyl-quinolin-8-ol;
5[4-[(4-fluorophenyl)methyl]piperazin-1-yl]sulfonyl-7-methyl-quinolin-8-ol;
8-hydroxy-N,7-dimethyl-N-[(1R)-1-phenylethyl]quinoline-5-sulfonamide;
5-[(3R,4R)-3,4-difluoropyrrolidin-1-yl]sulfonyl-7-methyl-quinolin-8-ol;

7-chloro-8-hydroxy-N-methyl-N-[(1R)-1-phenylethyl]quinoline-5-sulfonamide;
7-chloro-5-[(2S)-2-methylpyrrolidin-1-yl]sulfonyl-quinolin-8-ol;
7-chloro-5-[(2R)-2-methylpyrrolidin-1-yl]sulfonyl-quinolin-8-ol;
7-bromo-8-hydroxy-N-methyl-N-[(1R)-1-phenylethyl]quinoline-5-sulfonamide;
7-bromo-5-[4-[(4-fluorophenyl)methyl]piperazin-1-yl]sulfonyl-quinolin-8-ol;
7-fluoro-5-pyrrolidin-1-ylsulfonyl-quinolin-8-ol;
7-fluoro-8-hydroxy-N-methyl-N-[(1R)-1-phenylethyl]quinoline-5-sulfonamide;
5-(p-tolylsulfonyl)-7-(trifluoromethyl)quinolin-8-ol;
5-cyclopentylsulfonyl-7-(trifluoromethyl)quinolin-8-ol;
5-[[1-(4-fluorophenyl)-4-piperidyl]sulfonyl]quinolin-8-ol; and
5-[(2-methylpyrrolidin-1-yl)sulfonyl]quinolin-8-ol.

3. The pharmaceutical composition comprising a catechol O-methyltransferase (COMT) enzyme-inhibiting compound of claim 1, or a pharmaceutically acceptable salt thereof, in a pharmaceutically acceptable carrier.

4. The pharmaceutical composition comprising a catechol O-methyltransferase (COMT) enzyme-inhibiting compound of claim 2, or a pharmaceutically acceptable salt thereof, in a pharmaceutically acceptable carrier.

5. A COMT-inhibiting compound in accordance with formula I, or a pharmaceutically acceptable salt thereof:

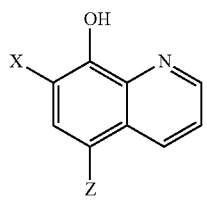

I wherein:
X is halogen or $CF_3$;
Z is $SO_2NR^2R^3$; and
$R^2$ and $R^3$ together form a 3-10 membered monocyclic nitrogen-containing ring system that may be optionally substituted with one or more groups selected from halogen, C≡N, $CF_3$, OH, $C_1$-$C_4$ alkyl or $C_2$-$C_4$ alkenyl, $C_3$-$C_6$ cycloalkyl, alkoxy, nitro, amino, $C_1$-$C_4$ alkoxycarbonyl, acyl, $C_1$-$C_4$ alkylamino, oxo, $SO_2CH_3$, aryl, aralkyl, heterocyclyl, heteroaryl and heteroarylalkyl.

6. The COMT-inhibiting compound of claim 5, or a pharmaceutically acceptable salt thereof, wherein: $R^2$ and $R^3$ together form a pyrrolidine ring system that may be optionally substituted with one or more groups selected from halogen, C≡N, $CF_3$, OH, and $C_1$-$C_4$ alkyl.

7. The COMT inhibiting compound in accordance with claim 1, wherein:
$R^2$ and $R^3$ are independently selected from any of the groups as defined for $R^1$; or $R^2$ and $R^3$ may together form a 3-10 membered monocyclic, bicyclic or spirocyclic nitrogen-containing ring system that contains 0-3 additional heteroatoms selected from oxygen (O), nitrogen (N), and sulfur (S), and which may be further substituted with one or more groups selected from halogen, C≡N, $CF_3$, OH, $C_1$-$C_4$ alkyl or $C_2$-$C_4$ alkenyl, $C_3$-$C_6$ cycloalkyl, alkoxy, nitro, amino, $C_1$-$C_4$ alkoxycarbonyl, acyl, $C_1$-$C_4$ alkylamino, oxo, $SO_2CH_3$, aryl, aralkyl, heterocyclyl, heteroaryl and heteroarylalkyl.

8. The compound of claim 1, wherein $R^1$ is selected from the group consisting of ethyl, 2-propanyl, 2-methylpropyl, octyl, 3-cyclopropylpropyl, 4-methylbenzyl, 2-(4-methylphenyl)ethyl, cyclopentyl, cyclohexyl, 3-methylphenyl, 4-methylphenyl, 2,4-dimethylphenyl, 3,4-dimethylphenyl, 3,5-dimethylphenyl, 2-trifluoromethylphenyl, 3-trifluoromethylphenyl, 4-trifluoromethylphenyl, 4-tert-butylphenyl, 3-chlorophenyl, 4-chlorophenyl, 4-fluorophenyl, 3,5-dichlorophenyl, 3,4-dichlorophenyl, 4-fluoro-2-methylphenyl, 3-(quinolin-5-yl)phenyl, biphenyl-3-yl, 3'-chloro-4'-fluorobiphenyl-3-yl, 3-(1H-indazol-4-yl)phenyl, 3-(pyridin-4-yl)phenyl, 2-naphthyl, 2-pyridinyl, 3-pyridinyl, 4-pyridinyl, 3-methylpyridin-4-yl, 1-(2,3-dimethylphenyl)pyridin-4-yl, 4-piperidinyl, 1-(2,3-dichlorobenzoyl)piperidin-4-yl, (4-fluorobenzyl)piperidin-4-yl, 1-(4-fluorophenyl)-piperidin-4-yl, 1-(2,3-dichlorobenzyl)piperidin-4-yl, 1-(2-chlorobenzyl)-1H-benzimidazol-4-yl, and tetrahydro-2H-pyran-4-yl.

9. The compound of claim 1, wherein the halogen is fluorine.

10. The COMT-inhibiting compound of claim 5 selected from the group consisting of:
7-fluoro-5-(p-tolylsulfonyl)quinolin-8-ol;
7-fluoro-5-[4-[(4-fluorophenyl)methyl]piperazin-1-yl]sulfonyl-quinolin-8-ol;
7-fluoro-5-pyrrolidin-1-ylsulfonyl-quinolin-8-ol; and
7-fluoro-8-hydroxy-N-methyl-N-[(1R)-1-phenylethyl]quinoline-5-sulfonamide.

11. The COMT-inhibiting compound of claim 10 wherein the compound is:
7-fluoro-5-(p-tolylsulfonyl)quinolin-8-ol.

12. The COMT-inhibiting compound of claim 10 wherein the compound is:
7-fluoro-5-[4-[(4-fluorophenyl)methyl]piperazin-1-yl]sulfonyl-quinolin-8-ol.

13. The COMT-inhibiting compound of claim 10 wherein the compound is:
7-fluoro-5-pyrrolidin-1-ylsulfonyl-quinolin-8-ol.

14. The COMT-inhibiting compound of claim 10 wherein the compound is:
7-fluoro-8-hydroxy-N-methyl-N-[(1R)-1-phenylethyl]quinoline-5-sulfonamide.

15. The COMT-inhibiting compound of claim 5, or a pharmaceutically acceptable salt thereof, wherein X is a halogen.

* * * * *

UNITED STATES PATENT AND TRADEMARK OFFICE
CERTIFICATE OF CORRECTION

PATENT NO.         : 10,035,799 B2
APPLICATION NO.    : 15/011353
DATED              : July 31, 2018
INVENTOR(S)        : James Barrow et al.

Page 1 of 1

It is certified that error appears in the above-identified patent and that said Letters Patent is hereby corrected as shown below:

In the Claims

Column 141, Line 19, (approx.) in Claim 3:
Please replace the first word, "The" with an "A".

Column 141, Line 23, (approx.) in Claim 4:
Please replace the first word, "The" with an "A".

Signed and Sealed this
Third Day of November, 2020

Andrei Iancu
*Director of the United States Patent and Trademark Office*